(12) United States Patent
Kielian

(10) Patent No.: US 9,457,030 B2
(45) Date of Patent: Oct. 4, 2016

(54) COMPOSITIONS AND METHODS FOR THE TREATMENT OF JUVENILE NEURONAL CEROID LIPOFUSCINOSIS AND RELATED DISORDERS

(71) Applicant: BOARD OF REGENTS OF THE UNIVERSITY OF NEBRASKA, Lincoln, NE (US)

(72) Inventor: Tammy Kielian, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 0 days.

(21) Appl. No.: 14/066,506

(22) Filed: Oct. 29, 2013

(65) Prior Publication Data

US 2014/0121166 A1    May 1, 2014

Related U.S. Application Data

(60) Provisional application No. 61/719,688, filed on Oct. 29, 2012.

(51) Int. Cl.
| | | |
|---|---|---|
| *A61K 31/522* | (2006.01) | |
| *A61K 31/4545* | (2006.01) | |
| *A61K 31/4015* | (2006.01) | |
| *A61K 31/44* | (2006.01) | |
| *A61K 31/4425* | (2006.01) | |
| *A61K 45/06* | (2006.01) | |
| *A61K 38/17* | (2006.01) | |

(52) U.S. Cl.
CPC ......... *A61K 31/522* (2013.01); *A61K 31/4015* (2013.01); *A61K 31/44* (2013.01); *A61K 31/4425* (2013.01); *A61K 31/4545* (2013.01); *A61K 38/177* (2013.01); *A61K 45/06* (2013.01)

(58) Field of Classification Search
CPC . A61K 31/522; A61K 31/4015; A61K 31/44
See application file for complete search history.

(56) References Cited

PUBLICATIONS

Adams et al., Genotype does not predict severity of behavioural phenotype in juvenile neuronal ceroid lipofuscinosis (Batten disease), *Dev Med Child Neurol.*, 52(7):637-43 (2010).
Allan et al., Interleukin-1 and neuronal injury, *Nat Rev Immunol.*, 5(8):629-40 (2005).
Anonymous, Isolation of a novel gene underlying Batten disease, CLN3. The International Batten Disease Consortium, *Cell*, 82:949-57 (1995).
Antonawich et al., Nesting and shredding behavior as an indicator of hippocampal ischemic damage, *Brain Res.*, 764(1-2):249-52 (1997).
Arai et al., Neurotoxic effects of lipopolysaccharide on nigral dopaminergic neurons are mediated by microglial activation, interleukin-1 beta, and expression of caspase-11 in mice, *J. Biol. Chem.*, 279:51647-53 (2004).
Atkins et al., Modulation of the cAMP signaling pathway after traumatic brain injury, *Exp. Neurol.*, 208(1):145-58 (2007).
Bal-Price et al., Inflammatory neurodegeneration mediated by nitric oxide from activated glia-inhibiting neuronal respiration, causing glutamate release and excitotoxicity, *J. Neurosci.*, 21:6480-91 (2001).
Bargiotas et al., Hemi-channels in cerebral ischemia, *Curr. Mol. Med.*, 9:186-94 (2009).
Bates et al., Inhibition of N-acetylaspartate production: implications for 1H MRS studies in vivo, *Neuroreport.*, 7(8):1397-400 (1996).
Beattie et al., Control of synaptic strength by glial TNFalpha, *Science*, 295(5563):2282-5 (2002).
Beavo, Cyclic nucleotide phosphodiesterases: functional implications of multiple isoforms, *Physiol Rev.*, 75(4):725-48 (1995).
Benedict et al., Progressive oxidative damage in the central nervous system of a murine model for for juvenile Batten disease, *J. Neurosci. Res.*, 85:2882-91 (2007).
Bible et al., Regional and cellular neuropathology in the palmitoyl protein thioesterase-1 null mutant mouse model of infantile neuronal ceroid lipofuscinosis, *Neurobiol. Dis.*, 16(2):346-59. (2004).
Blasko et al., How chronic inflammation can affect the brain and support the development of Alzheimer's disease in old age: the role of microglia and astrocytes, *Aging Cell*, 3(4):169-76 (2004).
Block et al., Microglia-mediated neurotoxicity: uncovering the molecular mechanisms, *Nat. Rev. Neurosci.*, 8:57-69 (2007).
Brockmann et al., Localized proton magnetic resonance spectroscopy of cerebral metabolic disturbances in children with neuronal ceroid lipofuscinosis, *Neuropediatrics*, 27(5):242-8 (1996).
Chatziioannou, Instrumentation for molecular imaging in preclinical research: Micro-PET and Micro-SPECT, *Proc. Am. Thorac. Soc.*, 2(6):533-6 (2005).
Chen et al., Inhibition of NADPH oxidase is neuroprotective after ischemia-reperfusion, *J. Cereb. Blood Flow Metab.*, 29:1262-72 (2009).
Cialone et al., Females experience a more severe disease course in Batten disease, *J. Inherit. Metab. Dis.*, 35(3):549-55 (2012).
Clausen et al., Conditional gene targeting in macrophages and granulocytes using LysMcre mice, *Transgenic Res.*, 8:265-77 (1999).
Colton et al., Assessing activation states in microglia, *CNS Neurol. Disord. Drug Targets*, 9:174-91 (2010).
Cotman et al., Cln3(Deltaex7/8) knock-in mice with the common JNCL mutation exhibit progressive neurologic disease that begins before birth, *Hum. Mol. Genet.*, 11(22):2709-21 (2002).

(Continued)

*Primary Examiner* — John Ulm
(74) *Attorney, Agent, or Firm* — Marshall, Gerstein & Borun LLP

(57) ABSTRACT

Provided are materials and methods for the prevention and treatment of Juvenile Neuronal Ceroid Lipofuscinosis comprising administration of an effective amount of at least one of a hemi-channel inhibitor or a phosphodiesterase-4 inhibitor. In some embodiments, the methods comprise administration of an effective amount of each of a hemi-channel inhibitor and a phosphodiesterase-4 inhibitor. Also provided are pharmaceutical compositions comprising a hemi-channel inhibitor or a phosphodiesterase-4 inhibitor, as well as kits comprising at least one effective dose of a hemi-channel inhibitor or a phosphodiesterase-4 inhibitor or a combination of both.

5 Claims, 25 Drawing Sheets

(56) References Cited

PUBLICATIONS

Danesh-Meyer et al., Connexin43 mimetic peptide reduces vascular leak and retinal ganglion cell death following retinal ischaemia, *Brain*, 135:506-20 (2012).

Dastidar et al., Therapeutic benefit of PDE4 inhibitors in inflammatory diseases, *Curr. Opin. Investig. Drugs*, 8(5):364-72 (2007).

Davidson et al., Connexin hemi-channel blockade improves outcomes in a model of fetal ischemia, *Ann. Neurol.*, 71(1):121-32 (2012).

Deacon et al., Hippocampal cytotoxic lesion effects on species-typical behaviours in mice, *Behav. Brain Res.*, 132(2):203-13 (2002).

Deacon, Assessing nest building in mice, *Nat. Protoc.*, 1 (3):1117-9 (2006).

DeMarch et al., Beneficial effects of rolipram in a quinolinic acid model of striatal excitotoxicity, *Neurobiol. Dis.*, 25(2):266-73 (2007).

Esen et al., Central role for MyD88 in the responses of microglia to pathogen-associated molecular patterns, *J. Immunol.*, 176:6802-11 (2006).

Esen et al., Modulation of connexin expression and gap junction communication in astrocytes by the gram-positive bacterium *S. aureus*, *Glia*, 55:104-17 (2007).

Esen et al., Toll-like receptor 2 (TLR2) mediates astrocyte activation in response to the Gram-positive bacterium *Staphylococcus aureus*, *J Neurochem.*, 88:746-58 (2004).

Eugenin et al., The role of gap junction channels during physiologic and pathologic conditions of the human central nervous system, *J. Neuroimmune Pharmacol.*, 7(3):499-518 (2012).

Fehniger et al., Interleukin 15: biology and relevance to human disease, *Blood*, 97(1):14-32 (2001).

Getty et al., Interactions of the proteins of neuronal ceroid lipofuscinosis: clues to function, *Cell Mol. Life Sci.*, 68:453-74 (2011).

Giaume et al., Adrenergic regulation of intercellular communications between cultured striatal astrocytes from the mouse, *Proc. Natl. Acad. Sci. USA*, 88(13):5577-81 (1991).

Giaume et al., Astroglial networks: a step further in neuroglial and gliovascular interactions, *Nat. Rev. Neurosci.*, 11(2):87-99 (2010).

Gong et al., Persistent improvement in synaptic and cognitive functions in an Alzheimer mouse model after rolipram treatment, *J. Clin. Invest.*, 114(11):1624-34 (2004).

Goto et al., Synthesis and biological evaluation of 5-carbamoyl-2-phenylpyrimidine derivatives as novel and potent PDE4 inhibitors, *Bioorg. Med. Chem.*, 21:7025-37 (2013).

Gundersen et al., The efficiency of systematic stereology and its prediction, *J. Microsc.*, 147:229-63 (1987).

Halle et al., The NALP3 inflammasome is involved in the innate immune response to amyloid-beta, *Nat. Immunol.*, 9:857-65 (2008).

Hanamsagar et al., Inflammasome activation and IL-1 beta/IL-18 processing are influenced by distinct pathways in microglia, *J. Neurochem.*, 119:736-48 (2011).

Hellstrom et al., Chronic LPS exposure produces changes in intrinsic membrane properties and a sustained IL-beta-dependent increase in GABAergic inhibition in hippocampal CA1 pyramidal neurons, *Hippocampus*, 15(5):656-64 (2005).

Herrmann et al, Developmental impairments of select neurotransmitter systems in brains of Cln3(Deltaex7/8) knock-in mice, an animal model of juvenile neuronal ceroid lipofuscinosis, *J. Neurosci. Res.*, 86(8):1857-70 (2008).

Hinkerohe et al., Effects of cytokines on microglial phenotypes and astroglial coupling in an inflammatory coculture model, *Glia*, 52:85-97 (2005).

Holley et al.,Th1 and Th17 cells regulate innate immune responses and bacterial clearance during central nervous system infection, *J. Immunol.*, 188(3):1360-70 (2012).

Holm et al., Microglia are required for astroglial Toll-like receptor 4 response and for optimal TLR2 and TLR3 response, *Glia*, 60(4):630-8 (2012).

Huie et al., Glial tumor necrosis factor alpha (TNFalpha) generates metaplastic inhibition of spinal learning, *PLoS One*, 7(6):e39751 (2012).

Iona et al., Characterization of the rolipram-sensitive, cyclic AMP-specific phosphodiesterases: identification and differential expression of immunologically distinct forms in the rat brain, *Mol. Pharmacol.*, 53(1):23-32 (1998).

Karpuk et al., Neuroinflammation alters voltage-dependent conductance in striatal astrocytes, *J. Neurophysiol.*, 108(1):112-23 (2012).

Karpuk et al., Neuroinflammation leads to region-dependent alterations in astrocyte gap junction communication and hemi-channel activity, *J. Neurosci.*, 31:414-25 (2011).

Kielian et al., Toll-like receptor 2 (TLR2) is pivotal for recognition of *S. aureus* peptidoglycan but not intact bacteria by microglia, *Glia*, 49:567-76 (2005).

Kielian et al., Toll-like receptor 2 modulates the proinflammatory milieu in *Staphylococcus aureus*-induced brain abscess, *Infect. Immun.*, 73(11):7428-35 (2005).

Kielian, Glial connexins and gap junctions in CNS inflammation and disease, *J. Neurochem.*, 106:1000-16 (2008).

Kovacs et al., Age-dependent therapeutic effect of memantine in a mouse model of juvenile Batten disease, *Neuropharmacology*, 63(5):769-75 (2012).

Kovacs et al., Attenuation of AMPA receptor activity improves motor skills in a mouse model of juvenile Batten disease, *Exp. Neurol.*, 209(1):288-91 (2008).

Kovacs et al., Temporary inhibition of AMPA receptors induces a prolonged improvement of motor performance in a mouse model of juvenile Batten disease, *Neuropharmacology*, 60(2-3):405-9 (2011).

Kwon et al., Quantifying physical decline in juvenile neuronal ceroid lipofuscinosis (Batten disease), *Neurology*, 77(20):1801-7 (2011).

Laird, Life cycle of connexins in health and disease, *Biochem. J.*, 394:527-43 (2006).

Landis et al., A call for transparent reporting to optimize the predictive value of preclinical research, *Nature*, 490(7419):187-91 (2012).

Lim et al., Distinct patterns of serum immunoreactivity as evidence for multiple brain-directed autoantibodies in juvenile neuronal ceroid lipofuscinosis, *Neuropathol. Appl. Neurobiol.*, 32(5):469-82 (2006).

Liu et al., MyD88 is pivotal for immune recognition of Citrobacter koseri and astrocyte activation during CNS infection, *J. Neuroinflammation.*, 8:35 (2011).

Lucas et al., The role of inflammation in CNS injury and disease, *Br. J. Pharmacol.*, 147 Suppl. 1 :S232-40 (2006).

Macauley et al., Synergistic effects of central nervous system-directed gene therapy and bone marrow transplantation in the murine model of infantile neuronal ceroid lipofuscinosis, *Ann. Neurol.*, 71(6):797-804 (2012).

Marshall et al., A clinical rating scale for Batten disease: reliable and relevant for clinical trials, *Neurology*, 65(2):275-9 (2005).

McCoy et al., TNF signaling inhibition in the CNS: implications for normal brain function and neurodegenerative disease, *J. Neuroinflammation*, 5:45 (2008).

McGeer et al., Inflammation and neurodegeneration in Parkinson's disease, *Parkinsonism Relat. Disord.*, 10 Suppl 1 :S3-7 (2004).

Meme et al., Proinflammatory cytokines released from microglia inhibit gap junctions in astrocytes: potentiation by beta-amyloid, *Faseb. J.*, 20:494-6 (2006).

Miller, A review of chemical issues in 1H NMR spectroscopy: N-acetyl-L-aspartate, creatine and choline, *NMR Biomed.*, 4(2):47-52 (1991).

Miyasaka et al., Fully automated shim mapping method for spectroscopic imaging of the mouse brain at 9.4 T, *Magn. Reson. Med.*, 55(1):198-202 (2006).

Mole et al., New mutations in the neuronal ceroid lipofuscinosis genes, *Eur. J. Paediatr. Neurol.*, 5 Suppl A:7-10 (2001).

Mori et al., Principles of diffusion tensor imaging and its applications to basic neuroscience research, *Neuron*, 51(5):527-39 (2006).

(56) References Cited

OTHER PUBLICATIONS

Nikulina et al., The phosphodiesterase inhibitor rolipram delivered after a spinal cord lesion promotes axonal regeneration and functional recovery, *Proc. Natl. Acad. Sci. USA*, 101(23):8786-90 (2004).

Orellana et al., Amyloid beta-induced death in neurons involves glial and neuronal hemi-channels, *J. Neurosci.*, 31:4962-77 (2011).

Osorio et al., Neurodevelopmental delay in the Cln3Deltaex7/8 mouse model for Batten disease, *Genes Brain Behav.*, 8(3):337-45 (2009).

Parpura et al., Glial cells in (patho)physiology, *J. Neurochem.*, 121(1):4-27 (2012).

Pautler, Mouse MRI: concepts and applications in physiology, *Physiology (Bethesda)*, 19:168-175 (2004).

Pears et al., High resolution 1H NMR-based metabolomics indicates a neurotransmitter cycling deficit in cerebral tissue from a mouse model of Batten disease, *J. Biol. Chem.*, 280(52):42508-14 (2005).

Pearse et al., cAMP and Schwann cells promote axonal growth and functional recovery after spinal cord injury, *Nat. Med.*, 10(6):610-6 (2004).

Pontikis et al., Late onset neurodegeneration in the Cln3-/-mouse model of juvenile neuronal ceroid lipofuscinosis is preceded by low level glial activation, *Brain Res.*, 1023:231-42 (2004).

Pontikis et al., Thalamocortical neuron loss and localized astrocytosis in the Cln3Deltaex7/8 knock-in mouse model of Batten disease, *Neurobiol. Dis.*, 20:823-36 (2005).

Puranam et al., CLN3 defines a novel antiapoptotic pathway operative in neurodegeneration and mediated by ceramide, *Mol. Genet. Metab.*, 66:294-308 (1999).

Puranam et al., Upregulation of Bcl-2 and elevation of ceramide in Batten disease, *Neuropediatrics*, 28:37-41 (1997).

Qin et al., Bone marrow transplantation increases efficacy of central nervous system-directed enzyme replacement therapy in the murine model of globoid cell leukodystrophy, *Mol. Genet. Metab.*, 107(1-2):186-96 (2012).

Retamal et al., Cx43 hemi-channels and gap junction channels in astrocytes are regulated oppositely by proinflammatory cytokines released from activated microglia, *J. Neurosci.*, 27:13781-92 (2007).

Rothwell, Interleukin-1 and neuronal injury: mechanisms, modification, and therapeutic potential, *Brain Behav. Immun.*, 17(3):152-7 (2003).

Salek et al., A metabolomic comparison of mouse models of the Neuronal Ceroid Lipofuscinoses, *J. Biomol. NMR*, 49:175-84 (2011).

Santello et al., TNFalpha in synaptic function: switching gears, *Trends Neurosci.*, 35(10):638-647 (2012).

Scemes, Nature of plasmalemmal functional "hemichannels", *Biochim. Biophys. Acta.*, 1818(8):1880-3 (2012).

Schaal et al., The Therapeutic Profile of Rolipram, PDE Target and Mechanism of Action as a Neuroprotectant following Spinal Cord Injury, *PLoS One*, 7(9):e43634 (2012).

Schultz et al., Clarifying lysosomal storage diseases, *Trends Neurosci.*, 34(8):401-10 (2011).

Seehafer et al., Immunosuppression alters disease severity in juvenile Batten disease mice, *J. Neuroimmunol.*, 230(1-2):169-72 (2011).

Sommer et al., Therapeutic potential of phosphodiesterase type 4 inhibition in chronic autoimmune demyelinating disease, *J. Neuroimmunol.*, 79(1):54-61 (1997).

Stellwagen et al., Synaptic scaling mediated by glial TNF-alpha, *Nature*, 440(7087):1054-9 (2006).

Stevens et al., The classical complement cascade mediates CNS synapse elimination, *Cell*, 131(6):1164-78 (2007).

Stoll et al., Cytokines in CNS disorders: neurotoxicity versus neuroprotection, *J. Neural. Transm. Suppl.*, 59:81-9 (2000).

Tabarean et al., Interleukin-1 beta induces hyperpolarization and modulates synaptic inhibition in preoptic and anterior hypothalamic neurons, *Neuroscience*, 141(4):1685-95 (2006).

Takeuchi et al., Blockade of gap junction hemichannel suppresses disease progression in mouse models of amyotrophic lateral sclerosis and Alzheimer's disease, *PLoS One*, 6(6):e21108 (2011).

Takeuchi et al., Tumor necrosis factor-alpha induces neurotoxicity via glutamate release from hemi-channels of activated microglia in an autocrine manner, *J. Biol. Chem.*, 281 :21362-8 (2006).

Tawfik et al., Efficacy of propentofylline, a glial modulating agent, on existing mechanical allodynia following peripheral nerve injury, *Brain Behav. Immun.*, 21(2):238-46 (2007).

Tawfik et al., Induction of astrocyte differentiation by propentofylline increases glutamate transporter expression in vitro: heterogeneity of the quiescent phenotype, *Glia*, 54(3):193-203 (2006).

Tawfik et al., Propentofylline-induced astrocyte modulation leads to alterations in glial glutamate promoter activation following spinal nerve transection, *Neuroscience*, 152(4):108692 (2008).

Thompson et al., Connexin and pannexin hemi-channels of neurons and astrocytes, *Channels*, 2:81-6 (2008).

Thornton et al., Interleukin-1-induced neurotoxicity is mediated by glia and requires caspase activation and free radical release, *J. Neurochem.*, 98:258-66 (2006).

Ting et al., Discovery of oral and inhaled PDE4 inhibitors, *Bioorg. & Med. Chem. Lett.*, 23:5528-32 (2013).

Troadec et al., Activation of the mitogen-activated protein kinase (ERK(1/2)) signaling pathway by cyclic AMP potentiates the neuroprotective effect of the neurotransmitter noradrenaline on dopaminergic neurons, *Mol. Pharmacol.*, 62(5):1043-52 (2002).

Tuxworth et al., The Batten disease gene CLN3 is required for the response to oxidative stress, *Hum. Mol. Genet.*, 20:2037-47 (2011).

Urenjak et al., Specific expression of N-acetylaspartate in neurons, oligodendrocyte-type-2 astrocyte progenitors, and immature oligodendrocytes in vitro, *J. Neurochem.*, 59(1):55-61 (1992).

Valenzuela et al., Magnetic resonance spectroscopy in AD, *Neurology*, 56(5):592-8 (2001).

Williams et al., New nomenclature and classification scheme for the neuronal ceroid lipofuscinoses, *Neurology*, 79(2):183-91 (2012).

Wyss-Coray et al., Inflammation in neurodegenerative disease—a double-edged sword, *Neuron*, 35(3):419-32 (2002).

Xiong et al., Microglia in juvenile neuronal ceroid lipofuscinosis are primed toward a pro-inflammatory phenotype, *J. Neurochem.*, 127(2):245-58 (2013).

Zhou et al., A role for mitochondria in NLRP3 inflammasome activation, *Nature*, 469:221-5 (2011).

| | ALP | ALT | TBIL | BUN | Ca²⁺ | PHOS | GLU | Na⁺ | TP |
|---|---|---|---|---|---|---|---|---|---|
| Normal range | 35-222 u/l | 17-77 u/l | 0-0.9 mg/dl | 9-33 mg/dl | 6-13 mg/dl | 5.7-9.2 mg/dl | 140-263 mg/dl | 110-195 mmol/l | 3.9-6.4-g/dl |
| WT-PBS, n=3 | 55.7 ± 30 | 50 ± 7 | 0.17 ± 0.1 | 24 ± 2 | 10.5 ± 0.1 | 10.8 ± 1.7 | 185 ± 36 | 151 ± 0.6 | 5.8 ± 0.2 |
| WT-INI, n=2 | 73 ± 55 | 51 ± 11 | 0.20 ± 0.1 | 29 ± 8 | 10.4 ± 0.1 | 9.2 ± 1.4 | 174 ± 27 | 151 ± 1.5 | 6.1 ± 0.3 |
| KI-PBS, n=2 | 83 ± 3 | 27 ± 1 | 0.25 ± 0.1 | 20 ± 1 | 9.9 ± 0.1* | 6.9 ± 1.0 | 187 ± 23 | 147 ± 0.5** | 6.0 ± 0.1 |
| KI-INI, n=3 | 57.3 ± 12 | 22 ± 3 | 0.15 ± 0.1 | 22 ± 2 | 9.8 ± 0.2* | 8.8 ± 0.5 | 151 ± 14 | 147 ± 1.7** | 5.8 ± 0.3 |

*, **, Significantly different in CLN3 mutant (KI) versus WT

Figure 20B

(ND = not detected)

COMPOSITIONS AND METHODS FOR THE TREATMENT OF JUVENILE NEURONAL CEROID LIPOFUSCINOSIS AND RELATED DISORDERS

CROSS-REFERENCE TO RELATED APPLICATION

This application claims the priority benefit of Provisional U.S. Patent Application No. 61/719,688, filed Oct. 29, 2012.

FIELD OF THE DISCLOSURE

The disclosed technology generally relates to the field of molecular biology in the context of disease prevention or treatment.

BACKGROUND

Lysosomal storage diseases are a class of metabolic disorders caused by mutations in proteins important for lysosomal function. There are many types of lysosomal storage diseases, and although each is relatively rare, their combined prevalence is estimated to be 1 in 8,000 live births[1]. Juvenile neuronal ceroid lipofuscinosis (JNCL or Juvenile Batten disease) is a fatal, neurodegenerative lysosomal storage disease that typically presents in children between the ages of 5-10 years, initiating as blindness and progressing to seizures, motor loss, and subsequent cognitive decline[2]. Juvenile Batten Disease is caused by an autosomal recessive mutation in the CLN3 gene, most commonly due to a 1 kb deletion in exons 7 and 8[3], and although the protein has been shown to reside in lysosomal membranes and other membrane compartments, its function remains elusive. Juvenile Batten Disease is characterized by the abnormal intracellular accumulation of lipid and protein (ceroid lipofuscin) in lysosomes, resulting in the development of insoluble inclusions. Although lysosomal inclusions form in all cell types in the body, neurons are the most sensitive and undergo progressive cell death[2]. The seriousness of this neuronal cell death is magnified by the fact that the central nervous system (CNS) is not capable of regeneration. Currently, there is no treatment for Juvenile Batten Disease, which is uniformly fatal and associated with a decreased life expectancy into the late teens or early twenties.

Microglia play a role in initiating inflammatory events immediately following CNS bacterial infection or insult. In particular, the inflammasome has been defined as a key molecular pathway responsible for processing the proinflammatory cytokine interleukin-1 beta (IL-1β) into its active form in microglia[8]. Depending on the initiating stimulus, activated microglia also produce reactive oxygen species (ROS)[9,10], which have recently been shown to trigger inflammasome activation[11], linking the two processes. Studies have revealed oxidative imbalance in the brains of CLN3 knockout mice[12] and increased sensitivity of CLN3 mutant *Drosophila* to oxidative stress[13]. Further, IL-1β has long been recognized for its neurotoxic properties[6,14]. Collectively, these observations indicate that these pathways intersect and provide a pathological target following CLN3 mutation.

Mass spectrometry studies of samples from the brains of JNCL patients have identified several perturbations in the CNS metabolome[7]. In particular, the disease is associated with elevated glutamate levels, which is thought to contribute to neuronal excitotoxicity. Astrocytes play a major role in maintaining glutamate concentrations through glutamate transporters and gap junction communication (GJC)[8].

Astrocytes form syncytial networks within the CNS through GJC to influence expansive parenchymal domains. Gap junctions (GJs) are formed by the joining of two hemi-channels (HCs) between adjacent cells each composed of six connexin (Cx) subunits[1]. Astrocytic GJs are capable of transmitting a wide variety of small molecules (<1 kDa), including glutamate, ATP, glucose, $Ca^{2+}$, $K^+$, and $Na^{2+}$ and, as such, play a vital role in maintaining ionic and metabolic stability in the CNS parenchyma. In contrast, astrocyte HCs allow the direct communication between the intra- and extracellular milieus and can be formed by two distinct families, namely Cxs and pannexins (Panx)[2].

Numerous neurodegenerative diseases, including JNCL, are typified by an inflammatory component and our recent studies have revealed that primary microglia from $CLN3^{\Delta ex7/8}$ mice are inappropriately primed to secrete elevated levels of numerous proinflammatory mediators following exposure to C6 ceramide and neuronal lysates, two stimuli that are elevated in the brains of JNCL patients[3,4], whereas wild type microglia are relatively non-responsive[38].

Unfortunately, our understanding of the etiology of this devastating disease is limited. Therefore, a need exists in the art for prophylactic and therapeutic methods for individuals diagnosed with Juvenile Neuronal Ceroid Lipofuscinosis or Juvenile Batten Disease. A need also exists for the prophylactics and therapeutics used in those methods.

SUMMARY

The disclosure provides compositions and methods for the prevention or treatment of Juvenile neuronal Ceroid Lipofuscinosis (JNCL or Juvenile Batten Disease) and related disorders. Compositions useful in methods according to the disclosure include hemi-channel (HC) inhibitors. It is envisioned that HC inhibitors are used to treat JNCL.

Compositions according to the disclosure include, but are not limited to, an HC inhibitor such as INI-0602, glycyrrhizic acid, 18α-glycyrrhetinic acid, carbenoxolone, carbenoxolone derivatives that cross the blood-brain barrier, carbenoxolone analogs, fenamates, flufenemic acid, flufenemic acid derivatives, flufenemic acid analogs, heptanol, octanol, arachidonic acid, quinine, quinine derivatives (including mefloquine), connexin (Cx) fragments (including fragments from the extracellular domain of a connexin such as Connexin 43 or Connexin 30), connexin mimetic peptides including but not limited to Gap26 and Gap27, connexin inhibitors, connexin antibodies, connexin expression modulators such as siRNA, shRNA, miRNA and other oligonucleotides that regulate connexin expression (e.g., Nexagon®), Peptagon™, protein kinase C, Src, lysophosphatidic acid, inhibitors of arachidonic acid metabolism, niflumic acid, 5-nitro-2(3-phenylpropylamino)benzoic acid and a heavy metal such as lanthanum or gadolinium.

Compositions useful in methods according to the disclosure also include PDE4 inhibitors. In some embodiments, the PDE4 inhibitor is any PDE4 inhibitor and in some embodiments, the PDE4 inhibitor is selected from the group consisting of propentofylline, apremilast, cilomilast, diazepam, drotaverine, etazolate, filaminast, glaucine, HT-0712, ibudilast, luteolin, mesembrine, mesembrenone, pentoxifylline, piclamilast, rolipram, roflumilast, ronomilast, RPL-554, GSK256066, chlorbipram, 5-carbamoyl-2-phenylpyrimidine derivatives, MK-0952, MK-0359, MK-0873, KCA-1490, N-(3,5-dichloropyridin-4-yl)-7-methoxy-2-(trifluoromethyl)pyrazolo[1,5-a]pyridine-4-carboxamide, and thalidomide. Additional PDE4 inhibitors contemplated as useful in the methods and compositions of the disclosure are disclosed in Ting et al., Bioorg. & Med. Chem. Lett. 23:5528-5532 (2013) and Goto et al., Bioorg. Med. Chem. 21:7025-7037 (2013), each incorporated herein by reference.

Other aspects of the disclosure contemplate methods or uses according to the disclosure that comprise use, or administration, of an HC inhibitor and a PDE4 inhibitor to a subject such as a human. In various embodiments, the HC inhibitor is INI-0602, glycyrrhizic acid, 18α-glycyrrhetinic acid, carbenoxolone, carbenoxolone derivatives that cross the blood-brain barrier, carbenoxolone analogs, fenamates, flufenemic acid, flufenemic acid derivatives, flufenemic acid analogs, heptanol, octanol, arachidonic acid, quinine, quinine derivatives (including mefloquine), connexin (Cx) fragments (including fragments from the extracellular domain of a connexin such as Connexin 43 or Connexin 30), connexin mimetic peptides including but not limited to Gap26 and Gap27, connexin inhibitors, connexin antibodies, connexin expression modulators such as siRNA, shRNA, miRNA and other oligonucleotides that regulate connexin expression (e.g., Nexagon®), Peptagon™, protein kinase C, Src, lyso-phosphatidic acid, inhibitors of arachidonic acid metabolism, niflumic acid, 5-nitro-2(3-phenylpropylamino)benzoic acid or a heavy metal such as lanthanum or gadolinium. In various embodiments, the PDE4 inhibitor is propentofylline, apremilast, cilomilast, diazepam, drotaverine, etazolate, filaminast, glaucine, HT-0712, ibudilast, luteolin, mesembrine, mesembrenone, pentoxifylline, piclamilast, rolipram, roflumilast, ronomilast, RPL-554, GSK256066, chlorbipram, 5-carbamoyl-2-phenylpyrimidine derivatives, MK-0952, MK-0359, MK-0873, KCA-1490, N-(3,5-dichloropyridin-4-yl)-7-methoxy-2-(trifluoromethyl)pyrazolo[1,5-a]pyridine-4-carboxamide, or thalidomide. It is further envisioned that the HC inhibitor and/or the PDE4 inhibitor can be co-administered with other drugs for the treatment of JNCL and related disorders. In some embodiments, the HC inhibitor, the PDE4 inhibitor, or both therapeutics are permeable to the blood-brain barrier.

Consistent with the foregoing descriptions, one aspect of the disclosure provides a method of reducing the rate of development of Juvenile Neuronal Ceroid Lipofuscinosis comprising administering an effective amount of a hemi-channel inhibitor or a phosphodiesterase-4 inhibitor, or both therapeutics, to a subject. Contemplated within the scope of this aspect of the disclosure are embodiments in which JNCL is prevented as well as embodiments in which JNCL at any point in the progression of the disease is subjected to a method to reduce the rate of further development of the condition. Some embodiments of the methods comprise administering an effective amount of a hemi-channel inhibitor or/and a phosphodiesterase-4 inhibitor to a subject. Embodiments of the methods are provided wherein the hemi-channel inhibitor is selected from the group consisting of INI-0602, glycyrrhizic acid, 18α-glycyrrhetinic acid, carbenoxolone, a carbenoxolone derivative, a carbenoxolone analog, a fenamate, flufenemic acid, a flufenemic acid derivative, a flufenemic acid analog, heptanol, octanol, arachidonic acid, quinine, a quinine derivative, a connexin (Cx) fragment, a connexin mimetic peptide, a connexin inhibitor, an anti-connexin antibody, a connexin expression modulator, a lysophosphatidic acid, an inhibitor of arachidonic acid metabolism, niflumic acid, 5-nitro-2(3-phenylpropylamino)benzoic acid and a heavy metal.

In some embodiments of this aspect of the disclosure, the quinine derivative is mefloquine. Embodiments are also contemplated in which the connexin fragment is a fragment of Connexin 43 or Connexin 30. Methods in which the fragment comprises an extracellular domain of a connexin are also embraced in this aspect of the disclosure. There are embodiments wherein the connexin mimetic peptide is Gap26 or Gap27. Embodiments are also comprehended wherein the connexin expression modulator is siRNA, shRNA, miRNA, Nexagon®, Peptagon™, Protein Kinase C or Src, and embodiments wherein the heavy metal is lanthanum or gadolinium are contemplated. In some embodiments, the hemi-channel inhibitor is INI-0602.

This aspect of the disclosure also embraces methods of reducing the rate of development of Juvenile Neuronal Ceroid Lipofuscinosis comprising administering an effective amount of a phosphodiesterase-4 inhibitor, either alone or with administration of a hemi-channel inhibitor. Embodiments include methods wherein the phosphodiesterase-4 inhibitor being administered is selected from the group consisting of propentofylline, apremilast, cilomilast, diazepam, drotaverine, etazolate, filaminast, glaucine, HT-0712, ibudilast, luteolin, mesembrine, mesembrenone, pentoxifylline, piclamilast, rolipram, roflumilast, ronomilast, RPL-554, GSK256066, chlorbipram, MK-0952, MK-0359, MK-0873, KCA-1490, N-(3,5-dichloropyridin-4-yl)-7-methoxy-2-(trifluoromethyl)pyrazolo[1,5-a]pyridine-4-carboxamide and thalidomide. In some embodiments, the phosphodiesterase-4 inhibitor is propentofylline, roflumilast, or rolipram. As noted above, this aspect of the disclosure also contemplates embodiments wherein an effective amount of a hemi-channel inhibitor and an effective amount of a phosphodiesterase-4 inhibitor are administered to a subject. In some embodiments, the HC inhibitor, the PDE4 inhibitor, or both therapeutics are permeable to the blood-brain barrier.

Another aspect of the disclosure is drawn to a method of treating Juvenile Neuronal Ceroid Lipofuscinosis comprising administering an effective amount of a hemi-channel inhibitor or a phosphodiesterase-4 inhibitor, or both therapeutics, to a subject. In some embodiments, the method comprises administering an effective amount of a hemi-channel inhibitor and a phosphodiesterase-4 inhibitor to a subject. Contemplated are embodiments wherein the hemi-channel inhibitor is selected from the group consisting of INI-0602, glycyrrhizic acid, 18α-glycyrrhetinic acid, carbenoxolone, a carbenoxolone derivative, a carbenoxolone analog, a fenamate, flufenemic acid, a flufenemic acid derivative, a flufenemic acid analog, heptanol, octanol, arachidonic acid, quinine, a quinine derivative, a connexin (Cx) fragment, a connexin mimetic peptide, a connexin inhibitor, an anti-connexin antibody, a connexin expression modulator, a lysophosphatidic acid, an inhibitor of arachidonic acid metabolism, niflumic acid, 5-nitro-2(3-phenylpropylamino)benzoic acid and a heavy metal.

In some embodiments of this aspect, the quinine derivative is mefloquine. Embodiments are also contemplated in which the connexin fragment is a fragment of Connexin 43 or Connexin 30. Methods in which the fragment comprises an extracellular domain of a connexin are also embraced in this aspect of the disclosure. There are embodiments wherein the connexin mimetic peptide is Gap26 or Gap27. Embodiments are also comprehended wherein the connexin expression modulator is siRNA, shRNA, miRNA, Nexagon®, Peptagon™, Protein Kinase C or Src, and embodiments wherein the heavy metal is lanthanum or gadolinium are contemplated. In some embodiments, the hemi-channel inhibitor is INI-0602. In some embodiments according to this aspect of the disclosure, the phosphodiesterase-4 inhibitor is selected from the group consisting of propentofylline, apremilast, cilomilast, diazepam, drotaverine, etazolate, filaminast, glaucine, HT-0712, ibudilast, luteolin, mesembrine, mesembrenone, pentoxifylline, piclamilast, rolipram, roflumilast, ronomilast, RPL-554, GSK256066, chlorbipram, MK-0952, MK-0359, MK-0873, KCA-1490, N-(3,5-dichloropyridin-4-yl)-7-methoxy-2-(trifluoromethyl)pyrazolo[1,5-a]pyridine-4-carboxamide and thalidomide. In some embodiments, the phosphodiesterase-4 inhibitor is propentofylline, roflumilast, or rolipram. This aspect of the disclosure also contemplates embodiments wherein an effective amount of a hemi-channel inhibitor and an effective amount of a phosphodiesterase-4 inhibitor are administered to a subject. In some embodiments, the HC inhibitor, the PDE4 inhibitor, or both therapeutics are permeable to the blood-brain barrier.

Yet another aspect of the disclosure is a method of modulating a parameter of central nervous system physiology comprising administering an effective amount of hemi-channel inhibitor or phosphodiesterase-4 inhibitor, or both therapeutics, to a subject, wherein the modulating of a parameter is selected from the group consisting of reducing the rate of extracellular glutamate accumulation, reducing the rate of hemi-channel transfer, reducing the rate of hemi-channel opening, reducing an anti-inflammatory effect, modulating aberrant glial activation, modulating astrocyte function, and preventing a motor deficit, such as gait and balance. In some embodiments, the method comprises administering an effective amount of a hemi-channel inhibitor and a phosphodiesterase-4 inhibitor to a subject. In some embodiments, the hemi-channel inhibitor is selected from the group consisting of INI-0602, glycyrrhizic acid, 18α-glycyrrhetinic acid, carbenoxolone, a carbenoxolone derivative, a carbenoxolone analog, a fenamate, flufenemic acid, a flufenemic acid derivative, a flufenemic acid analog, heptanol, octanol, arachidonic acid, quinine, a quinine derivative, a connexin (Cx) fragment, a connexin mimetic peptide, a connexin inhibitor, an anti-connexin antibody, a connexin expression modulator, a lysophosphatidic acid, an inhibitor of arachidonic acid metabolism, niflumic acid, 5-nitro-2(3-phenylpropylamino)benzoic acid and a heavy metal.

In some embodiments of this aspect, the quinine derivative is mefloquine. Embodiments are also contemplated in which the connexin fragment is a fragment of Connexin 43 or Connexin 30. Methods in which the fragment comprises an extracellular domain of a connexin are also embraced in this aspect of the disclosure. There are embodiments wherein the connexin mimetic peptide is Gap26 or Gap27. Embodiments are also comprehended wherein the connexin expression modulator is siRNA, shRNA, miRNA, Nexagon®, Peptagon™, Protein Kinase C or Src, and embodiments wherein the heavy metal is lanthanum or gadolinium are contemplated. In some embodiments, the hemi-channel inhibitor is INI-0602. Further, this aspect embraces embodiments wherein the phosphodiesterase-4 inhibitor is selected from the group consisting of propentofylline, apremilast, cilomilast, diazepam, drotaverine, etazolate, filaminast, glaucine, HT-0712, ibudilast, luteolin, mesembrine, mesembrenone, pentoxifylline, piclamilast, rolipram, roflumilast, ronomilast, RPL-554, GSK256066, chlorbipram, MK-0952, MK-0359, MK-0873, KCA-1490, N-(3,5-dichloropyridin-4-yl)-7-methoxy-2-(trifluoromethyl)pyrazolo[1,5-a]pyridine-4-carboxamide and thalidomide. In some embodiments, the phosphodiesterase-4 inhibitor is propentofylline, roflumilast, or rolipram. Also contemplated are embodiments wherein an effective amount of a hemi-channel inhibitor and an effective amount of a phosphodiesterase-4 inhibitor are administered to a subject.

Other aspects of the disclosure relate to uses of the disclosed materials (e.g., pharmaceutical compositions), including use of a hemi-channel inhibitor in reducing the rate of development of Juvenile Neuronal Ceroid Lipofuscinosis, or use of a phosphodiesterase-4 inhibitor in reducing the rate of development of Juvenile Neuronal Ceroid Lipofuscinosis. Also embraced is a use of a hemi-channel inhibitor and a phosphodieasterase-4 inhibitor in reducing the rate of development of Juvenile Neuronal Ceroid Lipofuscinosis. Additional uses provide treatment of JNCL, such as a use of a hemi-channel inhibitor in a method of treating Juvenile Neuronal Ceroid Lipofuscinosis, or a use of a phosphodiesterase-4 inhibitor in a method of treating Juvenile Neuronal Ceroid Lipofuscinosis. Additionally contemplated is a use of a hemi-channel inhibitor and a phosphodiesterase-4 inhibitor in a method of treating Juvenile Neuronal Ceroid Lipofuscinosis.

Further uses include use of a hemi-channel inhibitor in a method of modulating a parameter of central nervous system physiology selected from the group consisting of reducing the rate of extracellular glutamate accumulation, reducing the rate of hemi-channel transfer, reducing the rate of hemi-channel opening, reducing an anti-inflammatory effect, modulating aberrant glial activation, modulating astrocyte function and preventing a motor deficit. Additionally disclosed is a use of a phosphodiesterase-4 inhibitor in a method of modulating a parameter of central nervous system physiology selected from the group consisting of reducing the rate of extracellular glutamate accumulation, reducing the rate of hemi-channel transfer, reducing the rate of hemi-channel opening, reducing an anti-inflammatory effect, modulating aberrant glial activation, modulating astrocyte function and preventing a motor deficit. Also contemplated is a use of a hemi-channel inhibitor and a phosphodiesterase-4 inhibitor in a method of modulating a parameter of central nervous system physiology selected from the group consisting of reducing the rate of extracellular glutamate accumulation, reducing the rate of hemi-channel transfer, reducing the rate of hemi-channel opening, reducing an anti-inflammatory effect, modulating aberrant glial activation, modulating astrocyte function and preventing a motor deficit. For each of the uses disclosed herein, any compound or pharmaceutical composition disclosed herein is contemplated may be employed. Suitable hemi-channel inhibitors include INI-0602, glycyrrhizic acid, 18α-glycyrrhetinic acid, carbenoxolone, a carbenoxolone derivative, a carbenoxolone analog, a fenamate, flufenemic acid, a flufenemic acid derivative, a flufenemic acid analog, heptanol, octanol, arachidonic acid, quinine, a quinine derivative, a connexin (Cx) fragment, a connexin mimetic peptide, a connexin inhibitor, an anti-connexin antibody, a connexin expression modulator, a lysophosphatidic acid, an inhibitor of arachidonic acid metabolism, niflumic acid, 5-nitro-2(3-phenylpropylamino)benzoic acid and a heavy metal.

In some embodiments of this aspect of the disclosure, the quinine derivative is mefloquine. Embodiments are also contemplated in which the connexin fragment is a fragment of Connexin 43 or Connexin 30. Methods in which the fragment comprises an extracellular domain of a connexin are also embraced in this aspect of the disclosure. There are embodiments wherein the connexin mimetic peptide is Gap26 or Gap27. Embodiments are also comprehended wherein the connexin expression modulator is siRNA, shRNA, miRNA, Nexagon®, Peptagon™, Protein Kinase C or Src, and embodiments wherein the heavy metal is lanthanum or gadolinium are contemplated. In some embodiments, the hemi-channel inhibitor is INI-0602. Further, this aspect embraces embodiments wherein a phosphodiesterase-4 inhibitor is selected from the group consisting of propentofylline, apremilast, cilomilast, diazepam, drotaverine, etazolate, filaminast, glaucine, HT-0712, ibudilast, luteolin, mesembrine, mesembrenone, pentoxifylline, piclamilast, rolipram, roflumilast, ronomilast, RPL-554, GSK256066, chlorbipram, MK-0952, MK-0359, MK-0873, KCA-1490, N-(3,5-dichloropyridin-4-yl)-7-methoxy-2-(trifluoromethyl)pyrazolo[1,5-a]pyridine-4-carboxamide and thalidomide. In some embodiments, the phosphodiesterase-4 inhibitor is propentofylline, roflumilast, or rolipram. Also contemplated are embodiments wherein an effective amount of a hemi-channel inhibitor and an effective amount of a phosphodiesterase-4 inhibitor are used (e.g., administered to a subject).

A further aspect of the disclosure is a pharmaceutical composition for reducing the development of Juvenile Neuronal Ceroid Lipofuscinosis comprising at least one effective dose of each of a hemi-channel inhibitor and a phosphodiesterase-4 inhibitor, formulated for administration to a living subject, such as a human. In some embodiments of this aspect of the disclosure, the hemi-channel inhibitor is selected from the group consisting of INI-0602, glycyrrhizic acid, 18α-glycyrrhetinic acid, carbenoxolone, a carbenoxolone derivative, a carbenoxolone analog, a fenamate, flufenemic acid, a flufenemic acid derivative, a flufenemic acid analog, heptanol, octanol, arachidonic acid, quinine, a quinine derivative, a connexin (Cx) fragment, a connexin mimetic peptide, a connexin inhibitor, an anti-connexin antibody, a connexin expression modulator, a lysophosphatidic acid, an inhibitor of arachidonic acid metabolism, niflumic acid, 5-nitro-2(3-phenylpropylamino)benzoic acid and a heavy metal.

In some embodiments of this aspect of the disclosure, the quinine derivative is mefloquine. Embodiments are also contemplated in which the connexin fragment is a fragment of Connexin 43 or Connexin 30. Pharmaceutical compositions in which the fragment comprises an extracellular domain of a connexin are also embraced in this aspect of the disclosure. There are embodiments wherein the connexin mimetic peptide is Gap26 or Gap27. Embodiments are also comprehended wherein the connexin expression modulator is siRNA, shRNA, miRNA, Nexagon®, Peptagon™, Protein Kinase C or Src, and embodiments wherein the heavy metal is lanthanum or gadolinium are contemplated. In some embodiments, the hemi-channel inhibitor is INI-0602.

Also, in some embodiments according to this aspect of the disclosure, the phosphodiesterase-4 inhibitor is selected from the group consisting of propentofylline, apremilast, cilomilast, diazepam, drotaverine, etazolate, filaminast, glaucine, HT-0712, ibudilast, luteolin, mesembrine, mesembrenone, pentoxifylline, piclamilast, rolipram, roflumilast, ronomilast, RPL-554, GSK256066, chlorbipram, MK-0952, MK-0359, MK-0873, KCA-1490, N-(3,5-dichloropyridin-4-yl)-7-methoxy-2-(trifluoromethyl)pyrazolo[1,5-a]pyridine-4-carboxamide and thalidomide. In some embodiments, the phosphodiesterase-4 inhibitor is propentofylline, roflumilast, or rolipram. Also contemplated are pharmaceutical compositions comprising an effective amount of a hemi-channel inhibitor and an effective amount of a phosphodiesterase-4 inhibitor, for administration to a subject. Embodiments are also contemplated wherein the pharmaceutical compositions further comprise a biologically acceptable carrier, adjuvant or diluent, as would be known in the art.

A still further aspect of the disclosure is a kit for reducing the development of Juvenile Neuronal Ceroid Lipofuscinosis comprising at least one effective dose of each of a hemi-channel inhibitor and a phosphodiesterase-4 inhibitor. In some embodiments, the hemi-channel inhibitor is selected from the group consisting of INI-0602, glycyrrhizic acid, 18α-glycyrrhetinic acid, carbenoxolone, a carbenoxolone derivative, a carbenoxolone analog, a fenamate, flufenemic acid, a flufenemic acid derivative, a flufenemic acid analog, heptanol, octanol, arachidonic acid, quinine, a quinine derivative, a connexin (Cx) fragment, a connexin mimetic peptide, a connexin inhibitor, an anti-connexin antibody, a connexin expression modulator, a lysophosphatidic acid, an inhibitor of arachidonic acid metabolism, niflumic acid, 5-nitro-2(3-phenylpropylamino)benzoic acid and a heavy metal.

In some embodiments of this aspect, the quinine derivative is mefloquine. Embodiments are also contemplated in which the connexin fragment is a fragment of Connexin 43 or Connexin 30. Kits in which the fragment comprises an extracellular domain of a connexin are also embraced in this aspect of the disclosure. There are embodiments wherein the connexin mimetic peptide is Gap26 or Gap27. Embodiments are also comprehended wherein the connexin expression modulator is siRNA, shRNA, miRNA, Nexagon®, Peptagon™, Protein Kinase C or Src, and embodiments wherein the heavy metal is lanthanum or gadolinium are contemplated. In some embodiments, the hemi-channel inhibitor is INI-0602.

Further, in some embodiments, the phosphodiesterase-4 inhibitor is selected from the group consisting of propentofylline, apremilast, cilomilast, diazepam, drotaverine, etazolate, filaminast, glaucine, HT-0712, ibudilast, luteolin, mesembrine, mesembrenone, pentoxifylline, piclamilast, rolipram, roflumilast, ronomilast, RPL-554, GSK256066, chlorbipram, MK-0952, MK-0359, MK-0873, KCA-1490, N-(3,5-dichloropyridin-4-yl)-7-methoxy-2-(trifluoromethyl)pyrazolo[1,5-a]pyridine-4-carboxamide and thalidomide. In some embodiments, the phosphodiesterase-4 inhibitor is propentofylline, roflumilast, or rolipram. Also contemplated are embodiments wherein the kit comprises at least one effective dose of a hemi-channel inhibitor and at least one effective dose of a phosphodiesterase-4 inhibitor. In some embodiments, the kit therapeutics are formulated for administration to a living subject, such as a human. In some embodiments, the kits further comprise a biologically acceptable carrier, adjuvant or diluent, as would be known in the art.

Other features and advantages of the disclosure will become apparent from the following detailed description, including the drawing. It should be understood, however, that the detailed description and the specific examples, while indicating embodiments, are provided for illustration only, because various changes and modifications within the spirit and scope of the disclosure will become apparent to those skilled in the art from the detailed description.

Figure 17:
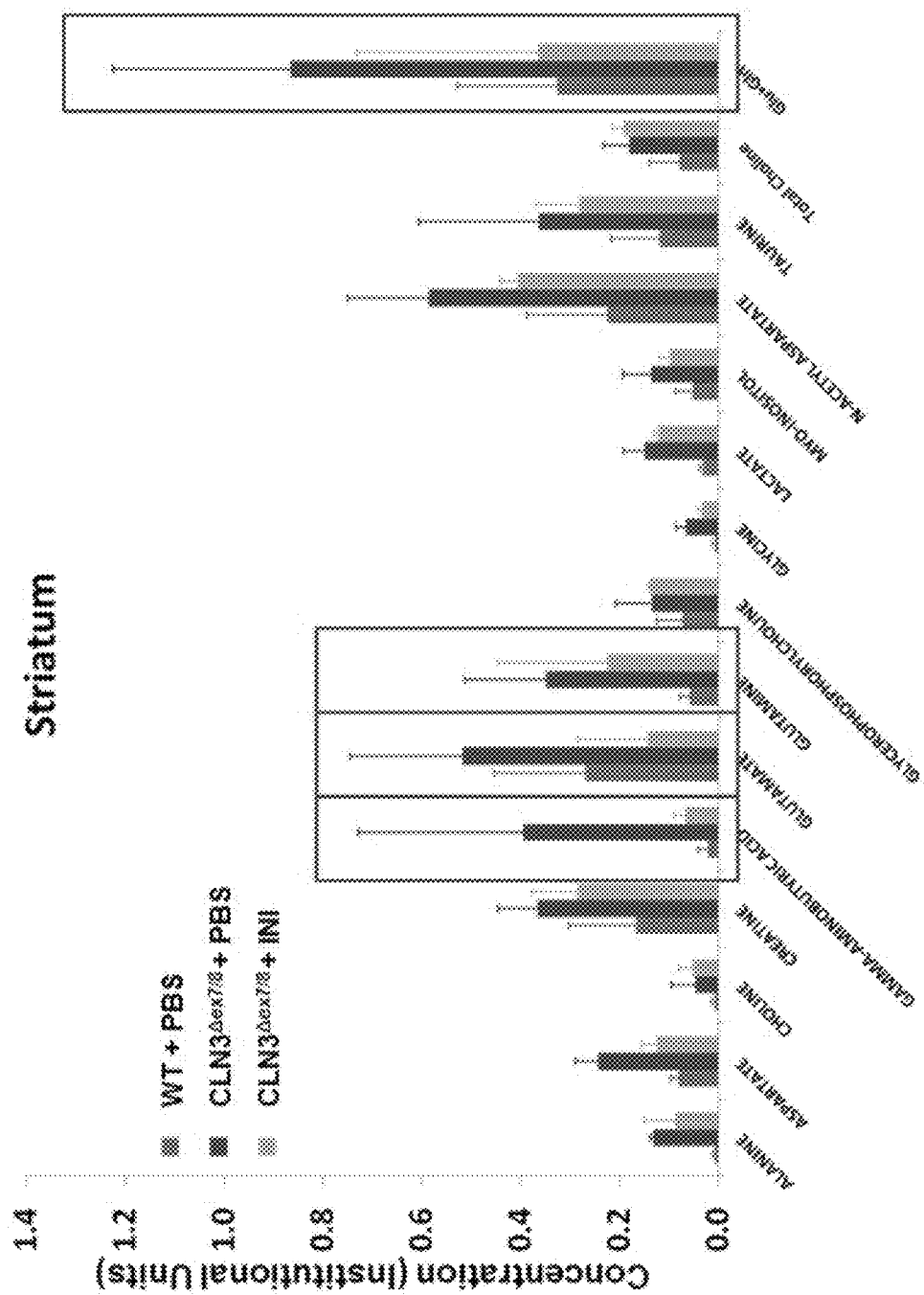

FIG. 17. INI-0602-induced restoration of WT levels of brain metabolites in the CLN3$^{\Delta ex7/8}$ mouse striatum. Mice received i.p. injections of INI-0602 (10 mg/kg) or vehicle (PBS) every other day beginning at postnatal day 30 and continuing until postnatal day 60. Mice were subjected to magnetic resonance spectroscopy (MRS) imaging at day 60 to determine whether INI-0602 treatment had any effects on brain metabolites. Glutamate and glutamine levels are dramatically increased in CLN3 mutant mice (red bars), which was reduced to nearly WT levels by INI-0602 treatment (light green bars). In contrast, gamma-aminobutyric acid (GABA) levels were increased in CLN3 mutant mice and INI-0602 treatment reduced GABA concentrations nearer to that observed in WT mice.

Figure 18:
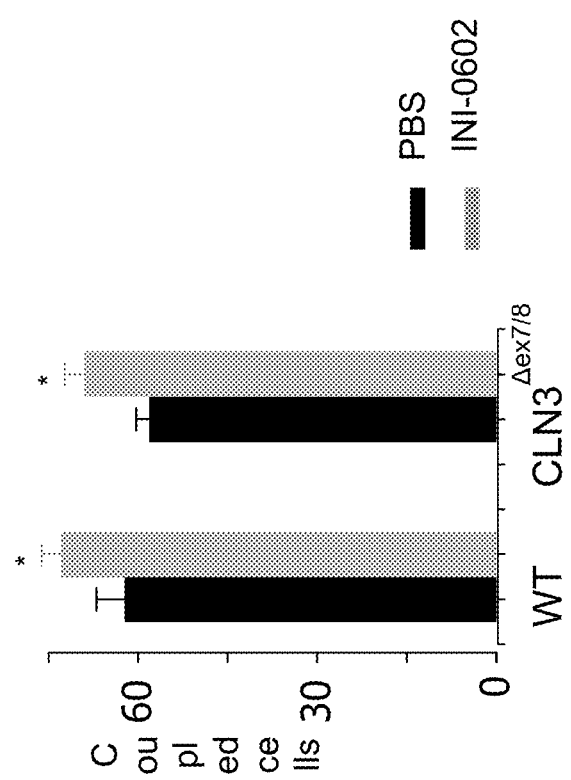

FIG. 18. INI-0602 enhances gap junction communication in both WT and CLN3$^{\Delta ex7/8}$ mice. Mice received i.p. injections of INI-0602 (10 mg/kg) or vehicle (PBS) every other day beginning at postnatal day 30 and continuing until postnatal day 60. Mice were sacrificed at day 60, whereupon the degree of gap junction communication was determined in astrocytes from acute brain slices in the hippocampus and somatosensory barrel field 1 cortex (living tissues). The one-month dosing interval of CLN3 mutant mice with INI-0602 significantly increased gap junction communication compared to PBS treatment.

Figure 19:
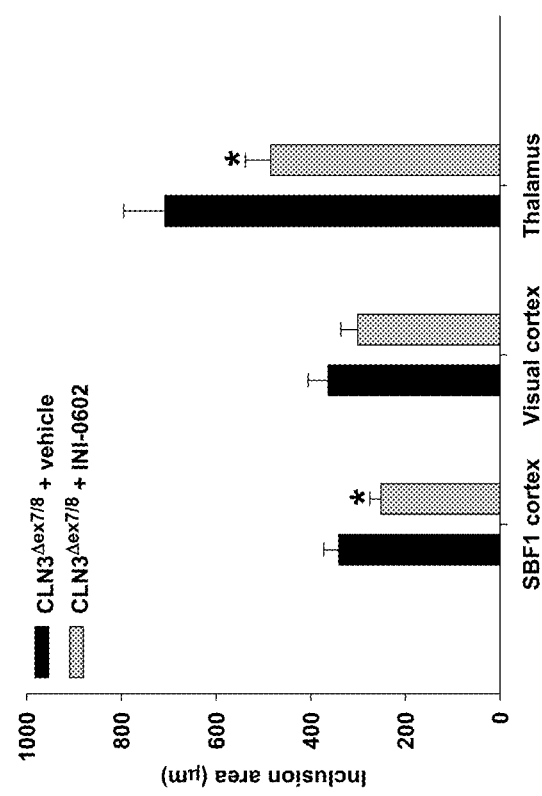

FIG. 19. INI-0602 reduces lysosomal inclusion burden in CLN3$^{\Delta ex7/8}$ mice. LN3$^{\Delta ex7/8}$ mice received 1 mg/kg INI-0602 or vehicle every other day beginning at P30 and storage material deposition was assessed at P60 (*, $p<0.05$).

Figure 20A:
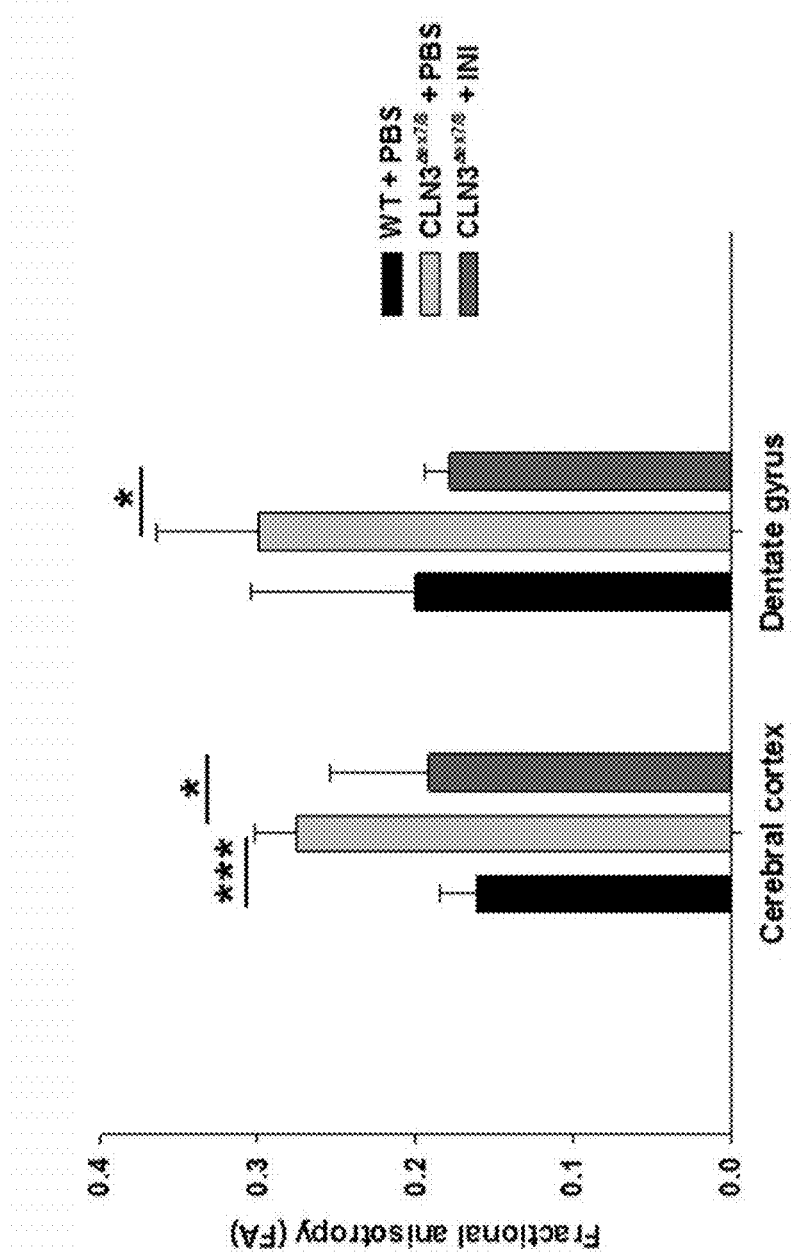

FIG. 20. INI-0602 affects Diffusion Tensor Imaging (DTI) measures in the CLN3$^{\Delta ex7/8}$ mouse brain. A: Mice received i.p. injections of INI-0602 (10 mg/kg) or vehicle (PBS) every other day beginning at postnatal day 30 and continuing until postnatal day 60. Mice were subjected to diffusion tensor imaging (DTI) at day 60 to determine whether INI-0602 treatment had any effects on brain damage. Fractional anisotropy (FA) values are reported and for the grey matter regions shown, the increased FA values observed in CLN3 mutant mice indicate neuron damage. Treatment of CLN3 mutant mice with INI-0602 for one month was able to significantly attenuate this response, with FA values approaching those observed in WT animals; B: Data presented in tabular form showing that, after one month of INI-0602 administration, there is no evidence of toxicity as determined by serum chemistry assays.

Figure 21:
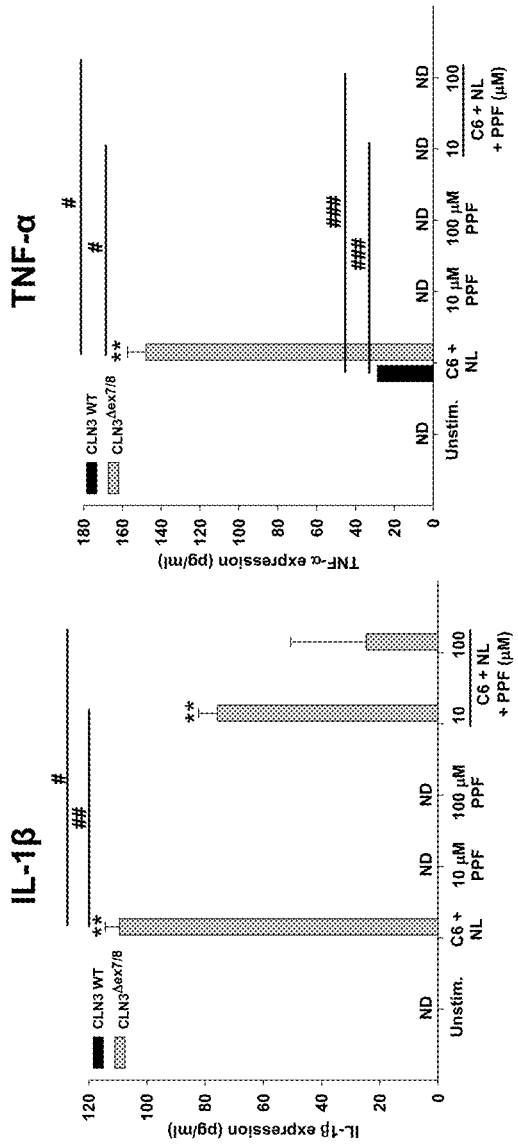

FIG. 21. PDE-4 inhibitors attenuate IL-1β and TNF-α production in CLN3$^{\Delta ex7/8}$ microglia. Primary microglia were isolated from the brains of CLN3 WT or CLN3 mutant mice, whereupon cells were pre-treated with various concentrations of the phosphodiesterase-4 inhibitor propentofylline (PPF) for 1 hour followed by a combination of molecules known to be elevated in the JNCL brain (20 μM ceramide+neuron lysates) for 24 hours. Conditioned medium was collected at 24 hours post-treatment and IL-1β and TNF-α expression was determined by ELISA. **, $p<0.01$ for WT versus CLN3 mutant microglia; #, $p<0.05$; ##, $p<0.01$; ###, $p<0.001$ for CLN3 mutant microglia treated with PPF versus vehicle control.

Figure 22:
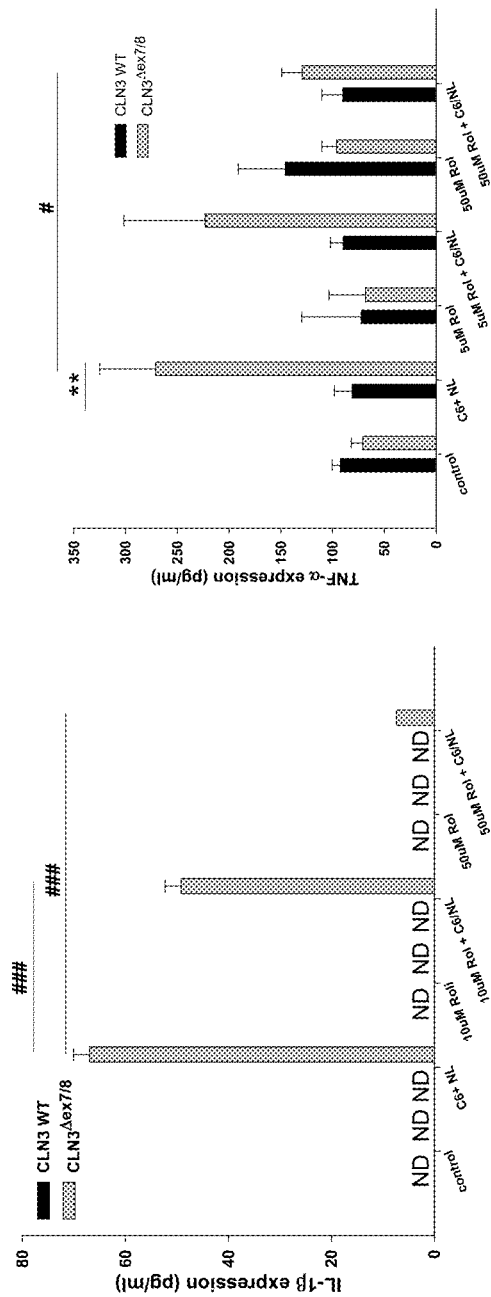

FIG. 22. PDE-4 inhibitors attenuate IL-1β and TNF-α production in CLN3$^{\Delta ex7/8}$ microglia. Primary microglia were isolated from the brains of CLN3 WT or CLN3 mutant mice, whereupon cells were pre-treated with various concentrations of the phosphodiesterase-4 inhibitor rolipram (Rol) for 1 hour followed by a combination of molecules known to be elevated in the JNCL brain (20 μM ceramide+neuron lysates) for 24 hours. Conditioned medium was collected at 24 hours post-treatment and IL-1β and TNF-α expression was determined by ELISA. **, $p<0.01$ for WT versus CLN3 mutant microglia; #, $p<0.05$; ###, $p<0.001$ for CLN3 mutant microglia treated with Rol versus vehicle control.

Figure 23:
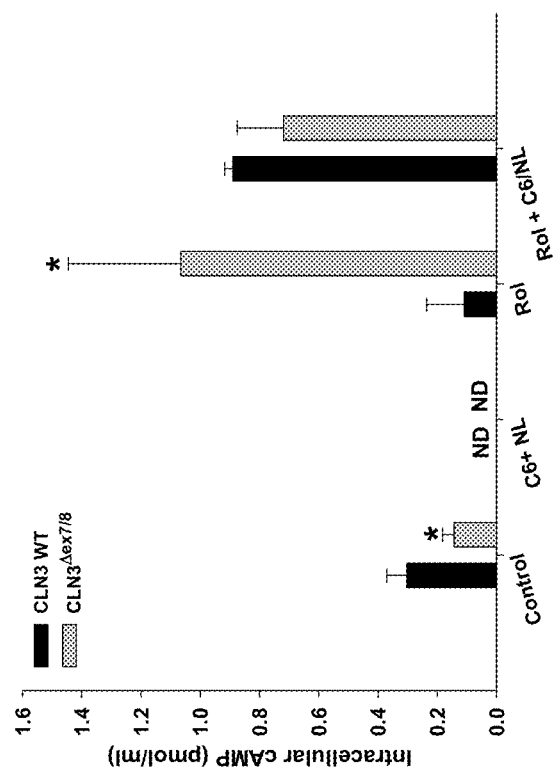

FIG. 23. CLN3$^{\Delta ex7/8}$ microglia display reduced intracellular cAMP constitutively, which is enhanced by the PDE-4 inhibitors. Primary microglia were isolated from the brains of CLN3 WT or CLN3 mutant mice, whereupon cells were pre-treated with the phosphodiesterase-4 inhibitor rolipram (Rol; 10 μM) for 1 hour followed by a combination of molecules known to be elevated in the JNCL brain (20 μM ceramide+neuron lysates) for 24 hours. Intracellular cAMP levels were determined at 24 hours post-treatment (*, $p<0.05$).

Figure 24:
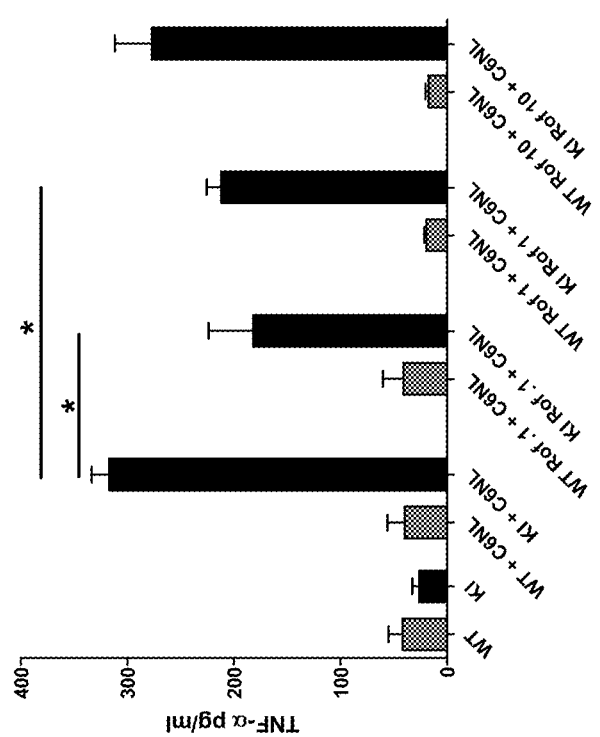

FIG. 24. PDE-4 inhibitors attenuate TNF-α production in CLN3$^{\Delta ex7/8}$ microglia. Primary microglia were isolated from the brains of CLN3 WT or CLN3 mutant mice, whereupon cells were pre-treated with various concentrations of the phosphodiesterase-4 inhibitor roflumilast (Rof) for 1 hour followed by a combination of molecules known to be elevated in the JNCL brain (20 μM ceramide+neuron lysates) for 24 hours. Conditioned medium was collected at 24 hours post-treatment and TNF-α expression was determined by ELISA. **, $p<0.01$ for WT versus CLN3 mutant microglia.

DETAILED DESCRIPTION

Juvenile Neuronal Ceroid Lipofuscinosis (JNCL or Juvenile Batten disease) is a fatal, neurodegenerative lysosomal storage disease that typically presents in children between the ages of 5-10 years, initiating as blindness and progressing to seizures, motor loss, and subsequent cognitive decline. Juvenile Batten Disease is caused by an autosomal recessive mutation in the CLN3 gene, most commonly due to a 1 kb deletion in exons 7 and 8 (CLN3$^{\Delta ex7/8}$), and although lysosomal inclusions occur in all cell types in the body, neurons are the most sensitive and undergo progressive cell death. Evidence exists that activation of resident CNS glia (i.e., microglia and astrocytes) occurs very early after birth (i.e., within one week in JNCL mouse models), yet neurons do not die until much later (i.e., 5-7 months). Areas of early glial activation predict regions where neuron loss will occur later in life, suggesting that perturbations in microglial and/or astrocyte activity may be contributing factors to neuron death during JNCL. Indeed, our data support this possibility, in that primary microglia isolated from CLN3$^{\Delta ex7/8}$ mice are primed to inappropriately respond to stimuli that are elevated in the JNCL brain (i.e., ceramide and neuronal lysates), which are largely ignored by wild-type microglia. In addition, we have also demonstrated that physiological cell-cell communication is impaired during early JNCL. Specifically, protective gap junction communication (GJC) is altered and instead, hemi-channels are open during early disease, which serve as a direct conduit between the intracellular/extracellular milieus, effectively disrupting physiologic ion and metabolic gradients. Since GJC is involved in maintaining pH, ion gradients, and glutamate levels within the CNS, the shift from protective GJC to open hemi-channels that disrupt these homeostatic mechanisms likely contributes to neuronal cell death by dysregulating metabolic networks. Glutamate is elevated in the brains of JNCL patients, and has been suggested as a key mechanism leading to neuron death in addition to ceramide accumulation.

Based on these observations, the efficacy of compounds that target the aberrant microglial activation and hemichannel activity that occurs early in the CLN3$^{\Delta ex7/8}$ mouse model was explored. In adopting this approach, two independent classes of therapeutics were developed, with each class having therapeutic efficacy when administered alone. The two classes of therapeutics also have dramatically different mechanisms of action, and are shown herein to be compatible when co-administered. The classes of therapeutics are the hemi-channel inhibitors and PDE4 inhibitors. The phosphodiesterase-4 inhibitor class of therapeutics is exemplified by propentofylline and the hemi-channel inhibitor class is exemplified by INI-0602. These exemplary therapeutics were subjected to experimental analysis. The results with INI-0602 revealed beneficial effects in CLN3$^{\Delta ex7/8}$ mice, where animals that were treated with INI-0602 for a period of one month (beginning at postnatal day 30 and continuing to postnatal day 60; 10 mg/kg i.p. every other day) revealed improved behavioral performance, reduced glutamate/glutamine accumulation within the CNS, and increased GJC. In particular, we propose that the ability of INI-0602 to enhance GJC in the JNCL brain is important for restoring glutamate levels to that of wild-type animals and improves CNS homeostasis. INI-0602 did not show any evidence of toxicity during the one month treatment interval (as determined by weight and blood chemistry profiles).

The strategy disclosed herein is to use at least one, and optionally two, distinct classes of compounds known to target multiple pathways that are dysregulated during early JNCL. The first class of compounds is hemi-channel (HC) inhibitors, exemplified by INI-0602 (Takeuchi, PLoS ONE 2011; 6(6):e21108, incorporated herein by reference), which exerts neuroprotective effects in mouse models of ALS and AD. Studies by the inventive entity indicate that INI-0602 reduces glutamate accumulation in CLN3$^{\Delta ex7/8}$ mice to levels typical of WT animals. The second therapeutic class includes the phosphodiesterase-4 (PDE-4) inhibitors propentofylline (PPF) rolipram, and roflumilast, which all selectively attenuate proinflammatory mediator production by CLN3$^{\Delta ex7/8}$ microglia. Because PDE-4 inhibitors can also increase astrocyte glutamate transporter expression, PPF, rolipram, and roflumilast are attractive therapeutic candidates based on their ability to modulate multiple pathways implicated in JNCL pathogenesis. Indeed, PDE-4 inhibitors have proven efficacious at reducing neuroinflammation and neuronal loss in rodent models of Alzheimer's Disease, Huntington's Disease, multiple sclerosis, neuropathic pain, and spinal cord injury.

The disclosure provides experiments designed, in part, to identify the optimal neuroprotective regimens for a HC inhibitor (e.g., INI-0602) and a PDE-4 inhibitor in JNCL, by evaluating effects on the brain metabolome, behavioral attributes, and neuronal survival in CLN3$^{\Delta ex7/8}$ mice. In particular, optimal dose-response profiles and delivery route for each drug are established, identifying the ideal therapeutic window for treatment intervention. The potential toxicity of each compound is also evaluated. It is expected that a HC inhibitor (e.g., INI-0602) or a PDE-4 inhibitor will be therapeutically effective when used individually as therapeutics and it is expected that the HC inhibitor and PDE4 inhibitor will display additive effects or synergistic effects in a combinational therapy approach. In addition, the long-term duration of drug action is assessed. This disclosure is significant because no therapeutics currently exist to delay JNCL progression, with current treatments only targeting disease symptoms.

A significant attribute of the chosen compounds used in combinational therapies, which bolster the likelihood of success, is that the compounds target multiple pathways that are dysregulated in JNCL patients as well as CLN3$^{\Delta ex7/8}$ mice. Additionally, compounds in each therapeutic class are capable of crossing the intact blood-brain barrier, which avoids the need for direct CNS injection in some embodiments.

The first compound is a HC inhibitor, which includes derivatives of carbenoxolone such as INI-0602. The disclosure additionally contemplates any HC inhibitor known in the art, including but not limited to, INI-0602, glycyrrhizic acid, 18α-glycyrrhetinic acid, carbenoxolone, carbenoxolone derivatives, carbenoxolone analogs, fenamates, flufenemic acid, flufenemic acid derivatives, flufenemic acid analogs, heptanol, octanol, arachidonic acid, quinine, quinine derivatives (including mefloquine), connexin (Cx) fragments (including fragments from the extracellular domain of a connexin such as Connexin 43 or Connexin 30), connexin mimetic peptides including but not limited to Gap26 and Gap27, connexin inhibitors, connexin antibodies, connexin expression modulators such as siRNA, shRNA, miRNA and other oligonucleotides that regulate connexin expression (e.g., Nexagon®), Peptagon™, protein kinase C, Src, lysophosphatidic acid, inhibitors of arachidonic acid metabolism, niflumic acid, 5-nitro-2(3-phenylpropylamino)benzoic acid and such heavy metals as lanthanum and gadolinium.

HC inhibitors were pursued because the inventive entity discovered aberrant HC opening in CLN3$^{\Delta ex7/8}$ mice as early as postnatal day 30, which is expected to contribute to elevated glutamate levels observed in the JNCL brain. Consistently, data demonstrate that INI-0602 reduced elevated glutamate concentrations in the hippocampus and striatum of CLN3$^{\Delta ex7/8}$ mice to levels reminiscent of WT animals. By closing HCs, INI-0602 enhanced gap junction communication in CLN3$^{\Delta ex7/8}$ mice, which is expected to offset metabolic disturbances in neurons and improve viability. Also consistently, INI-0602 was recently shown to enhance survival in a mouse ALS model as well as reduce memory deficits in AD transgenic mice. The second drug class is the phosphodiesterase-4 (PDE-4) inhibitors, including PPF, rolipram, and roflumilast. Further, the disclosure contemplates any PDE-4 inhibitor known in the art, including but not limited to, propentofylline, apremilast, cilomilast, diazepam, drotaverine, etazolate, filaminast, glaucine, HT-0712, ibudilast, luteolin, mesembrine, mesembrenone, pentoxifylline, piclamilast, rolipram, roflumilast, RPL-554, GSK256066, chlorbipram, 5-carbamoyl-2-phenylpyrimidine derivatives, ronomilast, MK-0952, MK-0359, MK-0873, KCA-1490, N-(3,5-dichloropyridin-4-yl)-7-methoxy-2-(trifluoromethyl)pyrazolo[1,5-a]pyridine-4-carboxamide, and thalidomide.

PDE-4 degrades cAMP and represents the main PDE isoform in neural tissue and immune cells. PDE-4 inhibitors elevate cAMP, which is envisioned to exert multiple beneficial effects in the context of JNCL. For example, cAMP serves as a potent survival signal for neurons and promotes astrocyte gap junction communication. In addition, PDE-4 inhibitors also display anti-inflammatory effects, which is pertinent to JNCL based on its recognized neuroinflammatory component. For example, low cAMP levels have been implicated in inflammasome activation and IL-1β secretion, and we have shown that CLN3$^{\Delta ex7/8}$ microglia display low cAMP levels at baseline that can be increased with PPF and rolipram, leading to significantly reduced IL-1β release. Finally, PPF has been shown to increase glutamate transporter expression in astrocytes and JNCL is typified by exaggerated glutamate levels in the CNS. Like INI-0602, PPF and rolipram have displayed neuroprotective and anti-inflammatory properties in experimental models of HD, AD, MS, neuropathic pain, SCI, and TBI. Therefore, PDE-4 inhibitors are expected to function well as therapeutics for JNCL based on their ability to target multiple distinct pathways that are dysregulated during JNCL in addition to their proven efficacy in a wide range of CNS diseases. Other advantages are that rolipram and roflumilast are FDA-approved and could be rapidly implemented for off-label use in JNCL patients. Additionally, PPF, rolipram, and roflumilast can be given orally, which is a preferred delivery route, particularly for young children. In addition, evidence continues to emerge in support of common underlying disease mechanisms between lysosomal (i.e., NCLs, Niemann Pick Disease) and lipid storage disorders (i.e., Gaucher disease) with adult-onset neurodegenerative diseases (i.e., PD and AD). Therefore, the target population for both compounds is expected to extend beyond JNCL patients.

All of the studies disclosed herein are performed using $CLN3^{\Delta ex7/8}$ mice, which were engineered to lack a 1.02 kb segment in CLN3 spanning exons 7 and 8. This represents the most common mutation in JNCL patients (80-85%) and therefore, is the most accurate genetic model to assess potential therapeutics to improve disease outcome. Indeed, this is reflected by the fact that $CLN3^{\Delta ex7/8}$ mice faithfully replicate several aspects of JNCL pathology, including neuronal loss, glial activation, glutamate accumulation, and deposition of autofluorescent storage material. Animals are maintained as heterozygous breeders, where WT and $CLN3^{\Delta ex7/8}$ littermates are identified by genotyping and used for experiments in a blinded fashion. Although CLN3 heterozygous mice do not display evidence of storage material accumulation or other disease symptoms, we utilize WT mice instead to limit the number of treatment groups examined.

The methods of the disclosure modulate aberrant glial activation early in the disease process. No studies to date have targeted the functional contributions of glial dysfunction during JNCL. Delivering therapeutics during early stage disease offers an excellent opportunity to delay pathological mechanisms that when chronically activated likely contribute to neuron death. Therapies have been selected which have the ability to affect multiple, distinct processes of glia that we propose are deleterious to neuronal homeostasis when chronically perturbed during JNCL. The complexity of the disease necessitates a strategy to target multiple pathways in order to achieve the greatest impact on disease progression. Although the therapeutics were selected to affect glial dysfunction during JNCL, there is a high likelihood that they will affect other cell types/processes based on the essential nature of the pathways targeted. The experimental design benefits from longitudinal monitoring of the same cohort of animals throughout the treatment period, since repeated MR spectroscopy and behavior measures can provide a window into therapeutic efficacy without the need to sacrifice animals. This methodology allows identification of the optimal interval between treatment initiation and beneficial effects in real time in addition to the duration of such effects, information that cannot be achieved with traditional assessments that require animal sacrifice.

A preclinical study will assess the therapeutic potential of HC inhibitors (e.g., INI-0602) and PDE-4 inhibitors to significantly delay JNCL progression. The fact that both compound classes target multiple, distinct pathways provides for a promising combinational approach to therapy.

Neuroinflammation has been linked to perturbations in astrocyte HC activity, which has been suggested to contribute to neuronal loss[5,6]. Specifically, it has been proposed that dysregulated astrocyte HC function leads to the disruption of homeostatic ion and neurotransmitter gradients via the bidirectional trafficking of molecules through open HCs. As a result, the protective functions of astrocytes are compromised, leading to impaired neuronal physiology and cell death. In support of this concept, recent results from our laboratory have identified aberrant HC activity in brain slices from $CLN3^{\Delta ex7/8}$ mice compared to wild type animals. These changes occur relatively early after birth (i.e., postnatal day 30; P30) and are first evident in the visual and somatosensory barrel field 1 cortices. Interestingly, aberrant HC function becomes more variable one month later (i.e., postnatal day 60; P60) where is remains elevated in the somatosensory barrel field 1 cortex but begins to decline in other brain structures. Therefore, we propose that early inappropriate HC opening contributes to the disruption of homeostatic metabolic gradients contributing to neurodegeneration in JNCL.

Figure 13:
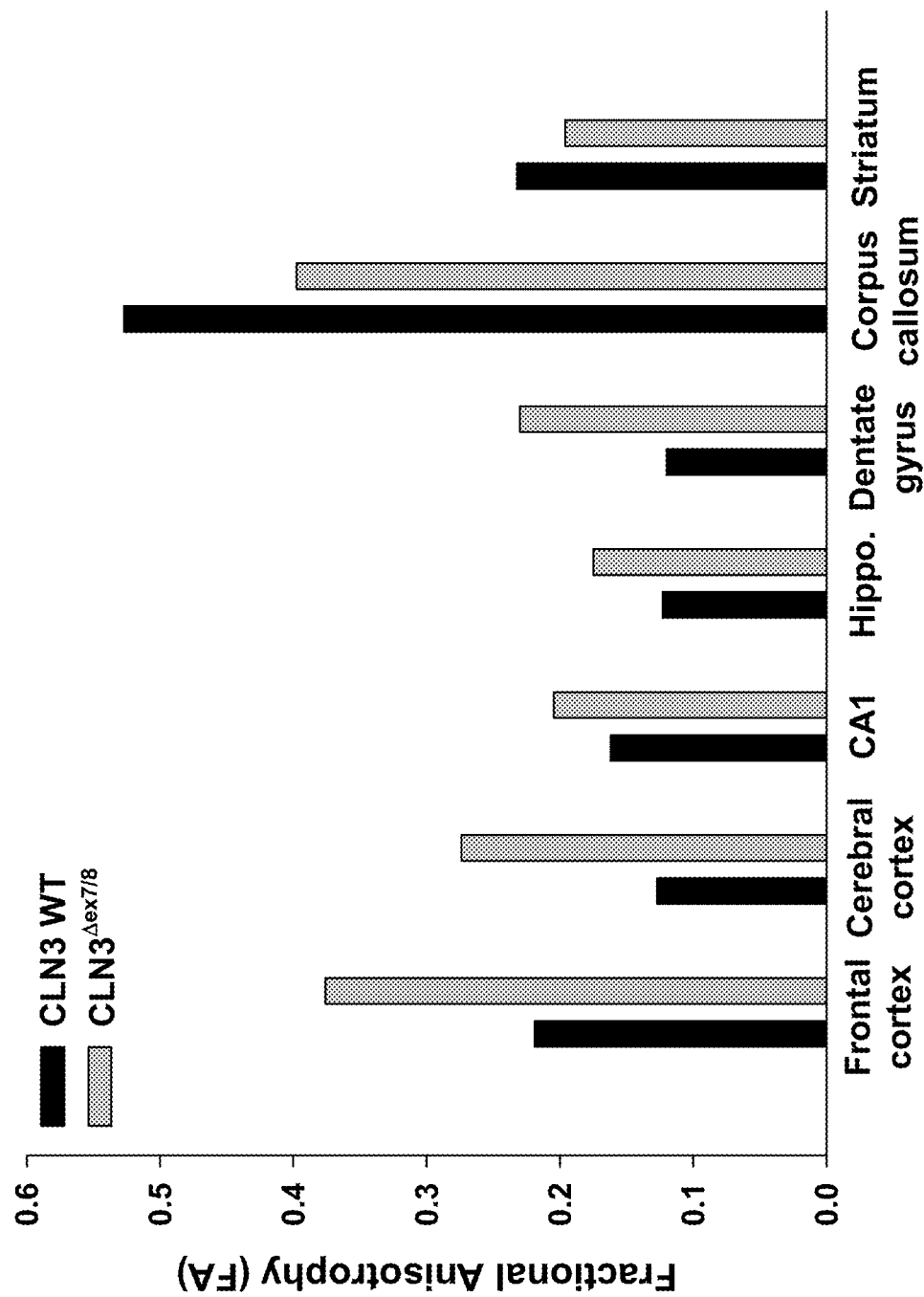
FIG. 13. CLN3$^{\Delta ex7/8}$ mice display DTI abnormalities in both white and grey matter. DTI was utilized to non-invasively analyze CLN3$^{\Delta ex7/8}$ and WT mice at postnatal day 60. Fractional anisotropic measurements of various brain regions are depicted using histograms.
Figure 14:
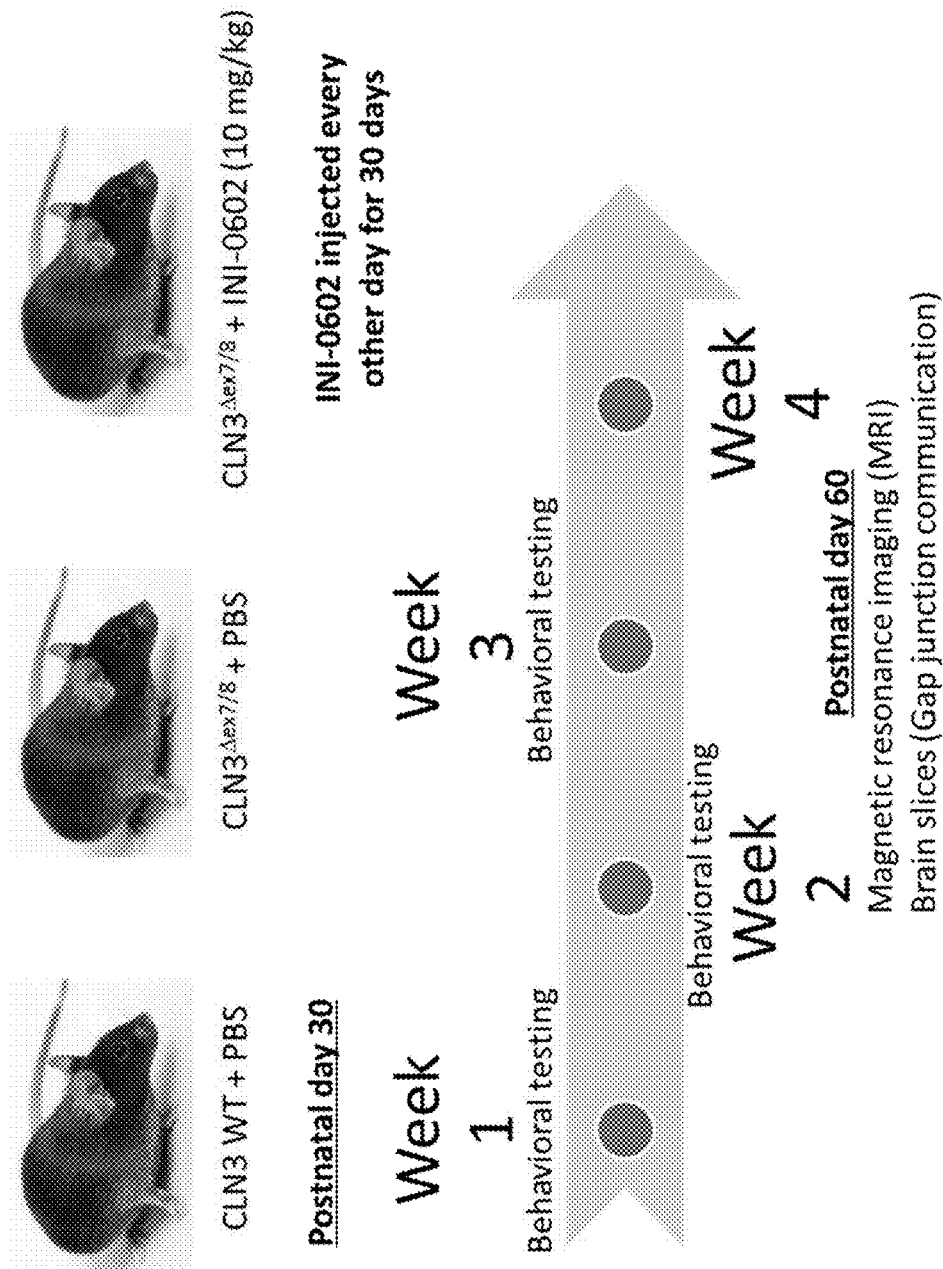
FIG. 14. Schematic illustration of experiments conducted on CLN3$^{\Delta ex7/8}$ and WT mice. CLN3$^{\Delta ex7/8}$ and WT mice received control phosphate-buffered saline or INI-0602 (10 mg/kg every other day). Schematically shown is the weekly behavioral testing interval and both MRI and brain slice analyses for gap junction communication.

Data disclosed herein demonstrates that HC activity is widespread in numerous brain regions within 1 month after birth, which serves as a conduit for glutamate release and heightened extracellular accumulation. Therefore, the inappropriate opening of HCs sets the stage for dysregulation of glutamate levels and may be a significant mechanism for neuronal excitotoxicity during JNCL. Indeed, data from MR spectroscopy analysis of the CNS metabolome has revealed elevated glutamate and glutamine levels in the striatum of $CLN3^{\Delta ex7/8}$ mice as well as additional abnormalities in the hippocampus that coincide with HC opening at P60. Based on the potential for aberrant HC activity to negatively impact neuron survival, it is expected that this mechanism contributes to neurodegeneration during JNCL. Confirming this expectation, young (i.e., P30) $CLN3^{\Delta ex7/8}$ mice are treated with the HC inhibitor, INI-0602[9], to evaluate whether this will restore homeostatic GJC by attenuating aberrant HC opening. The efficacy of this therapeutic intervention is evaluated by monitoring HC and GJC in acute brain slices as well as determining if INI-0602 restores astrocyte electrophysiological parameters in $CLN3^{\Delta ex7/8}$ mice. In addition, the capacity of INI-0602 to improve behavioral deficits associated with early JNCL is assessed by evaluating novel object responses, which has been reported to be an early disease indicator[10] (FIG. 14). MR spectroscopy also is used to determine whether HC blockade returns the abnormal CNS metabolome of $CLN3^{\Delta ex7/8}$ animals to levels reminiscent of WT mice (FIG. 14). Further, since preliminary DTI results have revealed white and grey matter disturbances in $CLN3^{\Delta ex7/8}$ animals, the ability of INI-0602 to reverse these defects is assessed. Because DTI provides measures of water diffusion in the CNS, and GJC/HC activity is linked to osmoregulation, the abnormal DTI measures in the brains of $CLN3^{\Delta ex7/8}$ animals reveal another link between CLN3 mutation and neuropathology (FIG. 13).

Intrinsic defects in microglial and astrocyte activation during early JNCL have been identified using the mouse $CLN3^{\Delta ex7/8}$ model. In particular, $CLN3^{\Delta ex7/8}$ microglia are primed to produce exaggerated levels of numerous proinflammatory mediators (i.e., IL-1β, TNF-α) in response to ceramide and neuron lysates, both of which are elevated in the brains of JNCL patients[3], whereas these stimuli do not trigger activation of wild-type microglia. In addition, our data has shown that $CLN3^{\Delta ex7/8}$ microglia display elevated HC activity that coincides with increased glutamate release. Experimental data also show defects in astrocyte gap junction communication (GJC) concomitant with HC opening in brain slices from young (P30) CLN3$^{\Delta ex7/8}$ mice. Since GJC is a means of homeostatic cellular communication, its inhibition, coupled with HC opening, has the potential to disturb important gradients between the CNS intracellular-extracellular milieus. Therefore, when chronically perturbed, these atypical responses are expected to contribute to neurodegeneration during JNCL. MR spectroscopy data have identified early perturbations in the metabolic profile of numerous brain regions in CLN3$^{\Delta ex7/8}$ mice in addition to white and grey matter damage revealed by Diffusion Tensor Imaging (DTI). Because aberrant HC activity is common to both CLN3$^{\Delta ex7/8}$ microglia and astrocytes, and is a driving force to disrupt normal brain homeostasis and impinge on all of these pathological responses, it is expected that the pharmacological targeting of HC function will restore normal cellular communication networks within the CNS to enhance the survival of JNCL patients. It is envisioned that blocking aberrant glial HC activity during early JNCL will prolong neuronal survival, resulting in delayed disease progression and improvements in quality of life.

Our studies with the PDE-4 inhibitors propentofylline, rolipram, and roflumilast have revealed that these compounds are able to selectively block proinflammatory mediator release from primary microglia isolated from CLN3$^{\Delta ex7/8}$ mice (i.e., IL-1β, TNF-α) and this effect, in concert with the reported ability of propentofylline to augment glutamate transporter expression on astrocytes, suggests that PDE-4 inhibitors hold great promise as a novel treatment for delaying neuronal loss during JNCL. Ultimately, these therapies are aimed at significantly delaying neuron death, resulting in improvements in quality of life for children suffering from this devastating neurodegenerative disease.

Our recent studies have identified intrinsic defects in microglial and astrocyte activation during early JNCL using the mouse CLN3$^{\Delta ex7/8}$ model. In particular, CLN3$^{\Delta ex7/8}$ microglia are primed to produce exaggerated levels of numerous proinflammatory mediators (i.e., 1L-1β, TNF-α.) in response to ceramide and neuron lysates, both of which are elevated in the brains of JNCL patients, whereas these stimuli do not trigger activation of wild-type microglia. In addition, our preliminary data has shown that CLN3$^{\Delta ex7/8}$ microglia display elevated HC activity that coincides with increased glutamate release. We have also shown astrocyte HC opening in brain slices from young (P30) CLN3$^{\Delta ex7/8}$ mice. This HC opening has the potential to disturb important gradients between the CNS intracellular-extracellular milieus. Therefore, when chronically perturbed, these atypical responses likely contribute to neurodegeneration during JNCL. Because aberrant HC activity is common to both CLN3$^{\Delta ex7/8}$ microglia and astrocytes and is a driving force to disrupt normal brain homeostasis and impinge on all of these pathological responses, we propose that the pharmacological targeting of HC function will restore normal cellular communication networks within the CNS to enhance the survival of JNCL patients.

Prior mass spectrometry studies of samples from the brains of JNCL patients have identified several perturbations in the CNS metabolome. In particular, the disease is associated with elevated glutamate levels, which is thought to contribute to neuronal excitotoxicity. Astrocytes play a major role in maintaining glutamate concentrations through glutamate transporters and GJC. Data disclosed herein demonstrate that HC activity is widespread in numerous brain regions, which serves as a conduit for glutamate release and heightened extracellular accumulation. Therefore, the inappropriate opening of HCs sets the stage for dysregulation of glutamate levels and may be a significant mechanism for neuronal excitotoxicity during JNCL.

Figure 15:
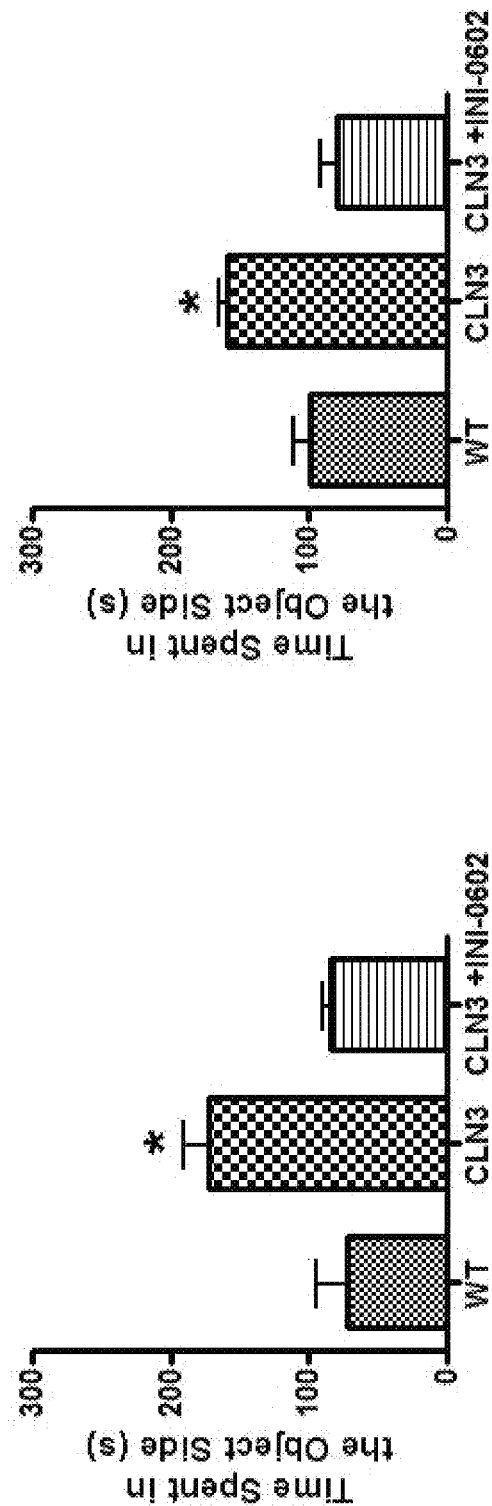
FIG. 15. INI-0602-induced restoration of WT behaviors to CLN3$^{\Delta ex7/8}$ mice. Mice received i.p. injections of INI-0602 (10 mg/kg) or vehicle (PBS) every other day beginning at postnatal day 30 and continuing until postnatal day 60. Mice were subjected to novel object recognition at weekly intervals. Graphs depict the length of time that animals spent in the side of the cage that contained the novel object. CLN3 mutant mice spent significantly more time investigating the novel object (i.e., perseverance) at weeks 1 (left) and 2 (right) after treatment, which was reduced to levels typical of WT animals following INI-0602 treatment.

To assess the impact of aberrant HC activity during JNCL, we treated CLN3$^{\Delta ex7/8}$ mice with the blood-brain-barrier-permeable HC inhibitor, INI-0602, for a 30 day period (10 mg/kg i.p., once every two days) beginning at postnatal day 30 and continuing until postnatal day 60. Novel object testing was performed at weekly intervals throughout the 30-day study and animals weights monitored. At the end of the treatment period, mice were subjected to MR spectroscopy (to measure brain metabolites) and DTI (to monitor parenchymal damage) as well as monitoring the extent of GJC and HC activity in acute brain slices. We found that INI-0602 reduced behavioral abnormalities in CLN3$^{\Delta ex7/8}$ mice and restored elevated glutamate levels in the hippocampus and striatum to values typical of wild-type animals (FIG. 15). This coincided with a dramatic increase in the extent of GJC within the neocortex and hippocampus. INI-0602 did not show any evidence of toxicity during the one-month treatment interval (as determined by weight and blood chemistry profiles). Therefore, INI-0602 appears to reverse several pathological responses that have been implicated in neuronal loss during JNCL and may represent a novel treatment approach to delay symptom progression in children with this devastating disease and improve quality of life.

In separate studies, we have also demonstrated that propentofylline, rolipram, and roflumilast inhibit the expression of select inflammatory cytokines, including TNF-α and IL-1β, in CLN3$^{\Delta ex7/8}$ microglia, indicating it has beneficial effects in the JNCL brain. The reported ability of propentofylline to augment glutamate transporter expression in astrocytes is expected to provide synergistic benefits with its ability to attenuate microglial activation, which together is expected to provide therapeutic benefits by targeting multiple pathological pathways.

There is no cure for children suffering from JNCL and the few therapeutics that are currently available are used to counter side-effects of the disease (e.g., seizures, behavioral issues). Therefore, there is a need to identify treatment approaches to slow/halt disease progression and neuronal loss to provide improvements in quality-of-life for children suffering from this deadly disease. Our approach to therapy is innovative, since it is designed to address pathological mechanisms that are apparent during early disease (i.e., day 30) and significantly pre-date later intervals when neuron loss is evident (i.e., 5-7 months). Therefore, targeting these aberrant responses may significantly delay disease progression, which could conceivably prevent neuronal death. Indeed, chronic microglial proinflammatory activation and aberrant astrocyte homeostasis are likely contributors to neuronal demise during disease. These pathways are reversed by PDE-4 inhibitors (propentofylline, rolipram, and roflumilast) and 1NI-0602, which represents the first demonstration of beneficial effects by targeting glial activation in Juvenile Batten Disease.

A final note to emphasize is that both PDE-4 inhibitors (propentofylline and rolipram) and 1NI-0602 have been shown to exert neuroprotective effects in other mouse models (e.g., neuropathic pain, Alzheimer's Disease, ALS); therefore, although Juvenile Batten Disease is a relatively rare disorder, our studies support the concept of linking the use of these drugs across a spectrum of neurodegenerative disorders. The disclosure represents the first demonstration of beneficial effects of either compound class on JNCL pathology.

The advantage of our invention is that it targets pathways that we believe lie at the foundation of the disease. By selecting agents that affect these basic physiologic pathways, we have the greatest chance to significantly slow neuron loss and disease progression that is not afforded by any currently available therapy. In particular, our supporting data demonstrates that hemi-channel blockers, such as INI-0602, are capable of restoring the CNS environment towards a more physiologic state by reducing extracellular glutamate levels and increasing cell-cell cross-talk (gap junction communication) that is well-recognized for its role in neuronal homeostasis. In addition, PDE4 inhibitors, such aspropentofylline, rolipram, and roflumilast, are capable of selectively blocking the production of key proinflammatory mediators from JNCL microglia that, over time, can contribute to neuron toxicity and death. Therefore, this may represent another therapeutic target for JNCL.

The disclosure establishes, in part, and supports the expectation that loss of CLN3 function leads to intrinsic microglial dysfunction, causing elevated production of oxidative mediators via mitochondrial dysfunction that trigger inflammasome activation, IL-1β secretion, and subsequent neuronal cell death. Data supporting the expectation is obtained by determining whether CLN3 loss leads to imbalances in microglial oxidative pathways that trigger inflammasome activity, particularly with regard to mitochondrial dysfunction, contributing to neuronal cell death. These studies are expected to reveal whether CLN3 loss results in aberrant microglial inflammasome activation in response to mediators that are elevated in the brains of Juvenile Batten Disease patients; to indicate whether CLN3 loss impairs microglial mitochondrial oxidative balance; and to disclose how CLN3 loss impacts the interplay between microglia and neurons using a co-culture paradigm.

Experiments are conducted to examine whether CLN3 deficiency leads to perturbations in homeostatic modes of cellular communication in living brain slices. These experiments examine the effects of CLN3 deficiency on (a) gap junction communication (GJC) and (b) hemi-channel (HC) activity in acute brain slices. Both modes of communication are important for preventing the accumulation of excitotoxic molecules in the extracellular milieu[15,16], many of which are elevated in the brains of Juvenile Batten Disease patients. In addition, because microglia have been shown to directly modify GJC/HC activity[17-19], changes in GJC and/or HC activity in CLN3$^{\Delta ex7/8}$ brain slices will be examined to determine if they are associated with microglia that are polarized to a proinflammatory M1 phenotype rather than a neuroprotective M2 phenotype[20]. Also, pharmacological approaches to manipulate ROS/inflammasome activity in CLN3$^{\Delta ex7/8}$ brain slices are explored to evaluate whether GJC/HC activity is restored to physiological levels.

Activated microglia and astrocytes are observed in the brains of Juvenile Batten disease patients as well as associated mouse models (i.e., CLN3 knockout and CLN3$^{\Delta ex7/8}$ mice that harbor the 1.0 kb deletion in CLN3 that affects the majority of JNCL patients)[4,5], and these areas of the brain are predictive of neurodegeneration. Studies with CLN3 knockout mice have revealed a correlation between activated microglia and areas of neuronal damage[4,5].

CLN3$^{\Delta ex7/8}$ microglia exist in a primed state and produce numerous proinflammatory mediators in response to endogenous "danger signals" (i.e., ceramide and neuronal lysate) with known neurotoxic effects, whereas wild type (WT) cells are relatively non-responsive. Astrocyte reactivity is also altered, with enhanced hemi-channel (HC) activity observed in numerous brain regions of CLN3$^{\Delta ex7/8}$ mice as early as postnatal day 30. Under typical physiological conditions, astrocyte HCs are closed to prevent the non-discriminant diffusion of molecules from the intra- to extracellular milieus. Instead, HCs from adjacent astrocytes join to form intercellular gap junction channels that are involved in regulating extracellular glutamate levels, glucose transfer, and pH/ion homeostasis. Therefore, the combination of early HC opening and aberrant microglial activation in JNCL likely disrupts the brain metabolome, triggering the pathological chain of events that culminate in neuronal loss. This possibility is supported by our preliminary data demonstrating increased glutamate and decreased GABA levels in the hippocampus and striatum of young CLN3$^{\Delta ex7/8}$ mice, which is also observed in JNCL patients.

In addition, microglial activation precedes evidence of neuronal degeneration[4], indicating that microglia may impact JNCL progression. The data disclosed herein establishes that numerous inflammatory pathways are triggered in microglia and astrocytes during the early postnatal period in CLN3$^{\Delta ex7/8}$ mice. It is also well-appreciated that chronic inflammatory responses within the CNS are deleterious to neuronal survival. Based on these observations, it is expected that pharmacologically targeting early aberrant glial activation will delay JNCL progression.

Little information is known about the interplay between activated microglia and neurons in the context of JNCL. Understanding whether CLN3 loss leads to intrinsic defects in microglial activation and how this affects neuronal survival will identify pathological mechanisms that are expected to be excellent therapeutic targets for improving the life expectancy of these children. This is particularly relevant given the existence of approved pharmaceuticals that target oxidative pathways and regulate IL-1β action.

Figure 1:
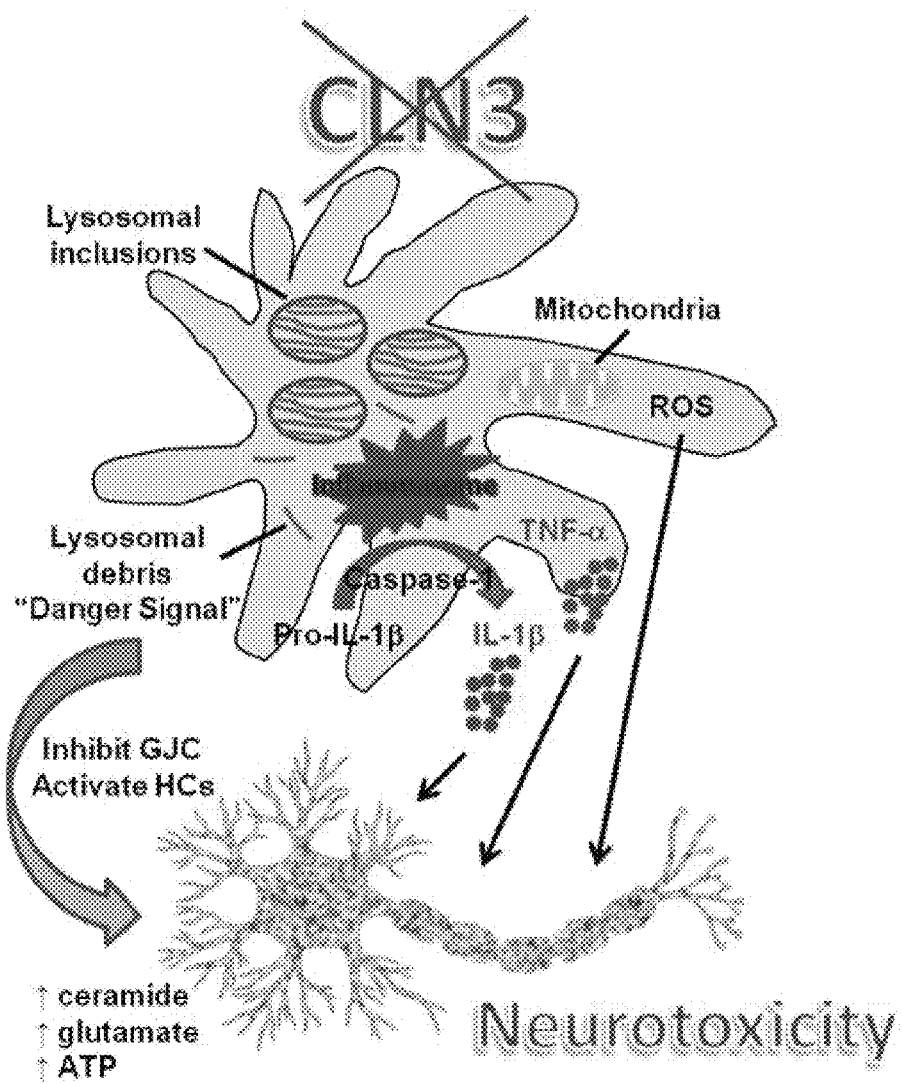
FIG. 1. Mechanism for microglial dysfunction and neuron death during JNCL. Loss of normal CLN3 function leads to the formation of lysosomal inclusions that liberate "danger signals", triggering inflammasome activation and IL-1β processing. Reactive oxygen species (ROS) are also elicited by danger signals along with other proinflammatory cytokines (i.e., TNF-α). These inflammatory mediators stimulate hemi-channel (HC) activity, which leads to enhanced extracellular accumulation of glutamate, ATP, and ceramide, which are increased in Juvenile Batten Disease brains. All of these mechanisms stemming from CLN3 mutation converge to compromise neuron survival.

There is no published information currently available regarding whether CLN3 affects microglial function. Based on the ability of microglia to affect neuronal activity and CNS homeostasis, it is expected that microglial dysfunction following CLN3 loss contributes to neurodegeneration in JNCL. It is expected that oxidative pathways and inflammasome activity are elevated in CLN3-deficient microglia, which are expected to contribute, in part, to neuronal loss in JNCL (FIG. 1). It is important to note that microglial dysfunction is not proposed as the sole mechanism responsible for neuronal loss during JNCL, however the fact that microglia affect numerous physiological processes in the normal CNS makes these cells an attractive candidate to study their role in disease progression. In addition, the studies disclosed herein incorporate techniques that have not been extensively utilized in the field. First, co-culture experiments with primary microglia and neurons provide a more direct means to investigate cross-talk between both populations in the context of CLN3 loss without confounding interference from additional cell types. However, in order to identify key mechanisms that are aberrantly regulated during JNCL, scenarios where the complete repertoire of cell types is preserved are also investigated. This is accomplished using living brain slices to study how CLN3 loss impacts normal intercellular communication. No studies to date have examined the impact of CLN3 deficiency on cellular communication via gap junctions or hemi-channels, each of which plays a role in maintaining the extracellular milieu to preserve neuronal integrity and function[15].

Example 1

Effect of CLN3 Loss on Microglial Oxidative Pathway Balance and Inflammasome Activity Microglial activation has been implicated in the pathogenesis of several neurodegenerative diseases (e.g., Alzheimer's Disease) and inflammatory disorders (e.g., multiple sclerosis)[20]. An earlier study reported morphological indices of microglial activation in CLN3-deficient mice that significantly preceded neuronal loss[5]. These studies only performed immunostaining analysis and therefore, functional attributes of activated microglia in the context of CLN3 loss were not examined. This is significant, since it is well appreciated that an "activated" morphology cannot predict whether microglia possess pro- or anti-inflammatory properties. These studies will assess whether loss of CLN3 function leads to intrinsic microglial dysfunction, causing elevated production of oxidative mediators that trigger inflammasome activation, IL-1β secretion, and subsequent neuronal cell death.

Primary microglia from CLN3$^{\Delta ex7/8}$ (on a C57BL/6 background) and WT mice at various ages (postnatal days 2, 30, and 60) are procured to investigate whether progressive changes in microglial proinflammatory activity can be discerned, is expected to translate into less neuronal protection over time as JNCL progresses. This approach allowed identification of potential therapeutic targets that would interfere with neuronal loss at the earliest stages possible following a child's diagnosis of JNCL. Because of technical issues relating to cell survival, primary neurons can only be procured from embryonic mice at gestational day 16 (E16). Therefore, any age-dependence in sensitivity with regard to CLN3$^{\Delta ex7/8}$ neurons following microglial exposure cannot be investigated. Initial studies are conducted with cortical neurons. The studies examine both microglia in isolation following exposure to various mediators whose expression is elevated in the Juvenile Batten Disease brain, as well as microglia-neuron co-cultures. In the co-culture model, wild-type (i.e., WT) microglia are incubated with CLN3$^{\Delta ex7/8}$ neurons and vice versa, in addition to culturing both WT cell types and both CLN3$^{\Delta ex7/8}$ cell types. This combinational approach allows for a determination of whether microglia are the dominant drivers of neuronal cell death in the context of CLN3 loss or whether defects are intrinsic to neurons.

CLN3 loss is examined to determine if the loss results in aberrant microglial inflammasome activity in response to molecules that are elevated in the brains of Juvenile Batten Disease patients. Studies have shown increased levels of numerous molecules, including glutamate, ceramide, and ATP, in the brains of children with Juvenile Batten Disease as well as in CLN3-deficient mice[22-24]. The prolonged elevation of these molecules is not compatible with neuronal survival, which may represent a contributing factor to JNCL. In particular, it is expected that these molecules induce a pathological cascade, whereby exaggerated mitochondrial reactive oxygen species (i.e., ROS) production triggers inflammasome activation, IL-1β production, and neuronal cell death (FIG. 1).

Example 2

Glutamate Effect on Proinflammatory Mediators

Primary microglia procured from CLN3$^{\Delta ex7/8}$ mice are examined to determine if they display elevated proinflammatory mediator expression compared to WT cells following exposure to glutamate, ceramide, and ATP, as well as lysates from primary neurons. The latter is a relevant stimulus that mimics neuronal loss that occurs during Juvenile Batten Disease, whereby microglia are exposed to cellular debris as a part of their phagocytic scavenging function.

Figure 2:
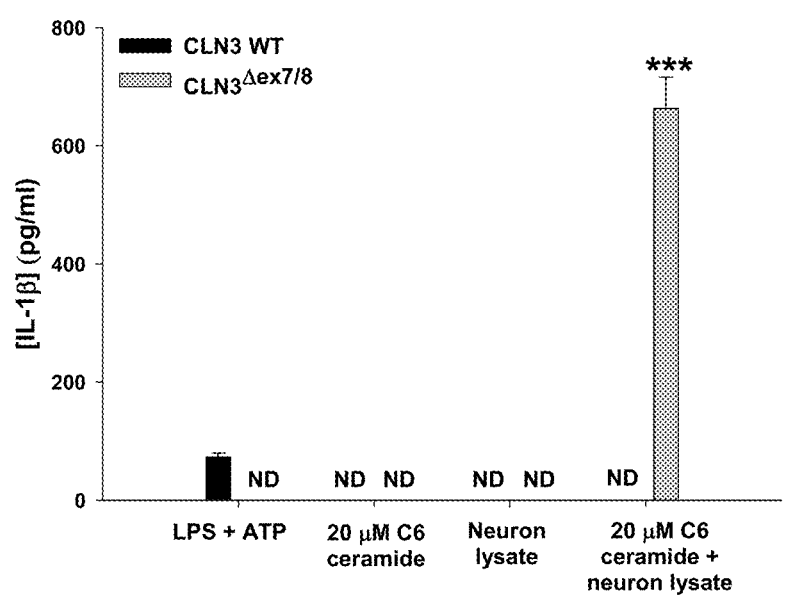
FIG. 2. IL-1β release is enhanced in CLN3$^{\Delta ex7/8}$ microglia. Primary microglia isolated from wild-type (WT) or CLN3$^{\Delta ex7/8}$ mice (postnatal day 2) were treated with 100 ng/ml LPS+5 mM ATP; 10 µg/ml C6 ceramide, and primary neuronal lysates either alone or in combination for 24 hours, whereupon IL-1β production was quantitated by ELISA. Results represent the mean±S.D. of three independent replicates (*, $p<0.05$).
Figure 3:
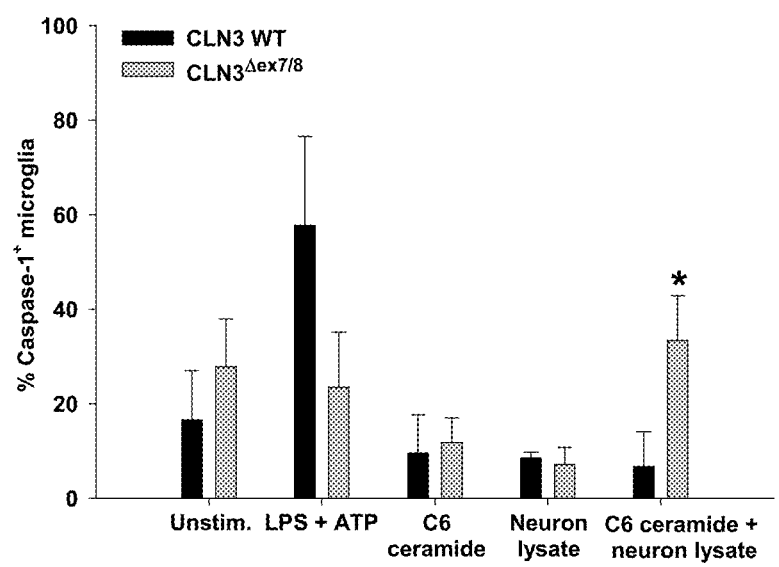
FIG. 3. Increased caspase-1 activation in CLN3$^{\Delta ex7/8}$ microglia. Primary CLN3$^{\Delta ex7/8}$ or WT microglia (postnatal day 2) were treated with 100 ng/ml LPS+5 mM ATP; 10 µg/ml C6 ceramide, and primary neuronal lysates either alone or in combination for 6 hours, whereupon caspase-1 activation was quantitated by FACS using the FLICA reagent (Immunochemistry Technologies LLC).
Figure 4:
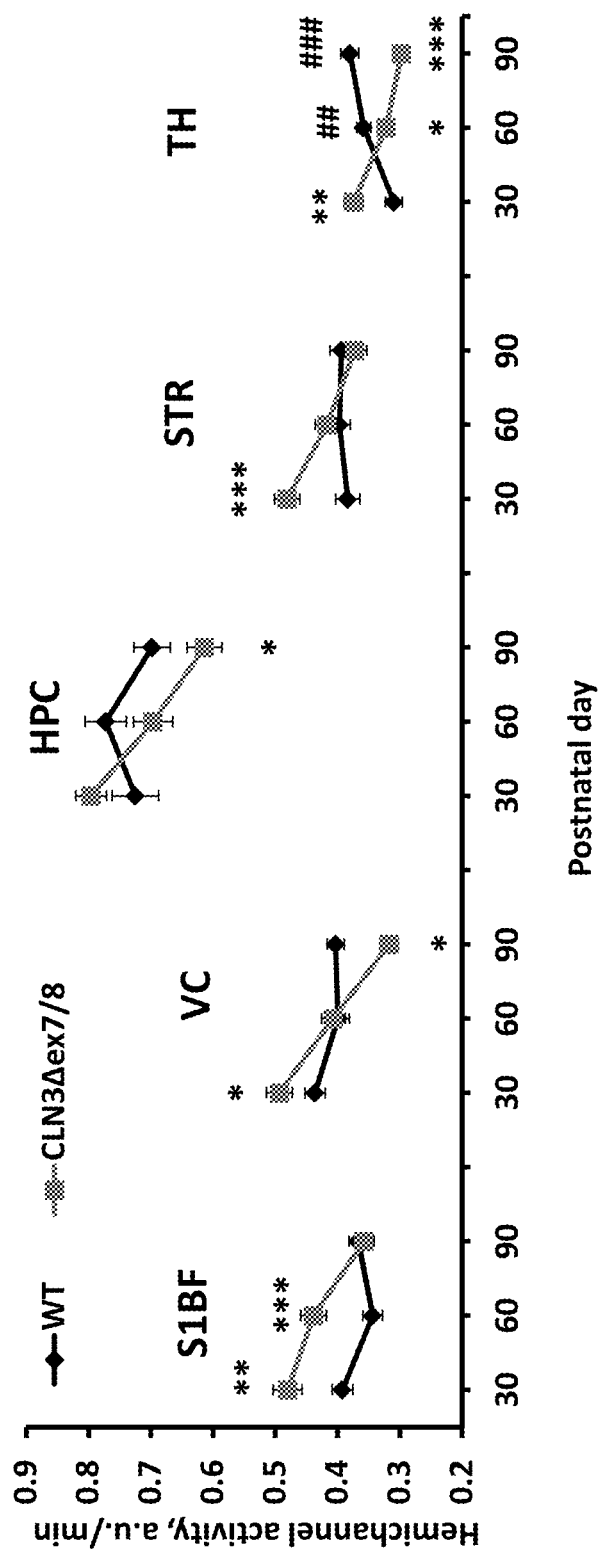
FIG. 4. CLN3$^{\Delta ex7/8}$ astrocytes display early aberrant hemi-channel activity in a region-dependent manner. Acute brain slices were prepared from CLN3$^{\Delta ex7/8}$ and WT mice, whereupon hemi-channel activity was measured by ethidium bromide (EtBr) uptake. Significant differences between CLN3$^{\Delta ex7/8}$ and WT slices are denoted by asterisks (*, $p<0.05$; , $p<0.01$; *, $p<0.001$), whereas changes in each mouse strain compared to day 30 are indicated by hatched signs (##, $p<0.01$; ###, $p<0.001$). S1BF, somatosensory barrel field 1 cortex; VC, visual cortex; HPC, hippocampus; STR, striatum; TH, thalamus.

In these experiments, primary microglia are isolated from the brains of CLN3$^{\Delta ex7/8}$ and WT mice[8,25-27]. Microglia are exposed to previously optimized concentrations of glutamate (50 μM), ATP (5 mM), ceramide (20-100 μM), neuronal lysate (1:2 or 1:5 dilution), or LPS+ATP as a positive control (100 ng/ml and 5 mM, respectively) for 24 hours, whereupon interleukin-1β (IL-1β) and tumor necrosis factor-α (TNF-α) expression are quantitated by ELISA. These cytokines were selected for analysis because they have been directly implicated in contributing to microglia-induced neuronal cell death[14,28] and also because they intersect with oxidative pathways described herein. Interestingly, the studies disclosed herein demonstrate that IL-1β release is decreased in CLN3$^{\Delta ex7/8}$ microglia compared to WT cells in response to LPS+ATP (FIG. 2), indicating that CLN3 normally functions to control inflammasome activation. In addition, CLN3 loss is examined to determine if the loss augments caspase-1 activity, a key inflammasome component that senses oxidative stress and lysosomal damage, resulting in IL-1β cleavage and secretion by microglia[8]. Here, CLN3$^{\Delta ex7/8}$ and WT microglia are exposed to the same stimuli described above, followed by incubation with the FLICA reagent (Immunochemistry Technologies LLC), a caspase-1 substrate that emits fluorescence when cleaved by the active enzyme[29]. IL-1β and TNF-α production, as well as caspase-1 activity, are enhanced in CLN3$^{\Delta ex7/8}$ microglia in response to JNCL stimuli (i.e., ceramide+neuronal lysate) compared to WT cells, revealing the failure to appropriately regulate cytokine production in the context of CLN3 loss (FIGS. 21-22). Indeed, studies support this expectation because caspase-1 activity was elevated in CLN3$^{\Delta ex7/8}$ microglia compared to WT cells (FIG. 3).

Example 3

CLN3 Effect on Progressive Oxidative Damage

CLN3 loss is investigated to determine if it leads to impaired oxidative balance. Studies have revealed that CLN3 loss leads to progressive oxidative damage[12,13], and increased oxidative stress has recently been shown to trigger inflammasome activation and subsequent IL-1β cleavage in macrophages[11]. Therefore, a precedent exists for linking CLN3, oxidative stress, and cytokine production. First, reactive oxygen (ROS) and reactive nitrogen (RNI) species production by CLN3$^{\Delta ex7/8}$ and WT microglia are compared under baseline conditions as well as following exposure to stimuli that are elevated in the brains of Juvenile Batten Disease patients, including glutamate, ceramide, ATP, and neuronal lysate[22-24]. It is expected that aberrant mitochondrial ROS production may lead to the dysregulation in inflammasome activity in CLN3$^{\Delta ex7/8}$ microglia, which is supported by the fact that other studies have reported mitochondrial defects in neurons from CLN3$^{\Delta ex7/8}$ mice. It is notable that ceramide also increased caspase-1 activation in CLN3$^{\Delta ex7/8}$ microglia (FIG. 3), again supporting a link between the inflammasome (via caspase-1) activation and ROS production. Because cellular oxidative balance is dictated by the net levels of pro- and anti-oxidant molecules, the expression of the latter is also quantitated to complement the studies described above with pro-oxidants. Specifically, total glutathione (GSH) production in CLN3$^{\Delta ex7/8}$ and WT microglia[12] is examined to determine whether the former exhibits GSH depletion upon stimulation that may account for exacerbated reactive oxygen/nitrogen radical production. In addition, superoxide dismutase (SOD) expression is examined in CLN3$^{\Delta ex7/8}$ and WT microglia, where it is expected that the former will express reduced SOD levels that coincide with the inability to handle oxygen free radicals. Experiments are also designed and performed to determine whether altered oxidation status in microglia extends to changes in mitochondrial membrane potential. This is particularly relevant given that the inflammasome senses mitochondrial dysfunction in macrophages leading to IL-1β release[11]. In these studies, CLN3$^{\Delta ex7/8}$ and WT microglia are exposed to the same stimuli identified above, whereupon mitochondrial membrane potential is examined using three types of mitochondria-specific labels that distinguish respiring (Mitotracker deep red), total (Mitotracker green), and ROS-generating mitochondria (MitoSOX)[11].

Example 4

Mutant Microglial Sensitivity to Oxidative Stress

The sensitivity of CLN3$^{\Delta ex7/8}$ microglia to oxidative stress is also examined, because it has been reported that CLN3 mutant Drosophila were less capable of handling oxidative damage[13]. In these experiments, CLN3$^{\Delta ex7/8}$ and WT microglia are treated for 3, 6, 12, or 24 hours with three compounds that alter oxidative balance, namely $H_2O_2$ that generates hydroxyl radicals via the Fenton reaction; diethylmaleate that depletes cellular glutathione; and paraquat, which generates superoxide anions[13]. Microglial viability is assessed by LDH release assays and the ability of oxidative intermediates to trigger cytokine production (TNF-α and IL-1β) is determined by ELISAs. Based on studies demonstrating the impaired ability of CLN3 mutant Drosophila to adapt to oxidative stress, CLN3$^{\Delta ex7/8}$ microglia are expected to display increased proinflammatory mediator release triggered by elevated oxygen radicals, culminating in cell death. Dysregulated microglial activity via oxidative imbalance is expected to represent one effector mechanism contributing to neuronal cell death during JNCL (FIG. 1).

Example 5

Effect of CLN3 Loss on Microglial-Neuron Interactions

CLN3 loss is expected to affect the interplay between microglia and neurons using a co-culture paradigm. There is considerable experimental evidence that activated microglia can negatively impact neuron survival[6,10]. In the context of JNCL, a study in CLN3-deficient mice revealed the close apposition of activated microglia to neurons that express MnSOD, an antioxidant enzyme that converts superoxide to $H_2O_2$[12]. Without wishing to be bound by theory, CLN3-deficient microglia could produce elevated superoxide levels that trigger MnSOD expression in neighboring neurons in an attempt to protect the latter from oxidative damage. In these studies, co-cultures of WT microglia with neurons from CLN3$^{\Delta ex7/8}$ mice or vice versa are established to determine the interplay between both populations in terms of CLN3 deficiency. WT microglia-neuron and CLN3$^{\Delta ex7/8}$ microglia-neuron co-cultures serve as controls for comparison with mixed co-cultures. Co-cultures are either untreated or exposed to glutamate, ceramide, or ATP for 24-72 hours, whereupon the impact of CLN3 on neuronal integrity is examined by immunofluorescence staining for microtubule-associated protein-2 (MAP-2). Experiments are also performed that rely on immunofluorescence staining for activated caspase-3 as an indicator of apoptosis in conjunction with Iba-1 and MAP-2 to differentiate apoptotic microglia from neurons, respectively. Increased neuronal cell death in either WT or CLN3$^{\Delta ex7/8}$ neurons cultured with CLN3$^{\Delta ex7/8}$ microglia is expected, revealing a dominant role for microglial activation in dictating neuron death. However, it is also possible that maximal cell death will be observed with CLN3$^{\Delta ex7/8}$ microglia-CLN3$^{\Delta ex7/8}$ neuron cultures due to the additive effects of exaggerated free radical and proinflammatory cytokine release from microglia coupled with impaired intrinsic antioxidant properties of neurons.

Example 6

Roles of Reactive Oxygen and Cytokines in Neuronal Death

To demonstrate the functional role of ROS/cytokines in mediating neuronal death, these mediators are blocked using pharmacological inhibitors and/or neutralizing antibodies (Abs). Analyses are limited to those mediators whose release is increased in CLN3$^{\Delta ex7/8}$ microglia as determined by experiments disclosed herein. It is expected that interfering with ROS or cytokine production by CLN3$^{\Delta ex7/8}$ microglia will attenuate the extent of neuronal cell death in co-cultures. Establishing a role for ROS and/or cytokines in mediating neuronal death provides the benefit of using known inhibitors of these pathways as therapeutic interventions for JNCL.

Example 7

CLN3 Loss Leads to Perturbations in Homeostatic Modes of Intercellular Communication Important to CNS homeostasis are cellular networks formed by gap junctions, which play a significant role in maintaining extracellular pH, $K^+$, and glutamate levels[15]. Gap junction channels are formed by the joining of two hemi-channels (HCs) from adjacent cells[16], and it was recently demonstrated that HCs can be opened during pathological conditions[21,31]. In addition, activated microglia have been shown to inhibit gap junction communication (GJC) and stimulate HC activity[18,19]. If CLN3 loss leads to a proinflammatory microglial phenotype, it is expected that this would affect GJC/HC activity and represent another mechanism responsible for neuronal dysfunction during JNCL. This is significant because GJ/HC activity has been shown to regulate extracellular glutamate, which is elevated in the brains of Juvenile Batten Disease patients[24]. However, no studies have yet been performed to investigate whether CLN3 deficiency leads to aberrant cellular communication[21,32]. For these experiments, acute brain slices procured from CLN3$^{\Delta ex7/8}$ and WT mice at various ages (postnatal days 30, 60, and 90) are used to investigate whether changes in GJC and HC activity can be discerned, which is evidence of a contribution to the progressive neuronal cell loss associated with JNCL.

The effect of CLN3 loss on GJC and HC activity in living brain slices is examined, as previously described[21]. Briefly, CLN3$^{\Delta ex7/8}$ and WT mice are euthanized by cervical dislocation and immediately decapitated, whereupon the brain is quickly removed and bathed in ice-cold artificial cerebrospinal fluid (ACSF) buffered with carbogen (95% $O_2$ and 5% $CO_2$). Next, horizontal brain slices (300-400 μm thick) are cut using a vibrating blade microtome and held in ACSF containing CellTracker Blue dye to facilitate cell identification. Whole-cell patch-clamp recordings are performed on individual cells in CLN3$^{\Delta ex7/8}$ or WT brain slices, where the GJ-permeable dye Alexa Fluor 360 is added to the intracellular recording solution to evaluate the degree of cell coupling. The distance of dye spread from a single microinjected cell to neighboring cells can be quantitated and is reflective of the extent of GJC. Because activated microglia have been shown to attenuate GJC[17,18], it is expected that GJC is reduced in CLN3$^{\Delta ex7/8}$ brain slices, which would corroborate the findings of enhanced ROS and IL-1β production by CLN3$^{\Delta ex7/8}$ microglia. This would represent another mechanism whereby CLN3 deficiency contributes to neuronal cell death, since GJC is important for detoxification of the extracellular milieu. Most relevant to Juvenile Batten Disease is the ability of GJC to dilute glutamate. Therefore, if CLN3 loss prevents glutamate uptake and elimination via GJC, this would result in excessive extracellular glutamate concentrations and neuron excitotoxicity, both of which are observed in the brains of Juvenile Batten Disease patients.

To evaluate hemi-channel (HC) activity, ethidium bromide (EtBr; 2.5 μM) is added to the bath solution during brain slice preparation, as previously described[21]. EtBr has a small molecular weight that enables its uptake into cells when HC are open. It is thought that open HCs are deleterious to brain homeostasis, since this would allow for the disruption of physiologic gradients between the intra- and extracellular milieus[33,34]. In addition, studies have revealed that inflammation results in the opening of HCs in the brain[21], which agrees with reports where activated microglia induced HC activity[19]. Therefore, it is expected that significant baseline HC activity in brain slices of CLN3$^{\Delta ex7/8}$ mice will be observed due to aberrant microglial activation. In addition, proinflammatory mediators, such as IL-1β and TNF-α released from activated microglia, have been shown to induce hemi-channel activity and glutamate release[28]. Therefore, it is possible that by virtue of their inherent proinflammatory activity that activated microglia lead to neuronal toxicity not only by releasing proinflammatory cytokines and oxidative mediators but also by releasing glutamate via aberrant hemi-channel activity. This scenario links the experiments described in this Example and in the preceding Example, and is supported by the fact that Juvenile Batten Disease is associated with widespread metabolic disruptions and elevated extracellular concentrations of numerous metabolites[24]. If the experiments described herein reveal heightened ROS/cytokine production by CLN3$^{\Delta ex7/8}$ microglia, CLN3$^{\Delta ex7/8}$ brain slices will be treated with ROS inhibitors or cytokine neutralizing antibodies to determine whether this will restore aberrant GJC/HC activity to WT levels. Relevant here is that pharmacological agents exist to modify GJC/HC activity as well as ROS and cytokine actions. Therefore, all of these effectors are expected to exhibit therapeutic efficacy in bestowing increased neuronal survival in CLN3$^{\Delta ex7/8}$ mice.

Example 8

Effect of CLN3 Mutants on Gap Junction Communication and Hemi-Channel Activity

Because microglia have been shown to directly modify GJC/HC activity, changes in GJC and/or HC activity in CLN3$^{\Delta ex7/8}$ brain slices will be assessed for any association with microglia that are polarized to a proinflammatory M1 phenotype rather than a neuroprotective M2 phenotype[20]. Primary microglia are isolated from CLN3$^{\Delta ex7/8}$ and WT mice, whereupon activation phenotypes are evaluated by FACS using well-described markers for proinflammatory M1 (iNOS, IRF-5, IL-12, and CD40) and anti-inflammatory M2 microglia (arginase-1, Ym-1, and CD206). It is expected that microglia recovered from CLN3$^{\Delta ex7/8}$ mice will be biased towards a pro-inflammatory M1 phenotype that will correspond with impaired GJC and open HCs in brain slices from these animals. This would agree with the current consensus that M1 microglia, in general, are associated with deleterious effects on homeostatic cell communication[17-19]. If indicated, treatment of animals with ROS and/or inflammasome inhibitors is examined to determine if the treatment would result in a shift of CLN3$^{\Delta ex7/8}$ microglia towards an anti-inflammatory M2 phenotype that would be expected to restore GJC and HC activity to WT levels.

Example 9

Effects of ROS and Inflammasome Inhibitors on CLN3 Mutant Mice

Given experimental evidence to indicate that CLN3 loss may lead to perturbations in oxidative balance and inflammasome activation in microglia, these studies are extended into the therapeutic realm by treating CLN3$^{\Delta ex7/8}$ mice with well-characterized ROS (i.e., apocynin)[35] and/or inflammasome (i.e., AC-YVAD-CMK)[36] inhibitors to determine the impact on microglial activation, neuronal survival, and other behavioral attributes. In addition, studies will enable the selective ablation of CLN3 in microglia and macrophage populations when crossed with LysM-Cre mice[37]. This will allow for a more specific assessment of the contribution of microglia in the pathogenesis of JNCL.

References for Passages Preceding the Examples and for Examples 1-9

1. Schultz M L, Tecedor L, Chang M, Davidson B L. Clarifying lysosomal storage diseases. Trends Neurosci 2011; 34:401-10.
2. Getty A L, Pearce D A. Interactions of the proteins of neuronal ceroid lipofuscinosis: clues to function. Cell Mol Life Sci 2011; 68:453-74.
3. Isolation of a novel gene underlying Batten disease, CLN3. The International Batten Disease Consortium. Cell 1995; 82:949-57.
4. Pontikis C C, Cotman S L, MacDonald M E, Cooper J D. Thalamocortical neuron loss and localized astrocytosis in the Cln3Deltaex7/8 knock-in mouse model of Batten disease. Neurobiol Dis 2005; 20:823-36.
5. Pontikis C C, Cella C V, Parihar N, et al. Late onset neurodegeneration in the Cln3−/− mouse model of juvenile neuronal ceroid lipofuscinosis is preceded by low level glial activation. Brain Res 2004; 1023:231-42.
6. Arai H, Furuya T, Yasuda T, Miura M, Mizuno Y, Mochizuki H. Neurotoxic effects of lipopolysaccharide on nigral dopaminergic neurons are mediated by microglial activation, interleukin-1beta, and expression of caspase-11 in mice. J Biol Chem 2004; 279:51647-53.
7. Garg S, Nichols J R, Esen N, et al. MyD88 expression by CNS-resident cells is pivotal for eliciting protective immunity in brain abscesses. ASN Neuro 2009; 1.
8. Hanamsagar R, Tones V, Kielian T. Inflammasome activation and IL-1beta/IL-18 processing are influenced by distinct pathways in microglia. J Neurochem 2011; 119: 736-48.
9. Block M L, Zecca L, Hong J S. Microglia-mediated neurotoxicity: uncovering the molecular mechanisms. Nat Rev Neurosci 2007; 8:57-69.
10. Bal-Price A, Brown G C. Inflammatory neurodegeneration mediated by nitric oxide from activated glia-inhibiting neuronal respiration, causing glutamate release and excitotoxicity. J Neurosci 2001; 21:6480-91.
11. Zhou R, Yazdi A S, Menu P, Tschopp J. A role for mitochondria in NLRP3 inflammasome activation. Nature 2011; 469:221-5.
12. Benedict J W, Sommers C A, Pearce D A. Progressive oxidative damage in the central nervous system of a murine model for juvenile Batten disease. J Neurosci Res 2007; 85:2882-91.
13. Tuxworth R I, Chen H, Vivancos V, Carvajal N, Huang X, Tear G. The Batten disease gene CLN3 is required for the response to oxidative stress. Hum Mol Genet 2011; 20:2037-47.
14. Thornton P, Pinteaux E, Gibson R M, Allan S M, Rothwell N J. Interleukin-1-induced neurotoxicity is mediated by glia and requires caspase activation and free radical release. J Neurochem 2006; 98:258-66.
15. Kielian T. Glial connexins and gap junctions in CNS inflammation and disease. J Neurochem 2008.
16. Laird D W. Life cycle of connexins in health and disease. Biochem J 2006; 394:527-43.
17. Hinkerohe D, Smikalla D, Haghikia A, et al. Effects of cytokines on microglial phenotypes and astroglial coupling in an inflammatory coculture model. Glia 2005; 52:85-97.
18. Meme W, Calvo C F, Froger N, et al. Proinflammatory cytokines released from microglia inhibit gap junctions in astrocytes: potentiation by beta-amyloid. Faseb J 2006; 20:494-6.
19. Retamal M A, Froger N, Palacios-Prado N, et al. Cx43 hemi-channels and gap junction channels in astrocytes are regulated oppositely by proinflammatory cytokines released from activated microglia. J Neurosci 2007; 27:13781-92.
20. Colton C A, Wilcock D M. Assessing activation states in microglia. CNS Neurol Disord Drug Targets 2010; 9:174-91.
21. Karpuk N, Burkovetskaya M, Fritz T, Angle A, Kielian T. Neuroinflammation leads to region-dependent alterations in astrocyte gap junction communication and hemi-channel activity. J Neurosci 2011; 31:414-25.
22. Puranam K, Qian W H, Nikbakht K, et al. Upregulation of Bcl-2 and elevation of ceramide in Batten disease. Neuropediatrics 1997; 28:37-41.
23. Puranam K L, Guo W X, Qian W H, Nikbakht K, Boustany R M. CLN3 defines a novel antiapoptotic pathway operative in neurodegeneration and mediated by ceramide. Mol Genet Metab 1999; 66:294-308.
24. Salek R M, Pears M R, Cooper J D, et al. A metabolomic comparison of mouse models of the Neuronal Ceroid Lipofuscinoses. J Biomol NMR 2011; 49:175-84.
25. Esen N, Kielian T. Central role for MyD88 in the responses of microglia to pathogen-associated molecular patterns. J Immunol 2006; 176:6802-11.
26. Kielian T, Esen N, Bearden E D. Toll-like receptor 2 (TLR2) is pivotal for recognition of S. aureus peptidoglycan but not intact bacteria by microglia. Glia 2005; 49:567-76.
27. Holley M M, Zhang Y, Lehrmann E, Wood W H, Becker K G, Kielian T. Toll-like receptor 2 (TLR2)-TLR9 crosstalk dictates IL-12 family cytokine production in microglia. Glia 2011.
28. Takeuchi H, Jin S, Wang J, et al. Tumor necrosis factor-alpha induces neurotoxicity via glutamate release from hemi-channels of activated microglia in an autocrine manner. J Biol Chem 2006; 281:21362-8.
29. Halle A, Hornung V, Petzold G C, et al. The NALP3 inflammasome is involved in the innate immune response to amyloid-beta. Nat Immunol 2008; 9:857-65.
30. Esen N, Tanga F Y, DeLeo J A, Kielian T. Toll-like receptor 2 (TLR2) mediates astrocyte activation in response to the Gram-positive bacterium *Staphylococcus aureus*. J Neurochem 2004; 88:746-58.
31. Orellana J A, Shoji K F, Abudara V, et al. Amyloid beta-induced death in neurons involves glial and neuronal hemi-channels. J Neurosci 2011; 31:4962-77.
32. Esen N, Shuffield D, Syed M M, Kielian T. Modulation of connexin expression and gap junction communication in astrocytes by the gram-positive bacterium *S. aureus*. Glia 2007; 55:104-17.
33. Bargiotas P, Monyer H, Schwaninger M. Hemi-channels in cerebral ischemia. Curr Mol Med 2009; 9:186-94.
34. Thompson R J, Macvicar B A. Connexin and pannexin hemi-channels of neurons and astrocytes. Channels (Austin) 2008; 2:81-6.
35. Chen H, Song Y S, Chan P H. Inhibition of NADPH oxidase is neuroprotective after ischemia-reperfusion. J Cereb Blood Flow Metab 2009; 29:1262-72.
36. Osuka A, Hanschen M, Stoecklein V, Lederer J A. A Protective Role for Inflammasome Activation Following Injury. Shock 2011.
37. Clausen B E, Burkhardt C, Reith W, Renkawitz R, Forster I. Conditional gene targeting in macrophages and granulocytes using LysMcre mice. Transgenic Res 1999; 8:265-77.
38. Xiong, J., and Kielian, T. Microglia in juvenile neuronal ceroid lipofuscinosis are primed toward a pro-inflammatory phenotype. J Neurochem. 2013 October; 127(2):245-258.

Example 10

CLN3$^{\Delta ex7/8}$ Mice Confirm HC Inhibitor and PDE-4 Inhibitor Therapy for JNCL The approach to JNCL prevention and treatment involves the intervention and targeting of aberrant glial activation during early stages of JNCL to maximally delay disease progression. Since the majority of children are not diagnosed with JNCL until 5-10 years of age, drug treatment will be delayed in CLN3$^{\Delta ex7/8}$ and WT mice until either P30 or P90. The former time was selected based on studies by the inventive entity demonstrating that INI-0602 can significantly reduce glutamate accumulation in the hippocampus and striatum of CLN3$^{\Delta ex7/8}$ animals, whereas D90 reflects a situation where a JNCL diagnosis is delayed. In both scenarios, drug treatment is continued until animals are 6-8 months old, whereupon neuronal survival is quantitated in thalamocortical structures using unbiased stereology. Behavioral analysis and MR spectroscopy are also performed at regular intervals throughout the treatment period. Three doses of INI-0602 and PDE-4 inhibitors are examined in these studies. Since the doses selected are based on the studies with INI-0602 and literature that demonstrates protective effects in various CNS diseases, therapeutic dosages are expected to be identified. INI-0602 (1, 10, or 50 mg/kg/day) is administered i.p. every other day throughout the treatment period. It is recognized that repeated i.p. injection does not represent a preferred administration route; however, this approach is required since INI-0602 degrades rapidly when dissolved (T½=approx. 6 hours) and prior attempts to incorporate the drug into chow or deliver via an Alzet osmotic pump were not successful (i.e., the drug was not detected in blood, CSF, or CNS tissue). A recent report documented that repetitive INI-0602 i.p. injections for more than 6 months was well-tolerated in mouse models of ALS and AD without any adverse effects or systemic toxicity. PDE-4 inhibitors (e.g., PPF, rolipram, and roflumilast; 1, 10, or 50 mg/kg/day) are administered via oral gavage, which represented a successful drug delivery method in other studies. In addition, the long-term duration of drug action is assessed by lengthening the period under investigation.

For most studies, a total of 10 $CLN3^{\Delta ex7/8}$ and WT littermates/time point/drug is used, which was determined by a t-test power analysis, since comparisons are made between vehicle and drug-treated mice. Specifically, estimating a minimal detectable difference in means of 2 induced by drug treatment (i.e., 2-fold difference in glutamate/GABA levels, neuron numbers, or behavioral measurements), an expected standard deviation of 1.5, 2 experimental groups (vehicle vs. drug), a desired power of 0.8, and an alpha value of 0.05, requires a sample size of 10 animals per experimental group. Due to the inherent degree of biological variability between individual experiments, each study is repeated twice to confirm treatment efficacy. Male $CLN3^{\Delta ex7/8}$ and WT littermates are randomized into treatment groups based on weight by a laboratory member who is not directly associated with the study. Animal identity is coded and recorded such that all study personnel are blinded to mouse strain identity. Although the identity of cages receiving INI-0602/PDE-4 inhibitor or vehicle is known in order to deliver the correct compound, the identity of individual animals as $CLN3^{\Delta ex7/8}$ or WT within each cage remains unknown until the termination of the study, when data is de-identified. These measures will minimize potential bias during data collection.

Example 11

The Hemi-Channel Inhibitor INI-0602 Attenuates Glutamate Accumulation During Early JNCL CNS homeostasis depends, in part, on cellular networks formed by gap junctions, which play a role in maintaining extracellular pH, K+, and glutamate levels[15]. Gap junction channels are formed by the joining of two hemi-channels (HCs) from adjacent cells[16], and it has recently been demonstrated that HCs can be opened during pathological conditions[21,31]. It has been established that HCs are open during the early postnatal period in $CLN3^{\Delta ex7/8}$ mice, which persists for at least three months in specific brain regions. Therefore, it is expected that continued HC activity disrupts homeostatic glutamate gradients (and other physiological gradients), which contributes to neuronal loss during later stages of JNCL. Data disclosed herein indicate that INI-0602 is capable of modulating behavior, reducing glutamate accumulation, and enhancing GJC in $CLN3^{\Delta ex7/8}$ mice. In this Example, the optimal neuroprotective regimen for INI-0602 in JNCL is determined by monitoring glutamate concentrations in several thalamocortical structures by MR spectroscopy, by observing behavior, and by examining neuronal survival in $CLN3^{\Delta ex7/8}$ mice.

Monitoring INI-0602 Action on the Brain Metabolome by $^1$H Magnetic Resonance Spectroscopy (MR Spectroscopy)

A major pathogenic mechanism implicated in neuronal loss during JNCL is excessive excitotoxic and reduced inhibitory input mediated by elevated glutamate and reduced GABA levels, respectively. MR spectroscopy data have shown that a one-month treatment regimen with INI-0602 significantly attenuated glutamate levels in the hippocampus and striatum of $CLN3^{\Delta ex7/8}$ mice while enhancing GABA. It is expected that these effects will result from inhibition of aberrant HC activity in $CLN3^{\Delta ex7/8}$ mice concomitant with reduced inflammatory mediator expression within thalamo-cortical structures. To assess these possibilities, $CLN3^{\Delta ex7/8}$ and WT littermates receive 1, 10, or 50 mg/kg INI-0602 i.p. every other day beginning either at postnatal day 30 or 90 and continuing until 6-7 months of age.

Studies using mouse models are limited by the inability to acquire anatomic and functional data non-invasively in a longitudinal manner. Compared with traditional histological techniques that are time consuming and limited to examining changes at a fixed point in time, MRI can be acquired as three-dimensional data sets with very accurate depiction of anatomy, physiology, and biochemistry in a relatively short time interval[25,26]. Lack of exposure to ionizing radiation makes this an ideal methodology for serial non-invasive studies. MR spectroscopy imaging is a non-invasive method to obtain direct metabolic information from living animals. Proton MR spectroscopically visible metabolites are primarily glutamate, glutamine, N-acetyl aspartate (NAA), choline, creatine, and myoinostitol[27]. Recent advances in curve fitting methodology also allow for the measurement of low-level metabolites, including GABA, glucose, glycine, alanine, aspartic acid, and taurine. Studies have demonstrated the utility of single-voxel proton MR spectroscopy to quantitate changes in the brain metabolome during JNCL, in particular, highlighting elevations in glutamate concomitant with reductions in GABA and NAA[7]. NAA is synthesized exclusively in the mitochondria of neurons and is widely used as a marker of neuronal integrity, whereby neuronal cell death results in an irreversible loss of NAA[28]. Glutamate is elevated in the brains of JNCL patients and experiments have revealed increased glutamate in the hippocampus and striatum of $CLN3^{\Delta ex7/8}$ mice at P60 that can be reduced to WT levels following INI-0602 treatment. GABA is an inhibitory transmitter and its metabolism is tightly linked to glutamate. Experiments have shown reduced GABA in the hippocampus and striatum at P60 that can be increased to near WT levels following INI-0602 treatment. Therefore, there is a precedent for beneficial effects of INI-0602 on key metabolic disturbances during early JNCL that can impact neuron survival. In experiments, NAA was not decreased in $CLN3^{\Delta ex7/8}$ mice at day 60, which was predicted, since neuronal loss is not observed until 5-7 months of age. However, NAA levels are expected to progressively decline during later imaging intervals and it is expected that HC inhibitors such as INI-0602 can reverse this effect.

Figure 16:
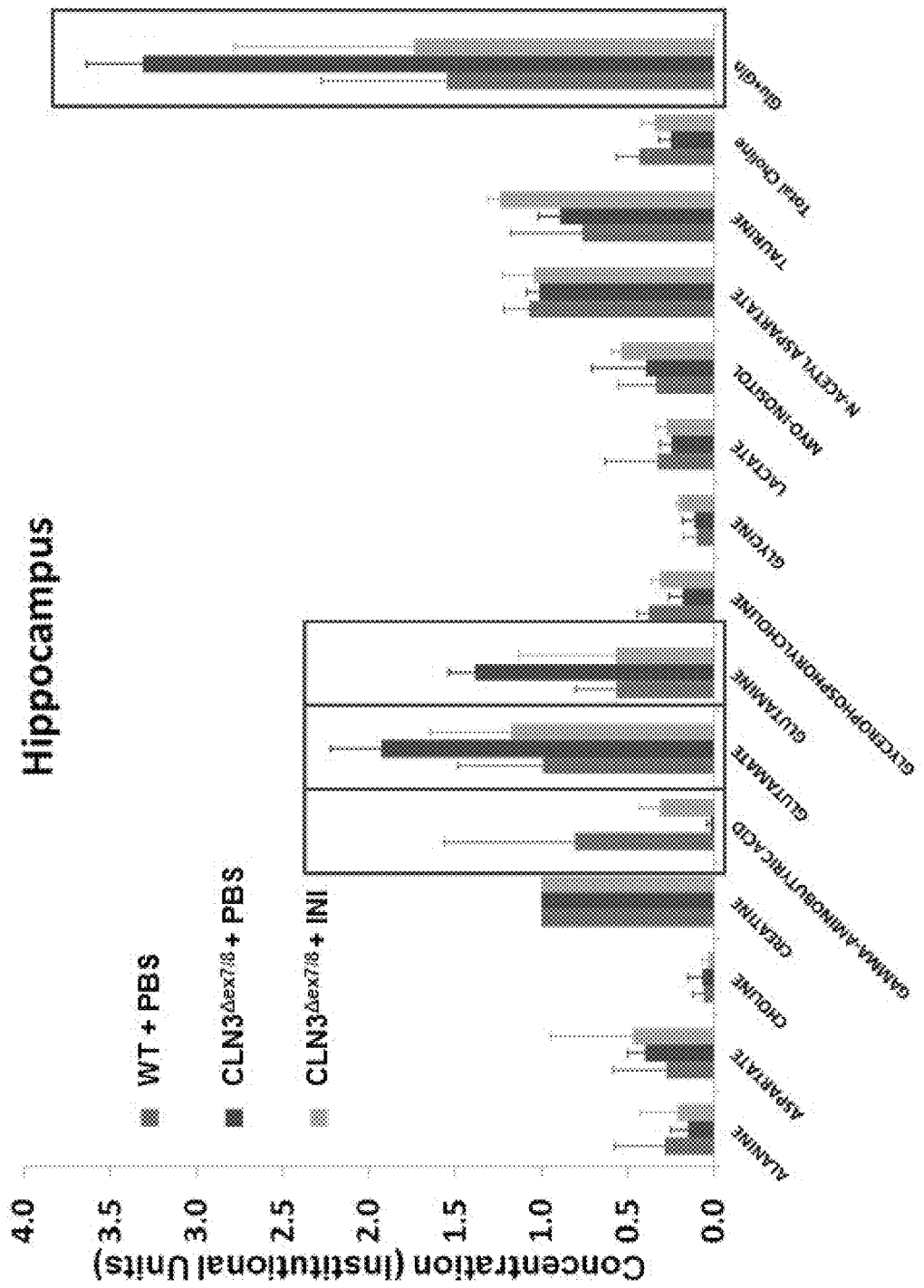
FIG. 16. INI-0602-induced restoration of WT levels of brain metabolites in the CLN3$^{\Delta ex7/8}$ mouse hippocampus. Mice received i.p. injections of INI-0602 (10 mg/kg) or vehicle (PBS) every other day beginning at postnatal day 30 and continuing until postnatal day 60. Mice were subjected to magnetic resonance spectroscopy (MRS) imaging at day 60 to measure brain metabolites. Glutamate and glutamine levels were dramatically increased in CLN3 mutant mice (red bars), which was reduced to nearly WT levels by INI-0602 treatment (light green bars). In contrast, gamma-aminobutyric acid (GABA) levels were reduced in CLN3 mutant mice and INI-0602 treatment increased GABA concentrations nearer to that observed in WT mice.

MR spectroscopy is performed at monthly intervals throughout the treatment period to assess the effect of INI-0602 dosing schedules on the brain metabolome. The analysis focuses on changes in glutamate, GABA, and NAA levels in the hippocampus (FIG. 16), striatum (FIG. 17), S1BF cortex (FIG. 18), and thalamus, regions where neuron loss is detected in $CLN3^{\Delta ex7/8}$ mice within 5-7 months of age. The approach is designed to focus on a limited metabolite repertoire.

Two 7 Tesla (7T) small animal magnetic resonance imaging and spectroscopy (MRI/S) systems (7T/21 cm Biospec, and a 7T/16 cm Pharmascan, Bruker Biospin, Karlshure, Germany) are operational at the University of Nebraska Medical Center. Mice are anesthetized with 1.5% isoflurane in a 70% nitrous oxide/30% oxygen mixture and positioned in a custom-made stereotactic holder equipped with a SA instruments model 1025 MRI-compatible physiological monitoring system (Model 1025, SA Instruments, Stony Brook, N.Y.). Monitoring capabilities include respiratory, temperature, and EKG monitors, with optional pulse oximetry and $CO_2$ monitors, as needed. Core body temperature of anesthetized mice is maintained by a warm air delivery system. The initial set-up for all MRI studies includes a 3-plane locator scan. Localization and initial shimming using a novel field mapping method[31] requires about 10 minutes. Once the mouse is in position and shimmed, MR spectra are obtained. Results from QA phantoms are compared to animals to verify accuracy and random error measurements.

Based on studies disclosed herein, it is predicted that an HC inhibitor such as INI-0602 will significantly reduce glutamate and elevate GABA levels in thalamocortical structures of $CLN3^{\Delta ex7/8}$ mice when treatment is initiated at P30. Repeated MR spectroscopy analysis permits a determination of the longevity of this effect, which we expect to persist until study termination. Because aberrant HC opening can dramatically affect metabolic homeostasis, it is also expected that delayed INI-0602 treatment beginning at P90 will reverse glutamate and GABA abnormalities, since overt neuronal loss is not evident in $CLN3^{\Delta ex7/8}$ mice until 5-7 months of age. This would provide a therapeutic avenue for treating established pathology, because JNCL is typically not diagnosed until children reach a more advanced age.

INI-0602 Attenuates Neuronal Loss and Glial Activation in JNCL Brain

To establish that INI-0602 is capable of significantly delaying and/or reducing neuronal loss, neuron numbers are quantitated and the extent of microglial and astrocyte activation within the same brain regions is monitored by MR spectroscopy using unbiased stereology. Briefly, unbiased optical estimates of neuron, microglia, and astrocyte numbers within the hippocampus, striatum, S1BF cortex, and thalamus are calculated using StereoInvestigator software (Microbrightfield Inc., Williston, Vt.). Unbiased optical fractionator estimates of Nissl (neuron) or DAB-stained microglia (Iba-1) and astrocytes (GFAP) are obtained from tissue sections of $CLN3^{\Delta ex7/8}$ and WT littermates subjected to INI-0602 treatment. Unbiased fractionator cell counts are performed as previously described (Bible et al., 2004; Pontikis et al., 2004), with a random starting section chosen, followed by every second stained section thereafter. Only neurons with a clearly identifiable nucleus are sampled and all counts are carried out using a 60× oil objective. Differences in the quantitative data between CLN3 genotypes are assessed using a one-way ANOVA with statistical significance considered at $p<0.05$. The mean co-efficient of error (CE) for all individual optical fractionator and nucleator estimates is calculated according to the method of Gundersen and Jensen (Gundersen and Jensen, 1987). NAA levels are monitored by MR spectroscopy, which provides an independent measure to validate the beneficial effects of INI-0602 on neuronal integrity. It is expected that INI-0602 will significantly reduce neuronal loss and glial activation within the brain structures examined here, which are target regions for neuron death in $CLN3^{\Delta ex7/8}$ mice. It is expected that INI-0602 will facilitate neuronal survival and glial activation by its ability to dramatically reduce glutamate levels within the $CLN3^{\Delta ex7/8}$ brain, as demonstrated by studies disclosed herein coupled with the fact that glutamate excitotoxicity has been suggested as a key mechanism for neuronal loss in JNCL. Because glutamate levels and neuron survival are tightly linked, we expect both processes to be regulated by INI-0602 with a similar dosing and intervention schedule.

Restoration of the Brain Metabolome by INI-0602 Leads to Behavioral Improvements in $CLN3^{\Delta ex7/8}$ Mice Early cognitive and motor abnormalities have been identified in $CLN3^{\Delta ex7/8}$ mice. Since these behavioral attributes can provide insights into disease severity, a battery of tests is performed to assess cognitive (i.e., nest building and open field activity) and motor skills (i.e., rotorod, grasping) in the HC inhibitor (e.g., INI-0602) treatment regimens. All mouse behaviors are monitored in a dedicated suite that lacks positional cues and recorded using a digital camcorder located over the center of the cage. For assessing open field activity, mice are placed in the corner of a large mouse cage devoid of bedding. Behavior is videotaped for a 20-minute period, whereupon the mouse is immediately be returned to its home cage. The test cage is thoroughly cleaned between animals to avoid confounds from residual scents. After completion of experiments, videos are digitized and quantitated using EthoVision software. Examples of the types of measurements that are monitored include number of rearings, distance moved, velocity, and mobile/immobile ratio. For motor assessments, INI-0602 may differentially impact grasping and rotorod outcomes. With regard to rotorod performance, $CLN3^{\Delta ex7/8}$ mice display decreased latency to fall at 8 weeks of age compared to WT animals, which is most pronounced at higher speeds. Because rotorod deficits are detected in older $CLN3^{\Delta ex7/8}$ mice, the P30 INI-0602 treatment schedule may improve motor function; however, delaying drug administration out to P90 may not provide any benefits. Nonetheless, the extended treatment period with INI-0602 may be sufficient to overcome the rotorod deficit, if plasticity is possible given the role of HCs in regulating homeostatic gradients within the brain. With regard to exploratory behavior, it is expected that HC inhibitors such as INI-0602 will increase exploratory activity in $CLN3^{\Delta ex7/8}$ mice, which is normally reduced compared to WT littermates at 8 weeks of age Finally, a recent study in mouse models of ALS and AD showed that INI-0602 had an exemplary safety record, with no evidence of blood or urine abnormalities over a 7-month dosing interval[9]. To assess the safety profile of INI-0602 in our dosing schedules, CBC and blood chemistry profiles are monitored on a monthly basis using a VetScan2 instrument, which provides an assessment of 19 distinct blood chemistries as well as recording body weights every other day. This, in conjunction with the MR spectroscopy studies to evaluate brain metabolites in wild-type animals treated with an HC inhibitor such as INI-0602 allows assessment of whether the compound exhibits any adverse side effects in either the CNS or periphery. Based on the reported safety profile of INI-0602 following a 7-month treatment interval in a mouse AD model, it is expected that there will be no toxicity associated with repeated INI-0602 administration.

INI-0602 Attenuates Inflammatory Mediator Expression During JNCL

Another factor that can contribute to imbalances in glutamate homeostasis and neuronal death is enhanced inflammation. Progressive age-dependent increases in proinflammatory mediator production are observed in the brains of CLN1 mutant mice and similar inflammatory events manifest during JNCL that may contribute to neuronal loss coincident with glutamate excitotoxicity. Therefore, as a consequence of restoring the brain metabolome of $CLN3^{\Delta ex7/8}$ mice, it is expected that indices of inflammation are attenuated in HC inhibitor-treated (e.g., INI-0602-treated) animals. To address this issue, proinflammatory mediator expression in the cortex, hippocampus, and cerebellum is quantitated using multi-analyte microbead arrays that are capable of detecting 20 distinct inflammatory mediators in a single 75 μl volume. All mediators are normalized to the amount of total protein obtained from each brain region to correct for differences in tissue sampling size. Since overt neuroinflammation typically occurs during the later stages of lysosomal storage diseases (i.e., LSDs), it is predicted that both the early and delayed INI-0602 treatment regimens will significantly inhibit proinflammatory mediator release in the brains of CLN3$^{\Delta ex7/8}$ mice.

Example 12

Phosphodiesterase-4 Inhibitors Reduce Neuronal Loss During JNCL

These experiments are designed to target glial inflammatory activity and glutamate levels by PPF, rolipram, and roflumilast (as well as proprietary PDE-4 inhibitors from industry) administration to delay and/or limit neuronal loss in CLN3$^{\Delta ex7/8}$ mice. Data disclosed herein have demonstrated that PPF, roflumilast, and rolipram are capable of attenuating exaggerated proinflammatory cytokine release by CLN3$^{\Delta ex7/8}$ microglia. In addition, it has been shown that PPF augments astrocytic GLAST expression, which is expected to represent a second therapeutic benefit by limiting the glutamate accumulation that occurs in JNCL patients. The studies described herein assess the combined actions of targeting proinflammatory mediator release and glutamate transporters in regulating neuron loss, and examine disruption of metabolic gradients via HC activity. Therefore, both approaches test distinct mechanisms yet similar target responses, which provide a combined therapeutic approach.

In these experiments, mice receive either PPF, rolipram, roflumilast, or other proprietary PDE-4 inhibitors via a schedule similar to the schedule used for INI-0602. An important distinction is that these compounds are amenable to oral administration and as such, animals will receive daily dosing via oral gavage.

PDE-4 Inhibitors can Attenuate Proinflammatory Mediator Production and Glutamate Accumulation During Early JNCL Studies have established that proinflammatory mediators, such as TNF-α and IL-1β can augment glutamate release and neuronal death. In addition, TNF-α regulates synaptic strength by modulating AMPA receptors and excessive cytokine release contributes to hippocampal seizure activity. Defects in AMPA receptor activity have been implicated in early JNCL. Experimental results disclosed herein have demonstrated exaggerated release of TNF-α in addition to other proinflammatory cytokines known to impact neuronal homeostasis, including IL-1β and IL-6 in CLN3$^{\Delta ex7/8}$ microglia. It is expected that loss of CLN3 function and associated lysosomal dysfunction leads to a progressive proinflammatory state within the JNCL brain, which over time contributes to heightened glutamate levels and neuronal death. The ability of the PDE-4 inhibitors PPF, rolipram, roflumilast, and proprietary PDE-4 inhibitors to reverse these defects is assessed by monitoring glutamate, GABA, and NAA concentrations within the hippocampus, striatum, S1BF cortex, and thalamus as well as quantitating neuronal numbers using unbiased stereology. PPF, rolipram, roflumilast, and proprietary PDE-4 inhibitors are administered as described and any associated toxicity is assessed by blood chemistry analysis. It is expected that PPF, rolipram, roflumilast, and/or proprietary PDE-4 inhibitors is/are capable of attenuating glial proinflammatory mediator production, leading to significantly reduced glutamate levels in the brains of CLN3$^{\Delta ex7/8}$ mice. Likewise, reductions in proinflammatory cytokines would reduce the possibility of triggering seizure activity, as has been described in the hippocampus. Seizures are a significant clinical manifestation in JNCL patients, and likely contribute to neuronal loss as they progressively increase in severity as children age. Recent evidence indicates that proinflammatory cytokines negatively impact GABAergic neurons, providing a basis for the prediction that PDE-4 inhibitors will prevent the loss of GABAergic neurons as revealed by higher GABA concentrations in MR spectroscopy. Finally, it is expected that PDE-4 inhibitor treatment will result in less neuronal loss at later stages of disease, which will coincide with lower levels of proinflammatory mediators in the CLN3$^{\Delta ex7/8}$ brain. Longitudinal assessment of neuronal integrity is independently assessed by NAA values during MR spectroscopy analysis, which will complement stereology measurements.

Restoration of the Brain Metabolome by PDE-4 Inhibitors Leads to Behavioral Improvements in CLN3$^{\Delta ex7/8}$ Mice Since behavioral attributes can provide insights into disease severity, a battery of tests is performed to assess cognitive (i.e., nest building and open field activity) and motor skills (i.e., rotorod, grasping) in CLN3$^{\Delta ex7/8}$ mice when subjected to each of the tested PDE-4 inhibitor treatment schedules. PDE-4 inhibitors have been shown to reduce mechanical allodynia following peripheral nerve injury and to improve locomotor recovery following SCI. These findings indicate that PPF/rolipram/roflumilast/proprietary PDE-4 inhibitors will benefit motor function (i.e., rotorod, grasping) in CLN3$^{\Delta ex7/8}$ animals.

References for Passages Preceding the Examples and for Examples 10-12

1. Isolation of a novel gene underlying Batten disease, CLN3. The International Batten Disease Consortium. Cell. 1995; 82(6):949-957.
2. Schultz M L, Tecedor L, Chang M, Davidson B L. Clarifying lysosomal storage diseases. Trends Neurosci. 2011; 34(8):401-410.
3. Williams R E, Mole S E. New nomenclature and classification scheme for the neuronal ceroid lipofuscinoses. Neurology. 2012; 79(2):183-191.
4. Pontikis C C, Cella C V, Parihar N, et al. Late onset neurodegeneration in the Cln3−/− mouse model of juvenile neuronal ceroid lipofuscinosis is preceded by low level glial activation. Brain Res. 2004; 1023(2):231-242.
5. Pontikis C C, Cotman S L, MacDonald M E, Cooper J D. Thalamocortical neuron loss and localized astrocytosis in the Cln3Deltaex7/8 knock-in mouse model of Batten disease. Neurobiol Dis. 2005; 20(3):823-836.
6. Scemes E. Nature of plasmalemmal functional "hemichannels". Biochim Biophys Acta. 2012; 1818(8):1880-1883.
7. Laird D W. Life cycle of connexins in health and disease. Biochem J. 2006; 394(Pt 3):527-543.
8. Eugenin E A, Basilio D, Saez J C, et al. The role of gap junction channels during physiologic and pathologic conditions of the human central nervous system. J Neuroimmune Pharmacol. 2012; 7(3):499-518.
9. Kielian T. Glial connexins and gap junctions in CNS inflammation and disease. J Neurochem. 2008; 106(3):1000-1016.
10. McGeer P L, McGeer E G. Inflammation and neurodegeneration in Parkinson's disease. Parkinsonism Relat Disord. 2004; 10 Suppl 1:S3-7.

11. Blasko I, Stampfer-Kountchev M, Robatscher P, Veerhuis R, Eikelenboom P, Grubeck-Loebenstein B. How chronic inflammation can affect the brain and support the development of Alzheimer's disease in old age: the role of microglia and astrocytes. Aging Cell. 2004; 3(4):169-176.
12. Wyss-Coray T, Mucke L. Inflammation in neurodegenerative disease—a double-edged sword. Neuron. 2002; 35(3):419-432.
13. Lucas S M, Rothwell N J, Gibson R M. The role of inflammation in CNS injury and disease. Br J Pharmacol. 2006; 147 Suppl 1:S232-240.
14. Getty A L, Pearce D A. Interactions of the proteins of neuronal ceroid lipofuscinosis: clues to function. Cell Mol Life Sci. 2011; 68(3):453-474.
15. Takeuchi H, Mizoguchi H, Doi Y, et al. Blockade of gap junction hemichannel suppresses disease progression in mouse models of amyotrophic lateral sclerosis and Alzheimer's disease. PLoS One. 2011; 6(6):e21108.
16. Tawfik V L, Regan M R, Haenggeli C, et al. Propentofylline-induced astrocyte modulation leads to alterations in glial glutamate promoter activation following spinal nerve transection. Neuroscience. 2008; 152(4):1086-1092.
17. Tawfik V L, Lacroix-Fralish M L, Bercury K K, Nutile-McMenemy N, Harris B T, Deleo J A. Induction of astrocyte differentiation by propentofylline increases glutamate transporter expression in vitro: heterogeneity of the quiescent phenotype. Glia. 2006; 54(3):193-203.
18. Schaal S M, Garg M S, Ghosh M, et al. The Therapeutic Profile of Rolipram, PDE Target and Mechanism of Action as a Neuroprotectant following Spinal Cord Injury. PLoS One. 2012; 7(9):e43634.
19. Nikulina E, Tidwell J L, Dai H N, Bregman B S, Filbin M T. The phosphodiesterase inhibitor rolipram delivered after a spinal cord lesion promotes axonal regeneration and functional recovery. Proc Natl Acad Sci USA. 2004; 101(23):8786-8790.
20. DeMarch Z, Giampa C, Patassini S, Martorana A, Bernardi G, Fusco F R. Beneficial effects of rolipram in a quinolinic acid model of striatal excitotoxicity. Neurobiol Dis. 2007; 25(2):266-273.
21. Sommer N, Martin R, McFarland H F, et al. Therapeutic potential of phosphodiesterase type 4 inhibition in chronic autoimmune demyelinating disease. J Neuroimmunol. 1997; 79(1):54-61.
22. Gong B, Vitolo O V, Trinchese F, Liu S, Shelanski M, Arancio O. Persistent improvement in synaptic and cognitive functions in an Alzheimer mouse model after rolipram treatment. J Clin Invest. 2004; 114(11):1624-1634.
23. Atkins C M, Oliva A A, Jr., Alonso O F, Pearse D D, Bramlett H M, Dietrich W D. Modulation of the cAMP signaling pathway after traumatic brain injury. Exp Neurol. 2007; 208(1):145-158.
24. Beavo J A. Cyclic nucleotide phosphodiesterases: functional implications of multiple isoforms. Physiol Rev. 1995; 75(4):725-748.
25. Iona S, Cuomo M, Bushnik T, et al. Characterization of the rolipram-sensitive, cyclic AMP-specific phosphodiesterases: identification and differential expression of immunologically distinct forms in the rat brain. Mol Pharmacol. 1998; 53(1):23-32.
26. Troadec J D, Marien M, Mourlevat S, et al. Activation of the mitogen-activated protein kinase (ERK(1/2)) signaling pathway by cyclic AMP potentiates the neuroprotective effect of the neurotransmitter noradrenaline on dopaminergic neurons. Mol Pharmacol. 2002; 62(5):1043-1052.
27. Giaume C, Marin P, Cordier J, Glowinski J, Premont J. Adrenergic regulation of intercellular communications between cultured striatal astrocytes from the mouse. Proc Natl Acad Sci USA. 1991; 88(13):5577-5581.
28. Dastidar S G, Rajagopal D, Ray A. Therapeutic benefit of PDE4 inhibitors in inflammatory diseases. Curr Opin Investig Drugs. 2007; 8(5):364-372.
29. Salek R M, Pears M R, Cooper J D, et al. A metabolomic comparison of mouse models of the Neuronal Ceroid Lipofuscinoses. J Biomol NMR. 2011; 49(3-4):175-184.
30. Brockmann K, Pouwels P J, Christen H J, Frahm J, Hanefeld F. Localized proton magnetic resonance spectroscopy of cerebral metabolic disturbances in children with neuronal ceroid lipofuscinosis. Neuropediatrics. 1996; 27(5):242-248.
31. Cotman S L, Vrbanac V, Lebel L A, et al. Cln3(Deltaex7/8) knock-in mice with the common JNCL mutation exhibit progressive neurologic disease that begins before birth. Hum Mol Genet. 2002; 11(22):2709-2721.
32. Mole S E, Zhong N A, Sarpong A, et al. New mutations in the neuronal ceroid lipofuscinosis genes. Eur J Paediatr Neurol. 2001; 5 Suppl A:7-10.
33. Herrmann P, Druckrey-Fiskaaen C, Kouznetsova E, et al. Developmental impairments of select neurotransmitter systems in brains of Cln3(Deltaex7/8) knock-in mice, an animal model of juvenile neuronal ceroid lipofuscinosis. J Neurosci Res. 2008; 86(8):1857-1870.
34. Osorio N S, Sampaio-Marques B, Chan C H, et al. Neurodevelopmental delay in the Cln3Deltaex7/8 mouse model for Batten disease. Genes Brain Behav. 2009; 8(3):337-345.
35. Kovacs A D, Saje A, Wong A, Ramji S, Cooper J D, Pearce D A. Age-dependent therapeutic effect of memantine in a mouse model of juvenile Batten disease. Neuropharmacology. 2012; 63(5):769-775.
36. Kwon J M, Adams H, Rothberg P G, et al. Quantifying physical decline in juvenile neuronal ceroid lipofuscinosis (Batten disease). Neurology. 2011; 77(20):1801-1807.
37. Marshall F J, de Blieck E A, Mink J W, et al. A clinical rating scale for Batten disease: reliable and relevant for clinical trials. Neurology. 2005; 65(2):275-279.
38. Landis S C, Amara S G, Asadullah K, et al. A call for transparent reporting to optimize the predictive value of preclinical research. Nature. 2012; 490(7419):187-191.
39. Cialone J, Adams H, Augustine E F, et al. Females experience a more severe disease course in Batten disease. J Inherit Metab Dis. 2012; 35(3):549-555.
40. Kielian T. Glial connexins and gap junctions in CNS inflammation and disease. J Neurochem. 2008.
41. Karpuk N, Burkovetskaya M, Fritz T, Angle A, Kielian T. Neuroinflammation leads to region-dependent alterations in astrocyte gap junction communication and hemichannel activity. J Neurosci. 2011; 31(2):414-425.
42. Orellana J A, Shoji K F, Abudara V, et al. Amyloid beta-induced death in neurons involves glial and neuronal hemichannels. J Neurosci. 2011; 31(13):4962-4977.
43. Pears M R, Cooper J D, Mitchison H M, Mortishire-Smith R J, Pearce D A, Griffin J L. High resolution 1H NMR-based metabolomics indicates a neurotransmitter cycling deficit in cerebral tissue from a mouse model of Batten disease. J Biol Chem. 2005; 280(52):42508-42514.
44. Kovacs A D, Saje A, Wong A, et al. Temporary inhibition of AMPA receptors induces a prolonged improvement of 45. Kovacs A D, Pearce D A. Attenuation of AMPA receptor activity improves motor skills in a mouse model of juvenile Batten disease. Exp Neurol. 2008; 209(1):288-291.
46. Pautler R G. Mouse MRI: concepts and applications in physiology. Physiology (Bethesda). 2004; 19:168-175.
47. Chatziioannou A F. Instrumentation for molecular imaging in preclinical research: Micro-PET and Micro-SPECT. Proc Am Thorac Soc. 2005; 2(6):533-536, 510-511.
48. Valenzuela M J, Sachdev P. Magnetic resonance spectroscopy in AD. Neurology. 2001; 56(5):592-598.
49. Urenjak J, Williams S R, Gadian D G, Noble M. Specific expression of N-acetylaspartate in neurons, oligodendrocyte-type-2 astrocyte progenitors, and immature oligodendrocytes in vitro. J Neurochem. 1992; 59(1):55-61.
50. Miyasaka N, Takahashi K, Hetherington H P. Fully automated shim mapping method for spectroscopic imaging of the mouse brain at 9.4 T. Magn Reson Med. 2006; 55(1):198-202.
51. Giaume C, Koulakoff A, Roux L, Holcman D, Rouach N. Astroglial networks: a step further in neuroglial and gliovascular interactions. Nat Rev Neurosci. 2010; 11(2):87-99.
52. Bible E, Gupta P, Hofmann S L, Cooper J D. Regional and cellular neuropathology in the palmitoyl protein thioesterase-1 null mutant mouse model of infantile neuronal ceroid lipofuscinosis. Neurobiol Dis. 2004; 16(2):346-359.
53. Gundersen H J, Jensen E B. The efficiency of systematic stereology and its prediction. J Microsc. 1987; 147:229-263.
54. Antonawich F J, Melton C S, Wu P, Davis J N. Nesting and shredding behavior as an indicator of hippocampal ischemic damage. Brain Res. 1997; 764(1-2):249-252.
55. Deacon R M. Assessing nest building in mice. Nat Protoc. 2006; 1(3):1117-1119.
56. Deacon R M, Croucher A, Rawlins J N. Hippocampal cytotoxic lesion effects on species-typical behaviours in mice. Behav Brain Res. 2002; 132(2):203-213.
57. Macauley S L, Roberts M S, Wong A M, et al. Synergistic effects of central nervous system-directed gene therapy and bone marrow transplantation in the murine model of infantile neuronal ceroid lipofuscinosis. Ann Neurol. 2012; 71(6):797-804.
58. Liu S, Kielian T. MyD88 is pivotal for immune recognition of *Citrobacter koseri* and astrocyte activation during CNS infection. J Neuroinflammation. 2011; 8:35.
59. Holley M M, Kielian T. Th1 and Th17 cells regulate innate immune responses and bacterial clearance during central nervous system infection. J Immunol. 2012; 188(3):1360-1370.
60. Kielian T, Haney A, Mayes P M, Garg S, Esen N. Toll-like receptor 2 modulates the proinflammatory milieu in *Staphylococcus aureus*-induced brain abscess. Infect Immun. 2005; 73(11):7428-7435.
61. Qin E Y, Hawkins-Salsbury J A, Jiang X, et al. Bone marrow transplantation increases efficacy of central nervous system-directed enzyme replacement therapy in the murine model of globoid cell leukodystrophy. Mol Genet Metab. 2012; 107(1-2):186-196.
62. Stoll G, Jander S, Schroeter M. Cytokines in CNS disorders: neurotoxicity versus neuroprotection. J Neural Transm Suppl. 2000; 59:81-89.
63. McCoy M K, Tansey M G. TNF signaling inhibition in the CNS: implications for normal brain function and neurodegenerative disease. J Neuroinflammation. 2008; 5:45.
64. Rothwell N. Interleukin-1 and neuronal injury: mechanisms, modification, and therapeutic potential. Brain Behav Immun. 2003; 17(3):152-157.
65. Allan S M, Tyrrell P J, Rothwell N J. Interleukin-1 and neuronal injury. Nat Rev Immunol. 2005; 5(8):629-640.
66. Beattie E C, Stellwagen D, Morishita W, et al. Control of synaptic strength by glial TNFalpha. Science. 2002; 295(5563):2282-2285.
67. Stellwagen D, Malenka R C. Synaptic scaling mediated by glial TNF-alpha. Nature. 2006; 440(7087):1054-1059.
68. Santello M, Volterra A. TNFalpha in synaptic function: switching gears. Trends Neurosci. 2012; 35(10):638-647.
69. Huie J R, Baumbauer K M, Lee K H, et al. Glial tumor necrosis factor alpha (TNFalpha) generates metaplastic inhibition of spinal learning. PLoS One. 2012; 7(6):e39751.
70. Hellstrom I C, Danik M, Luheshi G N, Williams S. Chronic LPS exposure produces changes in intrinsic membrane properties and a sustained IL-beta-dependent increase in GABAergic inhibition in hippocampal CA1 pyramidal neurons. Hippocampus. 2005; 15(5):656-664.
71. Tabarean I V, Korn H, Bartfai T. Interleukin-1beta induces hyperpolarization and modulates synaptic inhibition in preoptic and anterior hypothalamic neurons. Neuroscience. 2006; 141(4):1685-1695.
72. Pearse D D, Pereira F C, Marcillo A E, et al. cAMP and Schwann cells promote axonal growth and functional recovery after spinal cord injury. Nat Med. 2004; 10(6):610-616.
73. Tawfik V L, Nutile-McMenemy N, Lacroix-Fralish M L, Deleo J A. Efficacy of propentofylline, a glial modulating agent, on existing mechanical allodynia following peripheral nerve injury. Brain Behav Immun. 2007; 21(2):238-246.
74. Lim M J, Beake J, Bible E, et al. Distinct patterns of serum immunoreactivity as evidence for multiple brain-directed autoantibodies in juvenile neuronal ceroid lipofuscinosis. Neuropathol Appl Neurobiol. 2006; 32(5):469-482.
75. Seehafer S S, Ramirez-Montealegre D, Wong A M, et al. Immunosuppression alters disease severity in juvenile Batten disease mice. J Neuroimmunol. 2011; 230(1-2):169-172.
76. Fehniger T A, Caligiuri M A. Interleukin 15: biology and relevance to human disease. Blood. 2001; 97(1):14-32.

Example 13

Effect of HC Inhibitor on JNCL

Figure 5:
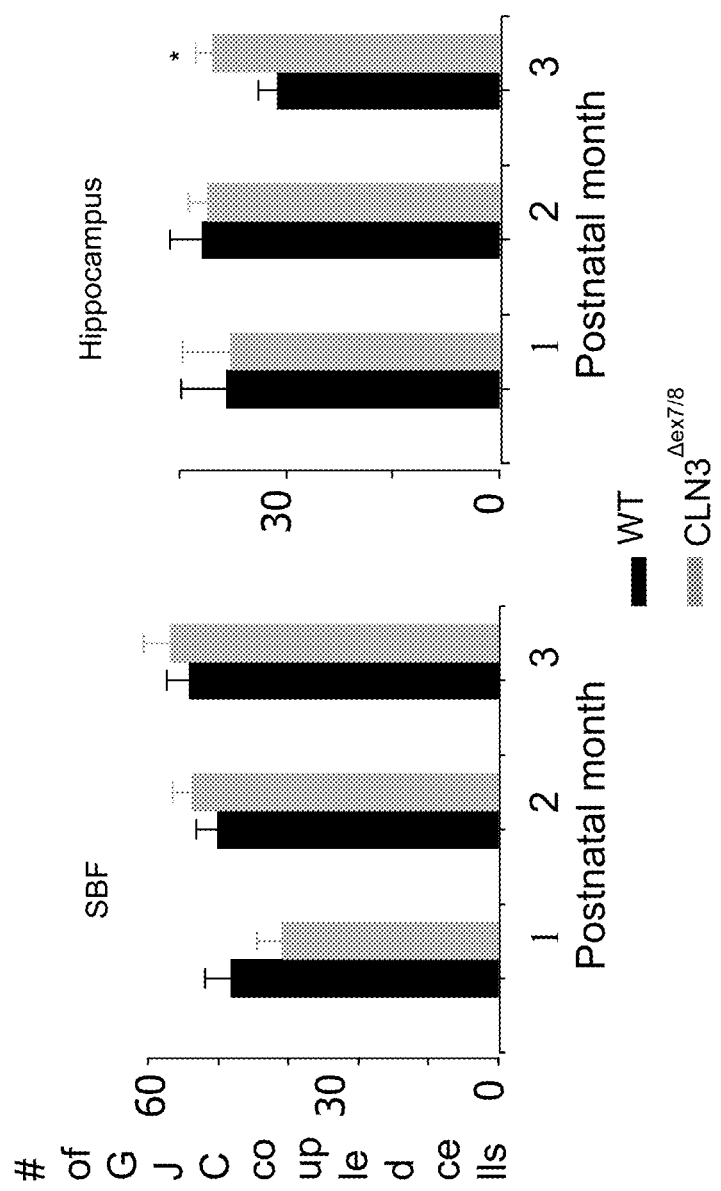
FIG. 5. Gap junction communication (GJC) is altered in CLN3$^{\Delta ex7/8}$ astrocytes in a region-dependent manner. Acute brain slices were prepared from CLN3$^{\Delta ex7/8}$ and WT mice, whereupon astrocyte GJC was quantitated by propagation of the gap junction permeable dye Alexa Fluor 350 (*, $p<0.05$ CLN3$^{\Delta ex7/8}$ vs. WT cells).
Figure 7:
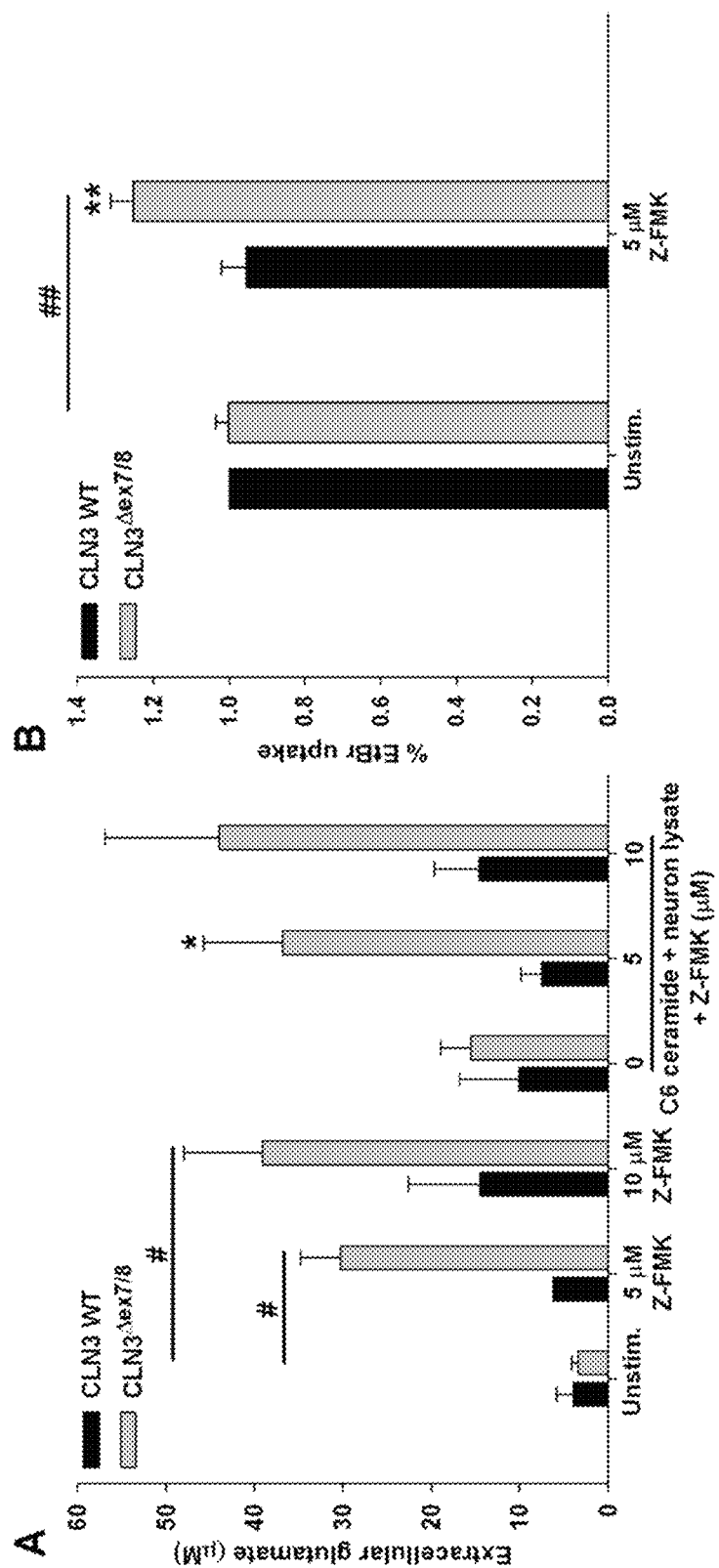
FIG. 7. CLN3$^{\Delta ex7/8}$ microglia exhibit constitutive caspase-1 activity that regulates glutamate release and corresponds to hemichannel activity. (A) Primary CLN3$^{\Delta ex7/8}$ and wild type (WT) microglia were pretreated with the caspase-1-specific inhibitor Z-WEHD-FMK (Z-FMK) for 1 h, whereupon cells were exposed to C6 ceramide (5 µM) and neuron lysates (1:5 dilution) for 24 h and extracellular glutamate measured. (B) Microglia were pretreated with the caspase-1-specific inhibitor Z-WEHD-FMK (Z-FMK) for 1 h followed by stimulation with C6 ceramide (5 µM) and neuron lysates (1:5 dilution) for 24 h, whereupon hemichannel activity was measured by ethidium bromide (EtBr) uptake over a 1 h period. Significant differences between CLN3$^{\Delta ex7/8}$ and WT microglia are indicated by asterisks (*, $p<0.05$; **, $p<0.01$), whereas changes between microglia treated with C6 ceramide+neuronal lysates only versus C6 ceramide+neuronal lysates+Z-FMK are denoted with hatched signs (#, $p<0.05$; ##, $p<0.01$).
Figure 8:
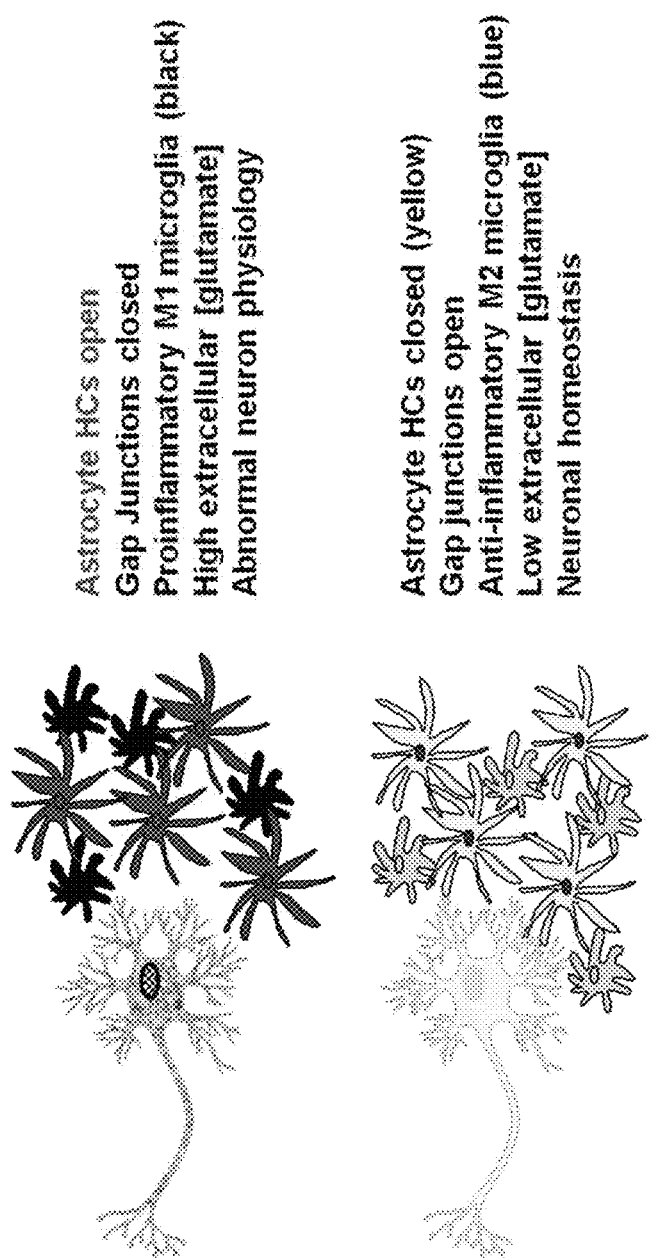
FIG. 8. Astrocyte hemi-channel (HC) and gap junction communication. Astrocytes display open HCs concomitant with altered homeostatic GJC and CLN3$^{\Delta ex7/8}$ microglia exhibit a pro-inflammatory phenotype. Together these responses likely contribute to neuronal loss during JNCL and inhibition of HC activity is expected to restore metabolic gradients and neuronal survival.

Astrocyte and microglial HCs allow for the direct communication between intra- and extracellular milieus, which can contribute to neuronal cell death by disrupting homeostatic gradients[14]. The data have revealed perturbations in astrocyte HC function in CLN3$^{\Delta ex7/8}$ mice that are evident as early as P30 (FIG. 5), well before neuronal loss is evident. It is expected that HC opening contributes to neurodegeneration during JNCL by disrupting homeostatic gradients that manifest as elevated extracellular glutamate levels and other metabolic disturbances. Similar observations have been noted with primary microglia and astrocytes recovered from CLN3$^{\Delta ex7/8}$ mice, where both glial types exhibit increased HC activity compared to their wild-type counterparts (FIG. 7). Therefore, targeting aberrant HC activity as a means to maintain neuronal homeostasis is expected to provide therapeutic benefits to individuals with JNCL, consistent with the utility established recent reports in mouse models altered HC activity in ALS, AD, and stroke[9,15,16]. Inhibiting aberrant HC activity in CLN3$^{\Delta ex7/8}$ mice is expected to restore homeostatic GJC, resulting in improvements in brain metabolism, neuronal survival, and behavioral readouts (FIG. 8). Disclosed herein are studies investigating the impact of INI-0602 on aberrant HC activity and glutamate release in primary microglia and astrocytes isolated from the brains of CLN3$^{\Delta ex7/8}$ mice. These studies also establish the roles of IL-1β and TNF-α in this process. Both IL-1β and TNF-α production is significantly increased in CLN3$^{\Delta ex7/8}$ microglia (FIG. 9) and both cytokines have been reported to induce HC opening[17]. However, the functional impact of IL-1β and TNF-α on stimulating glial HC activity in the context of CLN3 mutation has not been disclosed in the art.

Mixed glial cultures are prepared from CLN3$^{\Delta ex7/8}$ and C57BL/6 wild-type mice, whereupon purified microglia and astrocytes are recovered by differential shaking[18,19]. Since CLN3$^{\Delta ex7/8}$ astrocytes exhibit constitutive HC activity (FIG. 7), CLN3$^{\Delta ex7/8}$ and WT astrocytes are exposed to various concentrations of the HC inhibitor INI-0602 (1-100 μM) for either 6 or 24 hours, whereupon HC activity is assessed by ethidium bromide (EtBr) uptake assays, as has been described[6]. An identical treatment strategy is employed for CLN3$^{\Delta ex7/8}$ microglia. However, since aberrant HC opening is only observed following exposure to C6 ceramide+neuronal lysates and not under resting conditions, cells is treated with these stimuli in combination with INI-0602, whereupon HC activity is assessed.

Figure 9:
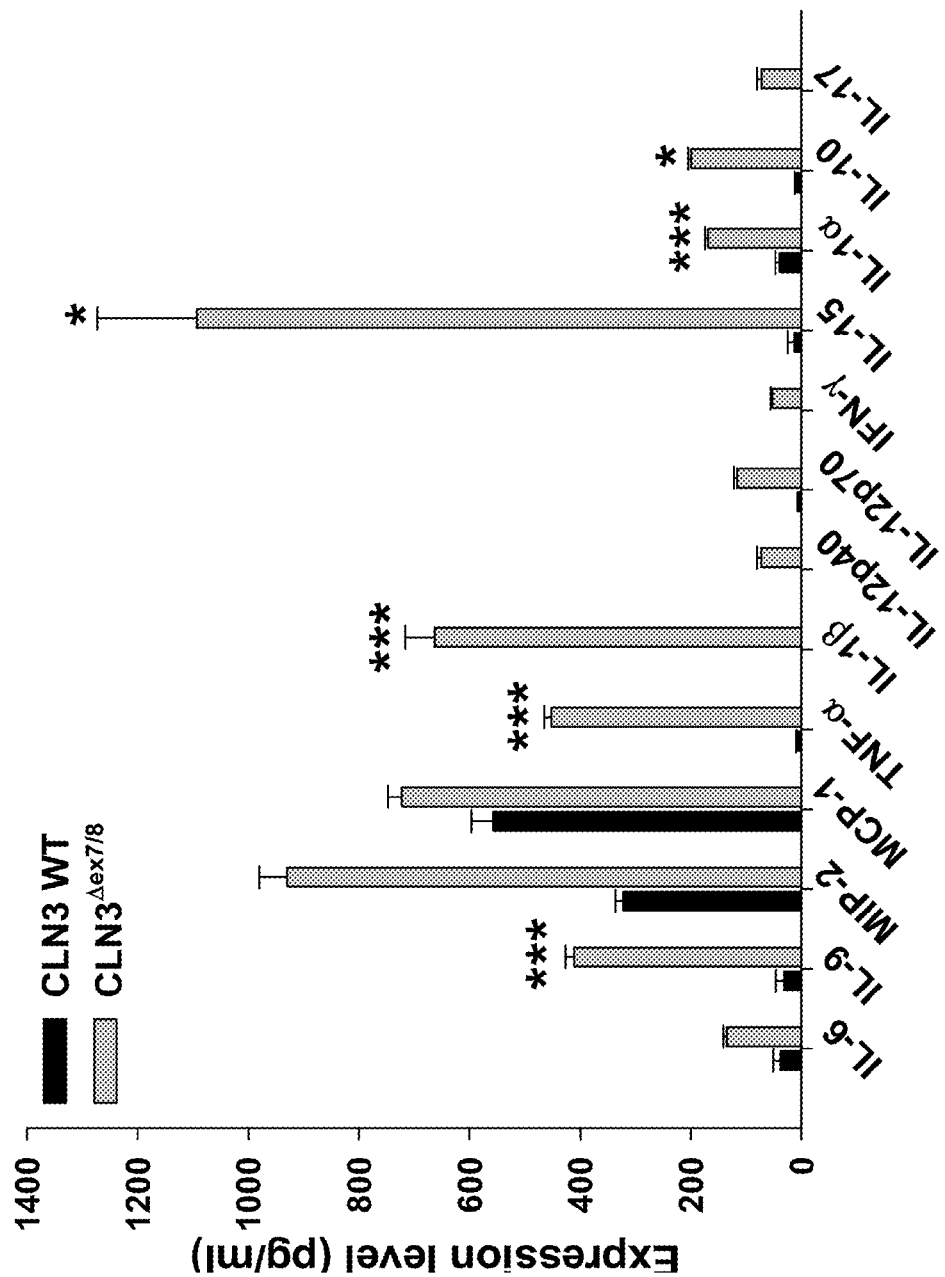
FIG. 9. CLN3$^{\Delta ex7/8}$ microglia are primed towards a proinflammatory phenotype. Inflammatory mediator production by primary microglia from CLN3$^{\Delta ex7/8}$ and WT mice was measured after exposure to 20 µM C6 ceramide+neuron lysates for a 24-hour period (*, $p<0.05$; ***, $p<0.001$).
Figure 10:
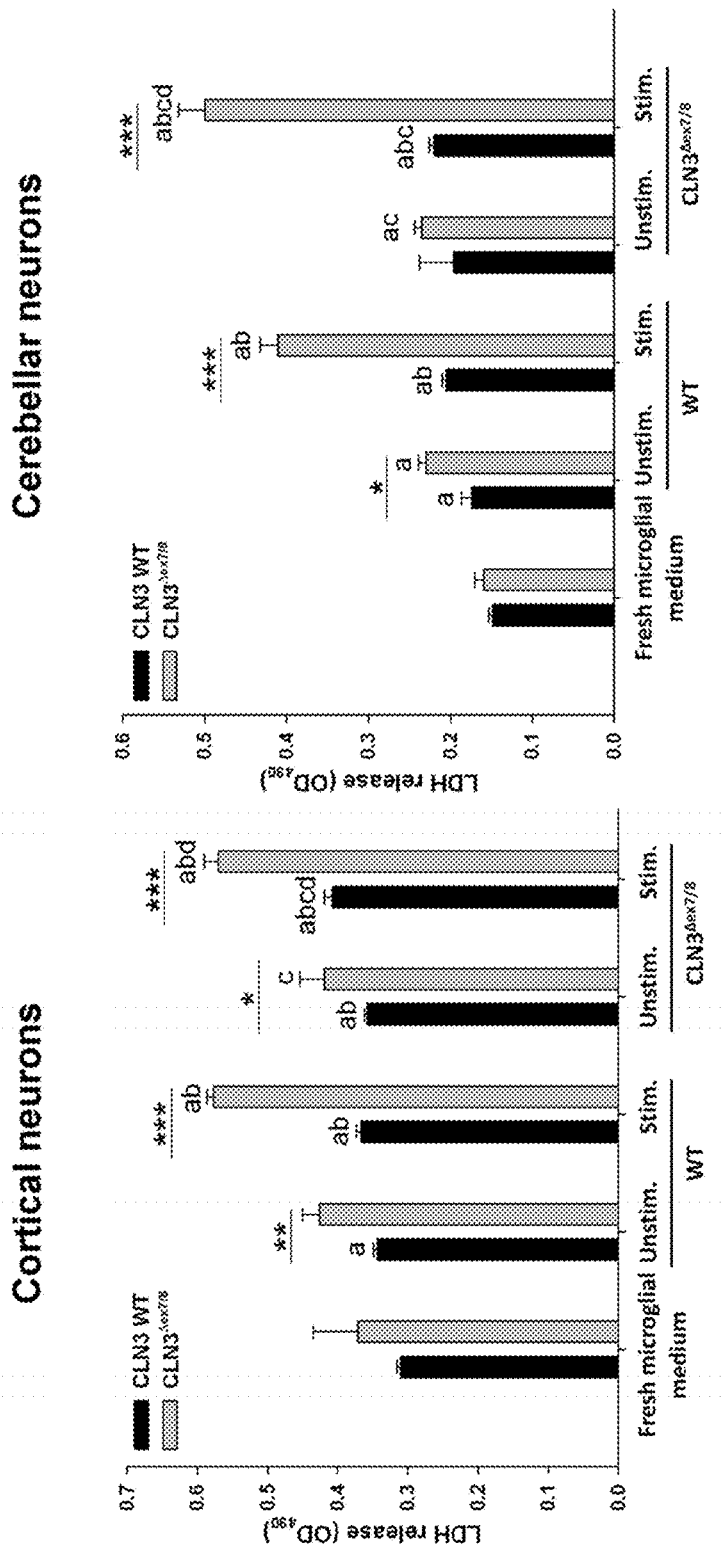
FIG. 10. CLN3$^{\Delta ex7/8}$ neurons are more sensitive to microglial-induced cytotoxicity. Primary cortical and cerebellar neurons from CLN3$^{\Delta ex7/8}$ and WT mice were exposed to conditioned medium collected from CLN3$^{\Delta ex7/8}$ or WT microglia after stimulation for 24 hours with C6 ceramide (5 µM)+neuronal lysate (1:5 dilution; Stim). Neurons were incubated with microglial-conditioned medium for 24 hours, whereupon toxicity was assessed by quantitating LDH release. Asterisks represent significant differences between CLN3$^{\Delta ex7/8}$ and WT neurons (*, $p<0.05$; , $p<0.01$; *, $p<0.001$) and letters depict significant differences between the various treatment groups (a-fresh microglial medium, b-unstimulated WT medium, c-stimulated WT medium, and d-unstimulated CLN3$^{\Delta ex7/8}$ medium).

A main consequence of HC opening is glutamate release, and glutamate is significantly elevated in the brains of JNCL patients as well as in CLN3-deficient mice[3,4,20]. Data indicate that glutamate release from CLN3$^{\Delta ex7/8}$ microglia is enhanced compared to WT cells (FIG. 10), which coincides with increased HC activity (FIG. 7). Both IL-1β and TNF-α production are dramatically elevated in CLN3$^{\Delta ex7/8}$ microglia (FIG. 9), and TNF-α has been shown to trigger microglial HC opening[17], providing a link between these processes. In these experiments, primary microglia and astrocytes from CLN3$^{\Delta ex7/8}$ and WT mice are treated with the HC inhibitor INI-0602 to determine whether this impairs glutamate release. Extracellular glutamate levels are quantitated using a fluorescence-based glutamate oxidase assay as previously described (FIG. 10). To demonstrate a key role for the autocrine/paracrine actions of IL-1β and/or TNF-α on HC activity and glutamate release in CLN3$^{\Delta ex7/8}$ microglia, cells are pre-treated with neutralizing antibodies against either cytokine or isotype-matched antibodies as controls to determine whether this attenuates HC opening and glutamate release. Unlike microglia, astrocytes are not a major source of IL-1β and TNF-α[21]. Therefore, the potential paracrine action of these cytokines on HC activity in CLN3$^{\Delta ex7/8}$ and WT astrocytes are examined using two complementary methods. First, CLN3$^{\Delta ex7/8}$ and WT astrocytes are exposed to various concentrations of recombinant mouse IL-1β and TNF-α (1-100 ng/ml) for either 6 or 24 hours, whereupon HC activity and glutamate release are evaluated as described above. Second, CLN3$^{\Delta ex7/8}$ microglia-astrocyte co-cultures are prepared and the effect of paracrine IL-1β and TNF-α produced by the former on astrocyte HC function is evaluated. Microglia are differentiated from astrocytes by labeling cells with CellTracker Blue and CellTracker Green, respectively, whereupon EtBr uptake (red) is visualized in microglia (pink) versus astrocytes (yellow/orange). Similar IL-1β and TNF-α neutralizing antibody experiments are performed as described above to assess the relative impact of these cytokines on astrocyte HC opening.

Example 14

Direct Assessment of HC Blockade

Figure 6:
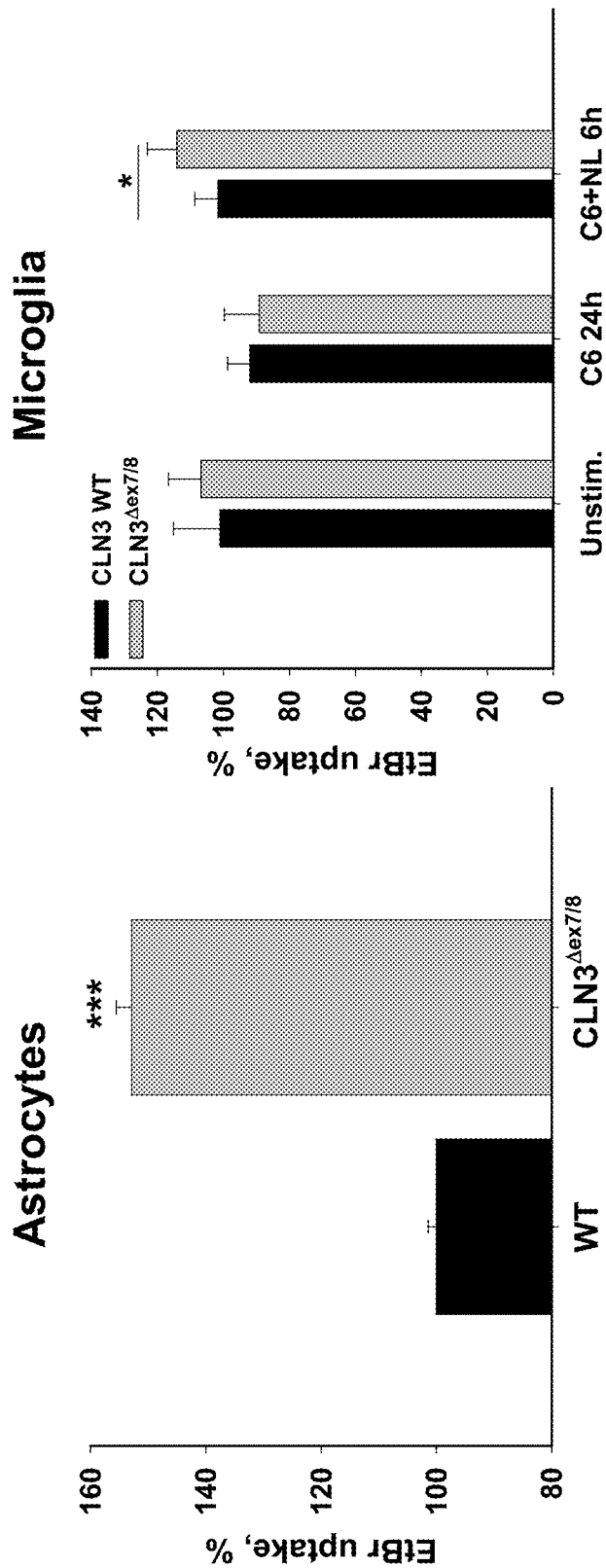
FIG. 6. CLN3$^{\Delta ex7/8}$ astrocytes and microglia display elevated hemi-channel (HC) activity. HC activity in primary astrocytes and microglia from CLN3$^{\Delta ex7/8}$ and WT mice was measured by EtBr uptake at 24 hours (*, $p<0.05$; ***, $p<0.001$). C6, 20 µM ceramide; NL, neuron lysate.

To directly assess whether HC blockade with INI-0602 will restore astrocyte GJC and electrophysiological properties in CLN3$^{\Delta ex7/8}$ mice to WT levels in vivo, animals are treated with INI-0602 and HC/GJC activity and electrophysiological parameters are monitored in acute brain slices using standard methodologies[6,22]. For these experiments, CLN3$^{\Delta ex7/8}$ and WT mice receive i.p. injections of INI-0602 (1, 10, or 50 mg/kg) or vehicle (PBS) every other day, beginning at P30 and continuing until P60, whereupon animals are sacrificed and acute brain slices processed for analysis. Initial studies are focused on a single time point early in the disease process, since data clearly demonstrate significant perturbations in HC/GJC and electrophysiological properties in numerous brain regions (FIGS. 5, 6, and 11), which is believed to be deleterious to neuron survival. If INI-0602 is capable of returning these abnormalities in CLN3$^{\Delta ex7/8}$ mice to normal, prolonged treatment is examined to determine if it leads to significant improvements in neuronal survival at later intervals (i.e., 7 months). INI-0602 rapidly accumulates in the CNS and is still detectable at 3 hours after administration. The neuroprotective properties associated with INI-0602 administration every other day indicates that the compound exerts potent and long-lasting effects within the CNS[9]. Continued INI-0602 dosing proved highly safe, as no adverse effects on blood or urine profiles were observed after a 7-month treatment period.

Figure 11:
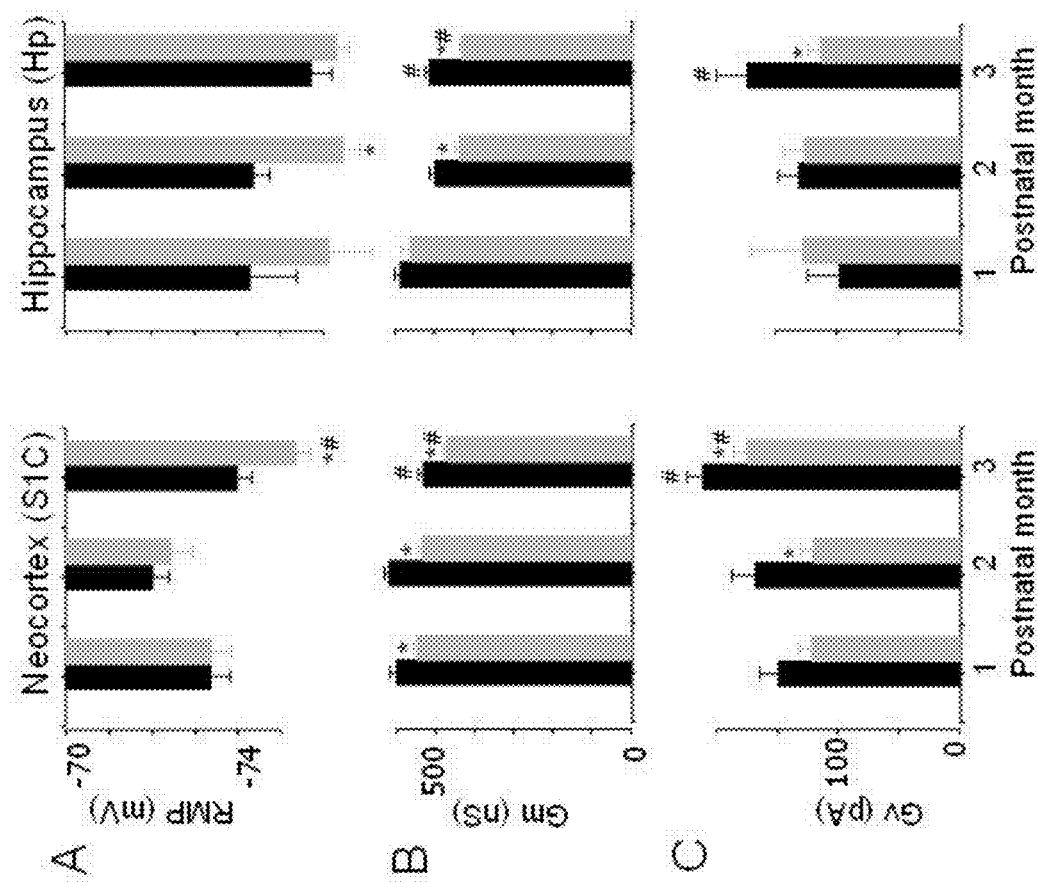
FIG. 11. CLN3$^{\Delta ex7/8}$ astrocytes display electrophysiological abnormalities. Whole cell-patch clamp recordings of astrocytes from acute brain slices of CLN3$^{\Delta ex7/8}$ and WT mice at postnatal days 30, 60, and 90 revealed significant changes in resting membrane potential (RMP), membrane conductance (Gm) and voltage-dependent conductance (Gv). (*, $p<0.05$ WT vs. CLN3$^{\Delta ex7/8}$; #, $p<0.05$ between WT over time.)

After the 30-day treatment regimen, the impact of INI-0602 on HC and GJC in living brain slices prepared from CLN3$^{\Delta ex7/8}$ and WT mice is determined[6]. Briefly, animals are euthanized by cervical dislocation and immediately decapitated, whereupon the brain is quickly removed and bathed in ice-cold artificial CSF (ACSF) buffered with carbogen (95% $O_2$ and 5% $CO_2$). Next, horizontal brain slices (300-400 μm thick) are cut using a vibrating blade microtome and held in ACSF containing CellTracker Blue dye to facilitate cell identification. Whole-cell patch-clamp recordings are performed on individual astrocytes in brain slices from CLN3$^{\Delta ex7/8}$ or WT mice±INI-0602, where the GJ-permeable dye Alexa Fluor 350 is added to the intracellular recording solution to evaluate the degree of cell coupling. The distance of dye spread from a single microinjected cell to neighboring cells is quantitated and is reflective of the extent of GJC. It is expected that closing HCs with INI-0602 action will restore protective GJC, which is supported by our data (FIG. 18). This is expected to translate into delayed neuronal cell death, since GJC is involved in detoxification of the extracellular milieu. It is important to note that as astrocytes mature in vivo, their degree of GJC increases to form syncytial networks. Electrophysiological studies demonstrate that although GJC increases over the span of one month in WT mice, this does not occur in CLN3$^{\Delta ex7/8}$ animals, which coincides with reduced conductance, increased membrane resistance, and HC opening (FIG. 11). These findings indicate that astrocytes remain in an immature state in the context of CLN3 mutation and could represent a key pathological event that underlies the multiple defects observed during JNCL. INI- 0602 HC blockade is expected to return these astrocytic parameters in CLN3$^{\Delta ex7/8}$ mice to approximately WT levels. Most relevant to JNCL is the ability of GJC to detoxify glutamate. Prevention of HC opening by INI-0602 is expected to facilitate glutamate uptake and elimination via GJC, leading to reduced glutamate concentrations and less neuron excitotoxicity, which would be expected to positively affect the JNCL disease course. Glutamate levels are measured in CLN3$^{\Delta ex7/8}$ and WT brain slices+INI-0602 as described herein.

Example 15

HC Activity

To evaluate HC activity, Ethidium Bromide (EtBr; 2.5 μM) is added to the bath solution during brain slice preparation as previously described[6]. EtBr has a small molecular weight that enables its uptake into cells when HC are open. It is thought that open HCs are deleterious to brain homeostasis, since this would allow for the disruption of physiologic gradients between the intra- and extracellular milieus[23,24]. Data disclosed herein show aberrant HC activity in CLN3$^{\Delta ex7/8}$ mice (FIG. 5), consistent with exaggerated glutamate release. Therefore, it is expected that INI-0602 will block HC activity in CLN3$^{\Delta ex7/8}$ mice that will lead to reductions in glutamate levels. To assess this possibility, glutamate levels are measured by two approaches. First, living brain slices are incubated in ACSF for 1 hour, whereupon glutamate levels are measured using a fluorescent glutamate oxidase assay. Second, brain slices are homogenized to quantitate total glutamate levels, which are normalized to total protein to account for subtle differences in slice size. By virtue of its ability to attenuate HC opening, it is expected that INI-0602 treatment of CLN3$^{\Delta ex7/8}$ mice will lead to reductions in glutamate, which is independently confirmed by MR spectroscopy. We will also monitor the safety profile of INI-0602 by performing a CBC and blood chemistry panels are also performed at weekly intervals and body weight monitored on a daily basis to ensure the safety of the methods according to the disclosure. This, in conjunction with MR spectroscopy studies to evaluate brain metabolites in wild-type animals treated with INI-0602 will allow assessment of whether the compound exhibits any adverse side effects in the CNS or periphery. However, no toxicity is expected with INI-0602 administration over a significant range of dosages, since animals have received continuous dosing for up to 7 months without any adverse effects[9].

Example 16

MR Spectroscopy and Diffusion Tensor Imaging Measures of HC Blockade

MRI can be acquired as three-dimensional data sets with very accurate depictions of anatomy, physiology, and biochemistry in a relatively short time interval[25,26]. A benefit of high resolution MRI scans is the ability to determine the volume of specific lesions in addition to measuring tissue relaxivity, indices of cellular changes using diffusion tensor imaging (DTI)[25], quantitative measures of diffusion, and biochemical changes using MR spectroscopy. Lack of exposure to ionizing radiation makes this an ideal methodology for serial non-invasive studies.

Figure 12:
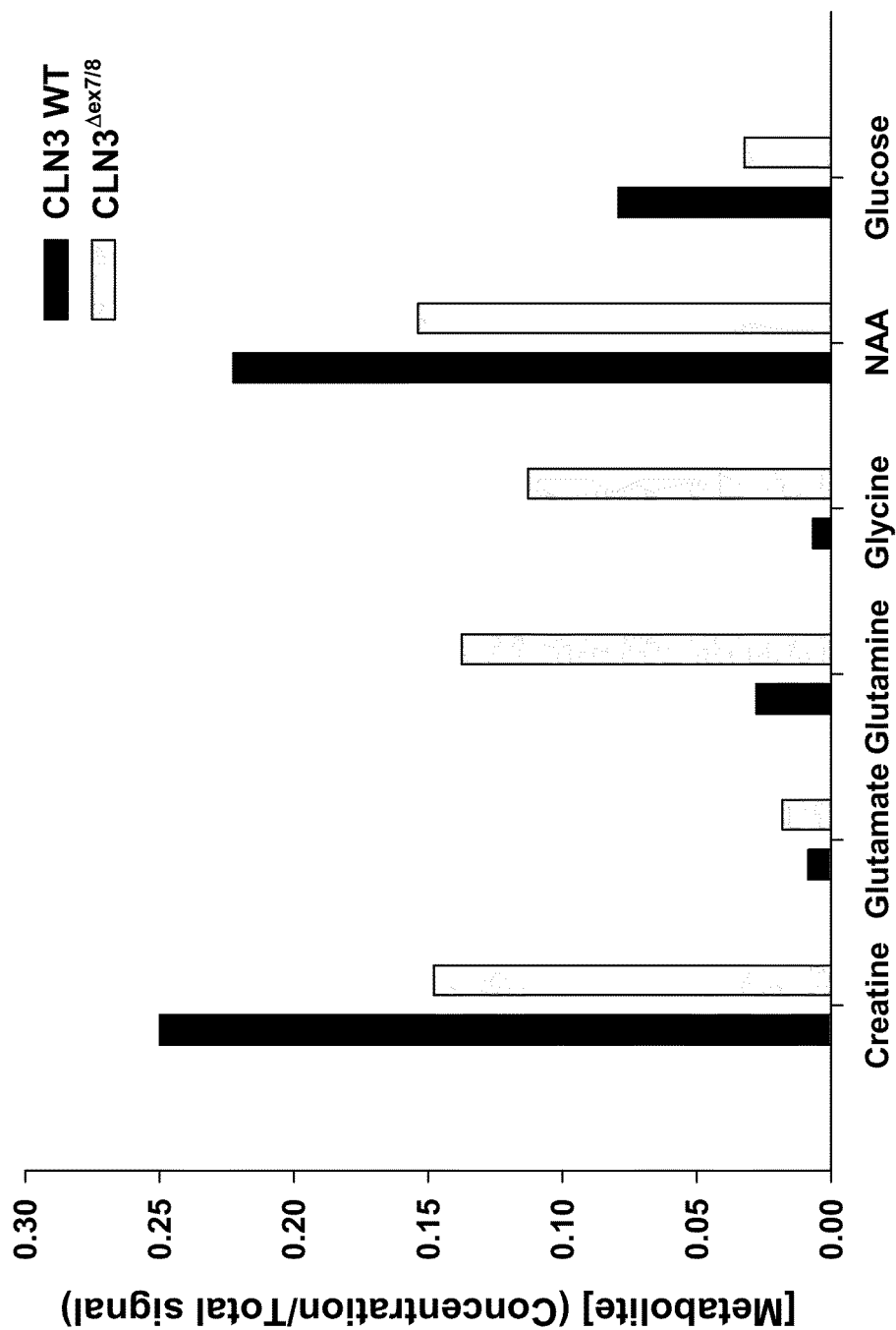
FIG. 12. Striatum of CLN3$^{\Delta ex7/8}$ mice displays early metabolic disturbances. MR spectroscopy was utilized to non-invasively compare the metabolic profile within the striatum of CLN3$^{\Delta ex7/8}$ and WT mice at postnatal day 60.

$^1$H magnetic resonance spectroscopy imaging is a non-invasive method to obtain direct metabolic information from living animals, in which spectra are obtained from multiple voxels simultaneously. Proton MR spec-visible metabolites are primarily N-acetyl aspartate (NAA), choline (Cho), creatine (Cre), glutamate (Glu), glutamine (Gln), and myo-inositol (mI)[27]. However, recent advances in curve fitting methodology also allow for the measurement of low-level metabolites, including gamma-amino butyric acid (GABA), glucose, glycine, alanine, aspartic acid, and taurine. Studies have demonstrated the utility of single-voxel proton MR spectroscopy to demonstrate changes in the brain metabolome during JNCL, in particular highlighting elevations in glutamate concomitant with reductions in GABA and NAA[7]. NAA is synthesized exclusively in the mitochondria of neurons and is widely used as a marker of neuronal integrity, whereby neuronal cell death results in an irreversible loss of NAA[28]. Creatine (Cre) is part of the creatine kinase energy metabolism buffer system used to maintain ATP levels in times of acute mismatch between oxidative ATP supply and ATP demand. Therefore, the [Cre] reflects the health of systematic energy use and storage[29]; however, Cre has also been implicated in osmoregulation and studies disclosed herein reveal changes in Cre levels in CLN3$^{\Delta ex7/8}$ mice that correlate with abnormal DTI measurements, the latter reflecting cell size, shape, and overall order of white matter tracts. Glu and Gln are elevated in the brains of JNCL patients and our studies have demonstrated increases of both in the striatum of CLN3$^{\Delta ex7/8}$ mice at P60 (FIG. 12) that directly correlates with aberrant GJC/HC activity. GABA is an inhibitory transmitter and its metabolism is tightly linked to glutamate. Studies in CLN3 knock-out (KO) mice have demonstrated an imbalance in the glutamate/GABA ratio noted as early as 1 month of age[30]. Therefore, there is existing data supporting metabolic abnormalities during early JNCL; however, there are distinctions between this prior study and the MR spectroscopy experiments disclosed herein. First, earlier work was performed with CLN3 KO mice[30], whereas the work disclosed herein uses CLN3$^{\Delta ex7/8}$ animals, which more accurately model the most common genetic mutation in JNCL patients. Second, brain metabolism is monitored in real-time in living animals, whereas the prior report analyzed brain extracts post-mortem by a HMR-based approach[30]. The latter distinction enables the technologies disclosed herein to provide a unique perspective in evaluating the effect of HC blockade on the metabolome in specific brain regions of CLN3$^{\Delta ex7/8}$ mice.

Two 7-Tesla (7T) small-animal magnetic resonance imaging and spectroscopy (MRI/S) systems (7T/21 cm Biospec, and a 7T/16 cm Pharmascan, Bruker Biospin, Karlshure, Germany) are operational at the University of Nebraska Medical Center. Mice are anesthetized with a 1.5% isoflurane in a 70% nitrous oxide/30% oxygen mixture and positioned in a custom-made stereotactic holder equipped with a SA instruments model 1025 MRI-compatible physiological monitoring system (Model 1025, SA Instruments, Stony Brook, N.Y.). Monitoring capabilities include respiratory, temperature, and EKG monitors, with optional pulse oximetry and $CO_2$ monitors as needed. Core body temperature of anesthetized mice is maintained by a warm air delivery system developed for the Pharmascan MRI system and is designed to be compatible with the Biospec MRI system. The initial set-up for all MRI studies includes a 3-plane locator scan. Localization and initial shimming using a novel field mapping method[31] requires about 10 minutes. Once the mouse is in position and shimmed, experiments are performed as described below. Results from QA phantoms are compared to animals to verify accuracy and random error measurements. Initial analyses are done using regions of interest (ROI) located in the hippocampus and striatum of CLN3$^{\Delta ex7/8}$ and WT mice. Analyses are limited to these brain areas for two reasons. First, MR spectroscopy data can be collected during the same scanning session because the striatum and hippocampus lie within the same focal plane. Second, other brain regions of interest (i.e., thalamus, visual cortex) require a separate scan to reposition the head in the MRI instrument and because the length of time required to capture sufficiently sensitive MR spectroscopy data is rather long (i.e., 0.5 hours/region), including additional brain regions is not feasible from the perspectives of both time and cost.

Results have revealed alterations in glutamate, glutamine, GABA, NAA, and total glucose in the striatum and hippocampus of CLN3$^{\Delta ex7/8}$ mice at P60 (FIG. 11), which corroborate MR spectroscopy findings reported in human JNCL[7]. This finding demonstrates the reliability of the CLN3$^{\Delta ex7/8}$ mouse to accurately model changes in brain metabolism that are pertinent to human disease. MR spectroscopy is used to determine whether inhibition of aberrant HC activity by INI-0602 in CLN3$^{\Delta ex7/8}$ mice restores the CNS metabolome to levels characteristic of WT brain. In particular, the hippocampus and striatum are areas of focus because studies disclosed herein have shown abnormal GJC and electrophysiological properties in CLN3$^{\Delta ex7/8}$ animals as well as metabolic disturbances.

CLN3$^{\Delta ex7/8}$ and WT mice receive i.p. injections of INI-0602 (1, 10, or 50 mg/kg) or vehicle (PBS) every other day, beginning at P30 and continuing until P60, whereupon the impact of HC blockade on metabolic profiles of the hippocampus and striatum is measured by MR spectroscopy. These experiments are performed side-by-side with the studies examining GJC/HC activity in acute brain slices to assess whether INI-0602 coordinately regulates both outcomes. This links the studies establishing that aberrant HC opening leads to the disruption of homeostatic CNS gradients, which over time, contributes to neuronal loss through elevated glutamate and reduced GABA levels. This understanding is supported by the fact that JNCL is associated with widespread metabolic disruptions and abnormal concentrations of numerous metabolites[4]. Blocking aberrant HC activity in CLN3$^{\Delta ex7/8}$ mice is expected to restore homeostatic glutamate, glutamine, and GABA levels with a concomitant increase in NAA, indicative of neuronal sparing. The metabolic profile of CLN3$^{\Delta ex7/8}$ mice following INI-0602 treatment is expected to closely approximate that observed in vehicle-treated WT animals. The effect of INI-0602 on the brain metabolome of WT mice is also assessed, as a measure of safety. As mentioned above, the safety record of INI-0602 is excellent, with no evidence of toxicity observed during a 7-month treatment period in mouse models of ALS and AD[9]. In addition to one-month treatment periods of INI-0602 to induce HC blockade in CLN3$^{\Delta ex7/8}$ mice, longer dosing schedules are contemplated in mouse and other vertebrates, including mammals such as man. Additionally, the longevity of INI-0602 action after treatment cessation is also assessed. Data disclosed herein reveals significant alterations in numerous metabolites in the brains of CLN3$^{\Delta ex7/8}$ mice. Studies disclosed herein also demonstrate aberrant astrocyte and microglial activation, both of which play key roles in regulating neuronal homeostasis.

Diffusion tensor imaging (DTI) is a MR-based technique that enables the visualization and orientation of white matter tracts[32]. The organization of axons in parallel bundles restricts the diffusion of water molecules transverse to their direction, with relatively free diffusion along the fiber axis. DTI-measurable parameters include the mean diffusivity ($D_{av}$), the individual components of the diagonalized diffusion tensor (eigenvalues $\lambda_1$, $\lambda_2$, and $\lambda_3$), and diffusion anisotropy. The diffusion anisotropy value can be used to define the extent of water diffusion and provide information regarding the degree of white matter tract organization. One of the most widely used metrics of diffusion anisotropy is referred to as fractional anisotropy (FA) and is scaled from 0 (isotropic, meaning that the diffusion of water is equal in all directions due to spherical cell shape) to 1 (diffusion in only one direction due to an infinitely long, infinitely narrow cell shape). Experiments are conducted to determine whether CLN3$^{\Delta ex7/8}$ mice display early DTI changes that may be attributed to aberrant HC activity, which would be confirmed by the ability of INI-0602 to restore DTI readings to those typical of WT animals. DTI data disclosed herein show clear FA abnormalities CLN3$^{\Delta ex7/8}$ animals at P60, both within white matter tracts (striatum and corpus callosum) and grey matter (frontal and cerebral cortex, hippocampus, and dentate gyrus; FIG. 13). For example, a reduction in white matter FA values is indicative of damage, as the organization of white matter bundles or myelin sheaths is disrupted, which is depicted by decreased FA values in the striatum and corpus callosum of CLN3$^{\Delta ex7/8}$ mice (FIG. 9). In contrast, FA increases in grey matter are reflective of damage as synapses are pruned. The findings that fractional anisotropy values are elevated in numerous grey matter regions of CLN3$^{\Delta ex7/8}$ mice (i.e., frontal and cerebral cortex, hippocampus, and dentate gyrus), indicate the onset of synaptic damage as early as 2 months of age, well before overt neuron loss has been reported in these animals (i.e., 5-7 months)[35,36] (FIG. 19). Activated microglia have recently been implicated in synaptic pruning[33], and the data disclosed herein demonstrate aberrant microglial proinflammatory activity in CLN3$^{\Delta ex7/8}$ mice, indicating that microglia contribute to neuronal damage during early JNCL. Also, creatine has been implicated in brain osmoregulation and DTI measures demonstrate aberrant water patterns in the brains of CLN3$^{\Delta ex7/8}$ mice at P60 (FIG. 9). Therefore, a link also exists between osmoregulation and GJC/HC activity. For example, GJC is known to play important roles in cellular volume control and because HCs are opened in young CLN3$^{\Delta ex7/8}$ mice, combined with reduced creatine levels, sets the stage for osmotic imbalances, as indicated by the results disclosed herein. The methods disclosed herein inhibit aberrant HC action in individuals suffering from JNCL, as modeled by CLN3$^{\Delta ex7/8}$ mice, and these methods are expected to affect numerous pathological sequelae observed during JNCL, including glial and metabolic disturbances as well as behavioral aspects that represent a significant challenge for patients and their families[34]. The beneficial effects of manipulating cellular communication networks achieved by the methods of the disclosure depend, in part, on the role of the GJC/HC balance in regulating basal homeostatic processes and neuronal integrity within the CNS.

References for Examples 13-16

1. Laird D W. Life cycle of connexins in health and disease. Biochem J. 2006; 394:527-543.
2. Scemes E. Nature of plasmalemmal functional "hemichannels". Biochim Biophys Acta. 2011.
3. Puranam K, Qian W H, Nikbakht K, et al. Upregulation of Bcl-2 and elevation of ceramide in Batten disease. Neuropediatrics. 1997; 28(1):37-41.

4. Salek R M, Pears M R, Cooper J D, et al. A metabolomic comparison of mouse models of the Neuronal Ceroid Lipofuscinoses. J Biomol NMR. 2011; 49(3-4):175-184.
5. Orellana J A, Shoji K F, Abudara V, et al. Amyloid beta-induced death in neurons involves glial and neuronal hemi-channels. J. Neurosci. 2011; 31(13):4962-4977.
6. Karpuk N, Burkovetskaya M, Fritz T, Angle A, Kielian T. Neuroinflammation leads to region-dependent alterations in astrocyte gap junction communication and hemi-channel activity. J. Neurosci. 2011; 31(2):414-425.
7. Brockmann K, Pouwels P J, Christen H J, Frahm J, Hanefeld F. Localized proton magnetic resonance spectroscopy of cerebral metabolic disturbances in children with neuronal ceroid lipofuscinosis. Neuropediatrics. 1996; 27(5):242-248.
8. Giaume C, Koulakoff A, Roux L, Holcman D, Rouach N. Astroglial networks: a step further in neuroglial and gliovascular interactions. Nat Rev Neurosci. 2010; 11(2):87-99.
9. Takeuchi H, Mizoguchi H, Doi Y, et al. Blockade of gap junction hemi-channel suppresses disease progression in mouse models of amyotrophic lateral sclerosis and Alzheimer's disease. PLoS One. 2011; 6(6):e21108.
10. Osorio N S, Sampaio-Marques B, Chan C H, et al. Neurodevelopmental delay in the Cln3Deltaex7/8 mouse model for Batten disease. Genes Brain Behav. 2009; 8(3):337-345.
11. Getty A L, Pearce D A. Interactions of the proteins of neuronal ceroid lipofuscinosis: clues to function. Cell Mol Life Sci. 2011; 68(3):453-474.
12. Parpura V, Heneka M T, Montana V, et al. Glial cells in (patho)physiology. J. Neurochem. 2012; 121(1):4-27.
13. Bates T E, Strangward M, Keelan J, Davey G P, Munro P M, Clark J B. Inhibition of N-acetylaspartate production: implications for 1H MRS studies in vivo. Neuroreport. 1996; 7(8):1397-1400.
14. Kielian T. Glial connexins and gap junctions in CNS inflammation and disease. J. Neurochem. 2008.
15. Davidson J O, Green C R, Nicholson L F, et al. Connexin hemi-channel blockade improves outcomes in a model of fetal ischemia. Ann Neurol. 2012; 71(1):121-132.
16. Danesh-Meyer H V, Kerr N M, Zhang J, et al. Connexin43 mimetic peptide reduces vascular leak and retinal ganglion cell death following retinal ischaemia. Brain. 2012; 135:506-520.
17. Retamal M A, Froger N, Palacios-Prado N, et al. Cx43 hemi-channels and gap junction channels in astrocytes are regulated oppositely by proinflammatory cytokines released from activated microglia. J. Neurosci. 2007; 27(50):13781-13792.
18. Hanamsagar R, Tones V, Kielian T. Inflammasome activation and IL-1beta/IL-18 processing are influenced by distinct pathways in microglia. J. Neurochem. 2011; 119(4):736-748.
19. Esen N, Tanga F Y, DeLeo J A, Kielian T. Toll-like receptor 2 (TLR2) mediates astrocyte activation in response to the Gram-positive bacterium *Staphylococcus aureus*. J. Neurochem. 2004; 88(3):746-758.
20. Puranam K L, Guo W X, Qian W H, Nikbakht K, Boustany R M. CLN3 defines a novel antiapoptotic pathway operative in neurodegeneration and mediated by ceramide. Mol Genet Metab. 1999; 66(4):294-308.
21. Holm T H, Draeby D, Owens T. Microglia are required for astroglial Toll-like receptor 4 response and for optimal TLR2 and TLR3 response. Glia. 2012; 60(4):630-638.
22. Karpuk N, Burkovetskaya M, Kielian T. Neuroinflammation alters voltage-dependent conductance in striatal astrocytes. J. Neurophysiol. 2012.
23. Bargiotas P, Monyer H, Schwaninger M. Hemi-channels in cerebral ischemia. Curr Mol. Med. 2009; 9:186-194.
24. Thompson R J, Macvicar B A. Connexin and pannexin hemi-channels of neurons and astrocytes. Channels. 2008; 2(2):81-86.
25. Pautler R G. Mouse MRI: concepts and applications in physiology. Physiology (Bethesda). 2004; 19:168-175.
26. Chatziioannou A F. Instrumentation for molecular imaging in preclinical research: Micro-PET and Micro-SPECT. Proc Am Thorac Soc. 2005; 2:533-536, 510-511.
27. Valenzuela M J, Sachdev P. Magnetic resonance spectroscopy in AD. Neurology. 2001; 56(5):592-598.
28. Urenjak J, Williams S R, Gadian D G, Noble M. Specific expression of N-acetylaspartate in neurons, oligodendrocyte-type-2 astrocyte progenitors, and immature oligodendrocytes in vitro. J. Neurochem. 1992; 59(1):55-61.
29. Miller B L. A review of chemical issues in $^1$H NMR spectroscopy: N-acetyl-L-aspartate, creatine and choline. NMR Biomed. 1991; 4(2):47-52.
30. Pears M R, Cooper J D, Mitchison H M, Mortishire-Smith R J, Pearce D A, Griffin J L. High resolution 1H NMR-based metabolomics indicates a neurotransmitter cycling deficit in cerebral tissue from a mouse model of Batten disease. J Biol. Chem. 2005; 280(52):42508-42514.
31. Miyasaka N, Takahashi K, Hetherington H P. Fully automated shim mapping method for spectroscopic imaging of the mouse brain at 9.4 T. Magn Reson Med. 2006; 55(1):198-202.
32. Mori S, Zhang J. Principles of diffusion tensor imaging and its applications to basic neuroscience research. Neuron. 2006; 51(5):527-539.
33. Stevens B, Allen N J, Vazquez L E, et al. The classical complement cascade mediates CNS synapse elimination. Cell. 2007; 131(6):1164-1178.
34. Adams H R, Beck C A, Levy E, et al. Genotype does not predict severity of behavioural phenotype in juvenile neuronal ceroid lipofuscinosis (Batten disease). Dev Med Child Neurol. 2010; 52(7):637-643.
35. Pontikis C C, Cella C V, Parihar N, et al. Late onset neurodegeneration in the Cln3−/− mouse model of juvenile neuronal ceroid lipofuscinosis is preceded by low level glial activation. Brain Res. 2004; 1023(2):231-242.
36. Pontikis C C, Cotman S L, MacDonald M E, Cooper J D. Thalamocortical neuron loss and localized astrocytosis in the Cln3Deltaex7/8 knock-in mouse model of Batten disease. *Neurobiol Dis.* 2005; 20(3):823-836.

All references cited herein are hereby incorporated by reference in their entireties, or with respect to particular passages, as would be apparent from the context of the citation.

From the foregoing it will be appreciated that, although specific embodiments of the disclosure have been described herein for purposes of illustration, various modifications may be made without deviating from the spirit and scope of the disclosure.

What is claimed is:

1. A method of reducing the rate of development of Juvenile Neuronal Ceroid Lipofuscinosis comprising administering an effective amount of a phosphodiesterase-4 inhibitor and an effective amount of INI-0602 to a subject.

2. The method according to claim 1 wherein the phosphodiesterase-4 inhibitor is selected from the group consisting of propentofylline, apremilast, cilomilast, diazepam, drotaverine, etazolate, filaminast, glaucine, HT-0712, ibudilast, luteolin, mesembrine, mesembrenone, pentoxifylline, piclamilast, rolipram, roflumilast, ronomilast, RPL-554, GSK256066, chlorbipram, MK-0952, MK-0359, MK-0873, KCA-1490, N-(3,5-dichloropyridin-4-yl)-7-methoxy-2-(trifluoromethyl)pyrazolo[1,5-a]pyridine-4-carboxamide and thalidomide.

3. The method according to claim 1 wherein the subject is a human.

4. A method of modulating aberrant glial activation comprising administering an effective amount of a phosphodiesterase-4 inhibitor and an effective amount of INI-0602 to a subject.

5. The method according to claim 4 wherein the phosphodiesterase-4 inhibitor is selected from the group consisting of propentofylline, apremilast, cilomilast, diazepam, drotaverine, etazolate, filaminast, glaucine, HT-0712, ibudilast, luteolin, mesembrine, mesembrenone, pentoxifylline, piclamilast, rolipram, roflumilast, ronomilast, RPL-554, GSK256066, chlorbipram, MK-0952, MK-0359, MK-0873, KCA-1490, N-(3,5-dichloropyridin-4-yl)-7-methoxy-2-(trifluoromethyl)pyrazolo[1,5-a]pyridine-4-carboxamide and thalidomide.

\* \* \* \* \*